Figure 1:
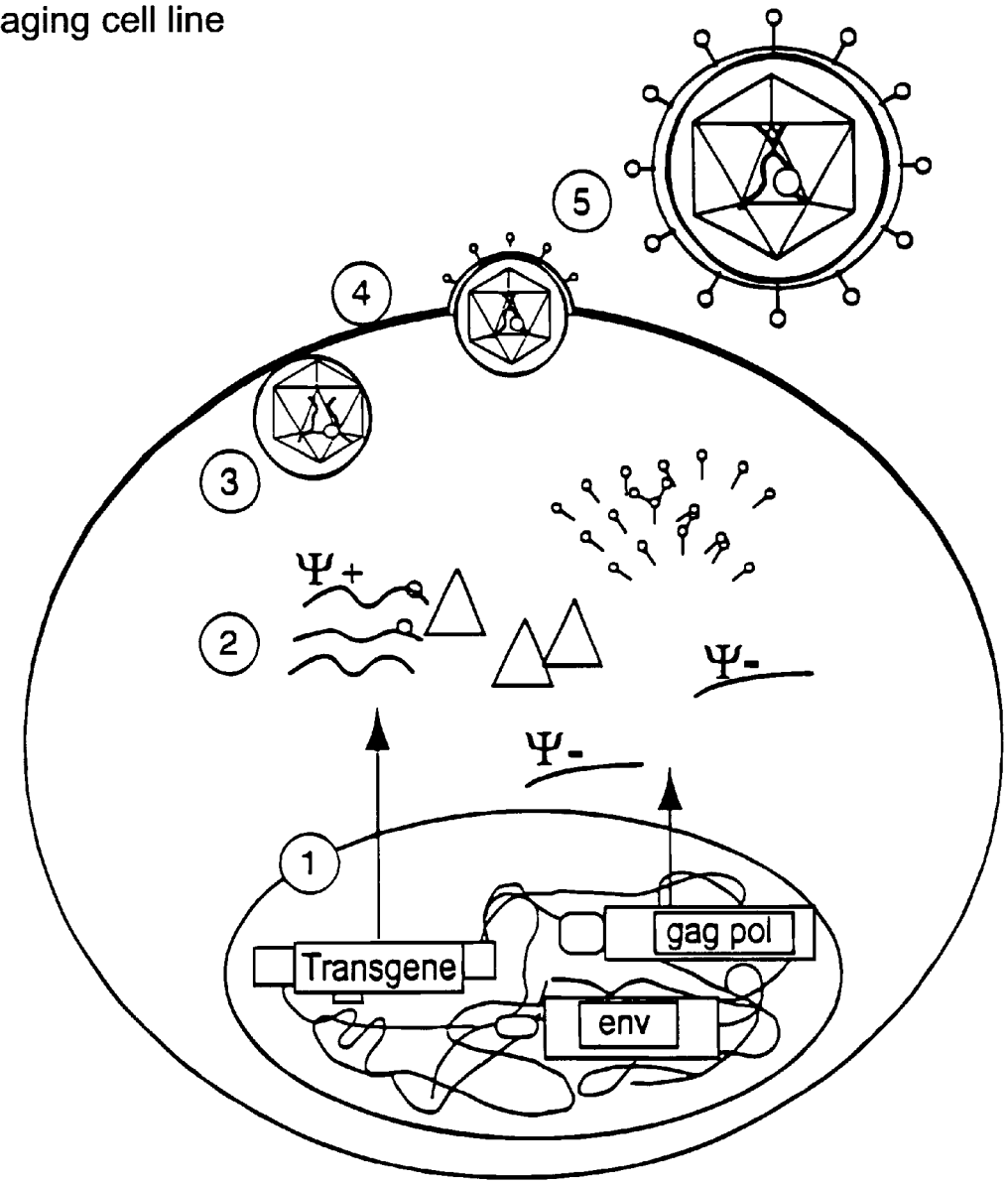
Figure 2:
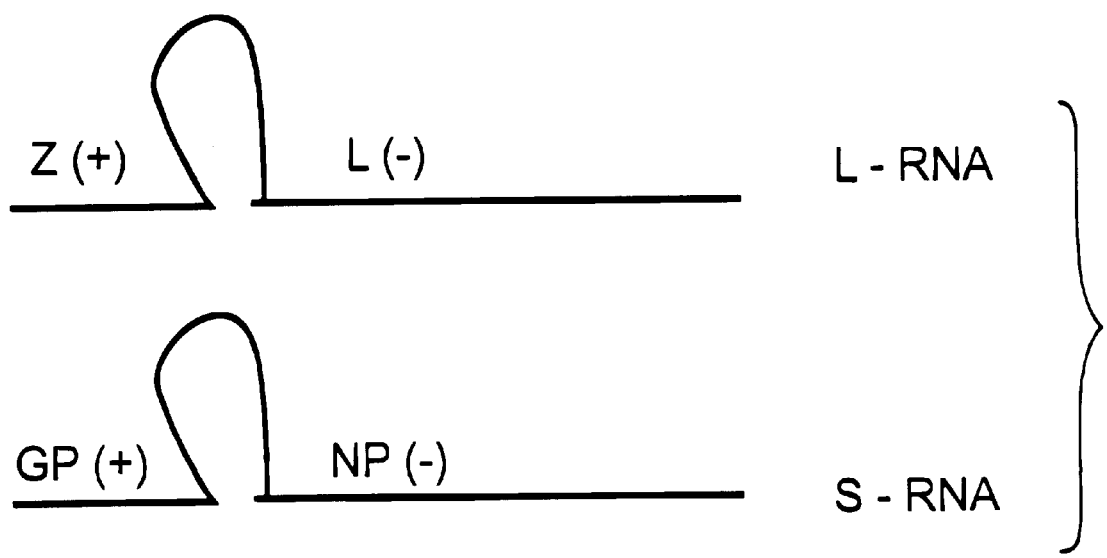

United States Patent
Von Laer et al.

(10) Patent No.: US 6,589,763 B1
(45) Date of Patent: Jul. 8, 2003

(54) RETROVIRAL HYBRID VECTORS PSEUDOTYPED WITH LCMV

(75) Inventors: Meike-Dorothée Von Laer, Hamburg (DE); Winfried Beyer, Hamburg (DE)

(73) Assignee: Heinrich-Pette-Institute, Hamburg (DE)

( * ) Notice: Subject to any disclaimer, the term of this patent is extended or adjusted under 35 U.S.C. 154(b) by 0 days.

(21) Appl. No.: 09/718,096

(22) Filed: Nov. 22, 2000

Related U.S. Application Data

(63) Continuation-in-part of application No. 09/309,572, filed on May 11, 1999, now Pat. No. 6,440,730.

(30) Foreign Application Priority Data

Nov. 26, 1998 (DE) .......................................... 198 56 463
Nov. 25, 1999 (EP) ............................................. 99250415

(51) Int. Cl.$^7$ ......................... C12P 21/06; C12N 15/63; C12N 15/00; C07H 21/04; C07K 1/00
(52) U.S. Cl. ................... 435/69.1; 435/325; 435/320.1; 435/455; 536/23.1; 536/23.72; 530/395
(58) Field of Search ................................ 435/325, 455, 435/320.1, 235.1, 69.1; 536/23.1, 23.72; 530/395

(56) References Cited

U.S. PATENT DOCUMENTS 5,591,624 A   1/1997   Barber et al. ............... 435/366

OTHER PUBLICATIONS

Verma et. al.; Gene therapy–promises, problems and prospects, 1997, Nature, vol. 389: 239–242.*
Branch; A good antisense molecule is hard to find, 1998, TIBS: 45–50.*
Stull et. al.; Antigene, Ribozyme and Aptamer Nucleic Acid Drugs: Progress and Prospects, 1995, Pharmaceutical Research, vol. 12, No. 4: 465–483.*
Rudinger; Characteristics of the amino acids as components of a peptide hormone sequence, 1976, In Peptide Hormones (Parsons, J.A., Ed.), University Park Press, Baltimore, pp. 1–7.*
Ngo et. al.; Computational Complexity, Protein Structure Prediction, and the Levinthal Paradox, 1994. In The Protein Folding Problem and Tertiary Structure Prediction (Merz, K et al., eds.), Birkhauser, Boston, pp. 491–494.*
Salvato et. al.; Virus–Lymphocyte Interactions, 1988, Virology 164: 517–522.*
Stephensen et.al.; cDNA Sequence Sequence Analysis Confirms that the Etiologic Agent of Callitrichid Hepatitis Is Lymphocytic Choriomeningitis Virus, 1995, Journal of Virology: 1349–1352.*
Vogt; Retroviral Virions and Genomes, 1997. In Retroviruses (Coffin, J.M. et al., eds.), Cold Spring Harbor Laboratory Press, New York, pp. 33–38.*
Ally, B.A. et al., J. Immunol. 1995, 155: 5404–5408.
Cosset et al., Journal of Virology, Dec. 1995, 69(12):7430–7436.
Eck, et al., Gene–Based Therapy, 1996, The Pharmacologicl Basis of Therapeutics: 77–101.
Deonarain, Ligand–Targeted Receptor–Mediated Vectors for Gene Delivery, 1998, Exp. Opin. Ther. Patents 8(1): 53–69.
Cosset, et al., Retroviral Retargeting by Envelopes Expressing an N–Terminal Binding Domain, 1995, Journal of Virology, 69(10): 6314–6322.
Ager, et al., Retroviral Display of Antibody Fragments; Interdomain Spacing Strongly Influences Vector Infectivity, 1996, Human Gene Therapy, 7: 2157–2164.
Zhao, et al, Identification of the Block in Targeted Retroviral–mediated Gene Transfer, 1999, Proc. Natl. Acad. Sci. USA, 96: 4005–4010.
Chadwick, et al., Modification of Retroviral Tropism by Display of IGF–1, 1999, J. Mol. Biol.: 285: 485–494.
Teng, M.N. et al: "A single amio acid change in the glycoprotein of lymphocytic choriomenengitis virus is associated with the ability to cause growth hormone deficiency syndrome", Journal of Virology, vol. 70, No. 12

OTHER PUBLICATIONS

Blaese, R. Michael et al: "T Lymphocyte–Directed Gene Therapy for ADA SCID: Initial Trial Results after 4 Years", Science, vol. 270, Oct. 20, 1995, pp. 475–480.

Cavazana–Calvo, Marina et al: "Gene Therapy for Human Severe Combined Immunodeficiency (SCID)–X1 Disease", Science, vol. 288, Apr. 28, 2000, pp. 669–672.

Anderson, W. French, "The Best of Times, the Worst of Times", Science, vol. 288, Apr. 28, 2000, pp. 627–629.

Bonini, Chiara et al: "HSV–TK Gene Transfer into Donor Lymphocytes for Control of Allogeneic Graft–Versus–Leukemia", Science, vol. 276, Jun. 13, 1997, pp. 1719–1724.

Kohn, "T lymphocytes with a normal ADA gene accumulate after transplantation of transduced autologous umbilical cord blood CD 34+ cells in ADA–deficient SCID neotates", Nature Medicine, vol. 4, No. 7, Jul., 1998, pp. 775–780.

Bruns, M. et al: "Lymphocytic choriomeningitis virus", Virology, vol. 137, 1984, pp. 49–57.

Miletic, H. et al: "Retroviral pseudotyped with lymphocytic choriomenengitis virus", Journal of Virology, vol. 73, No. 7, Jul. 1999, pp. 6114–6116.

* cited by examiner

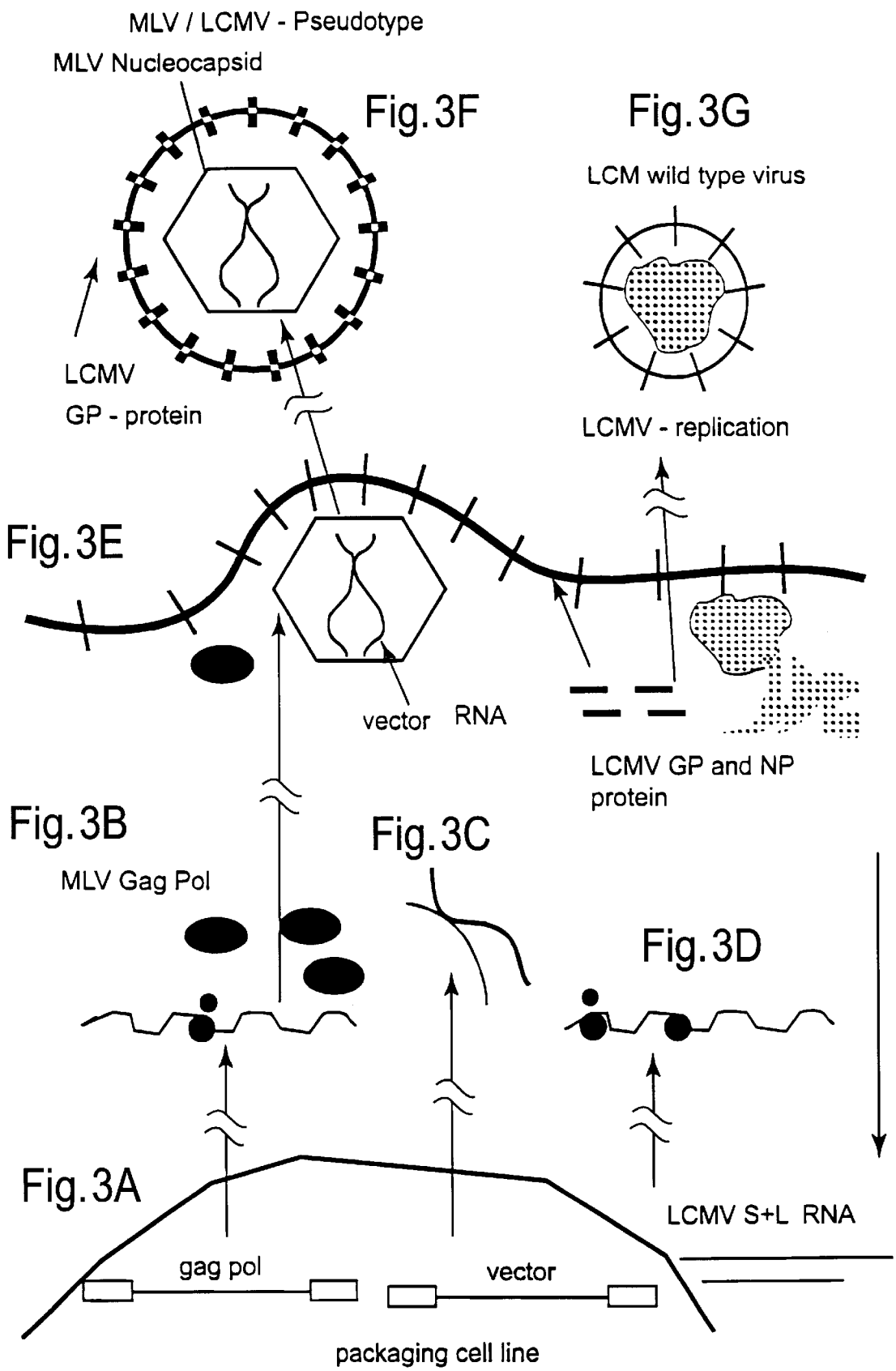

Fig.4A
Ectopic expression of LCMV - GP
LCMV wild - type

Fig.4B
EF1a - promoter

Fig.4C
alphavirus - vector

Fig.4D
CMV - promoter + beta - globin Intron

RETROVIRAL HYBRID VECTORS PSEUDOTYPED WITH LCMV

This application is a Continuation-in-part of U.S. application Ser. No. 09/309,572, filed May 11, 1999, now U.S. Pat. No. 6,440,730, the entire content of which is hereby incorporated by reference in this application.

The present invention relates in general to the pseudotyping of retroviruses with lymphocytic choriomeningitis virus. In particular, the invention relates to pseudotyping in MLV packaging cells which are optionally env-deleted, or in packaging cells derived from lentiviruses. Preferably, pseudotyping is carried out by infection with LCMV or a preferably env-deleted mutant, or by transfection with an expression plasmid containing the gp-gene of LCMV or a part thereof and optionally, in addition, the np-, the 1- and/or the z-gene of LCMV. The invention also relates to the use of such pseudotypes for the infection of cells, particularly the use in gene therapy.

Retroviral vectors are increasingly being used in the state of the art, for example, for gene transfer in genetic engineering and medical research or in gene therapy approaches (cf. e.g. C. Baum et al. in *Seminars in Oncology: Gene Therapy of Cancer: Translational approaches from preclinical studies to clinical implementations.*, eds. Gerson & Lattime, Academic Press, 1998). The retroviral vectors are mostly derived from murine leukaemia viruses (MLV) and contain all the sequences of the LTR regions required for integration and the $\psi$-element responsible for packaging. The regions coding for the virus proteins are replaced by foreign genes and the control sequences thereof which it would be desirable to introduce into human cells. The vectors are expressed in so-called helper cell lines (packaging cell lines) which contain a copy of a complete retrovirus genome. It synthesises all the proteins required for replication and infection, but is unable to package its genomic virus-RNA into particles because it has a defect in the $\psi$-sequences. If the retroviral vectors are inserted into these helper cells and transcribed, the transgenic mRNA formed is able, by means of the $\psi$-region which is characteristic of it, to interact with the structure proteins of the helper virus and be packaged to particles. The recombinant virions, which possess no genetic information at all for virus components, adsorb on cells by way of their surface proteins, the capsids are taken up in the cytoplasm, and the transgenic RNA is converted to double-stranded DNA and integrated into the host cell genome. The advantage of this system is the stable integration of the foreign genes which are passed on to the daughter cells on division. The non-specific integration at arbitrary sites of the cell genome, which is characteristic of retroviruses, is a disadvantage.

Retroviral vectors impart a stable colinear integration (i.e. without recombinations and rearrangement of the coding sequences in the vector genome) and thereby a long-term expression of the transgene. Long-term gene expression has otherwise been possible hitherto only by means of the episomal herpes virus vectors or the adeno-associated virus vectors (AAV vectors). The packaging systems (packaging cell lines) have not yet, however, been optimised for the latter vector systems. Moreover, AAV vectors have a lower packaging capacity (about 5 kb for AAV compared with about 10–12 kb for retroviral vectors).

In addition to the gene to be transferred, the transgene, packaging lines also express the vector genome which contains retroviral cis elements. The genomic vector transcript does not, therefore, code for retroviral proteins but is inserted in the packaging lines with the aid of the gag-, pol- and env-gene products into a virion which is infectious but not capable of replication. This virion may then be used as a retroviral vector for transferring the transgene integrated into the vector genome into the desired target cells without further proliferation of the vector occurring there. In other words, the viral vector is only able to infect the target cells but is unable to proliferate any further therein.

The development of retroviral packaging systems is already well advanced and vector supernatants that are free from viruses capable of replication can be produced in large quantities under GMP conditions (Good Manufacturing Practice; Directive of the Commission for laying down principles and guidelines of good manufacturing practice (GMP) for certain medicaments for use in humans (91/356/EEC) of 13.6.91). Vectors based on murine leukaemia virus (MLV vectors) have already been used repeatedly in clinical trials (P. Chu et al., J. Mol. Med. 76 (1998) 184–192).

Two fundamental types of retroviral packaging systems are known in the prior art (J. M. Wilson, Clin. Exp. Immunol. 107 Suppl. 1 (1997) 31–32; C. Baum et al. 1998), loc cit.).

MLV packaging cell lines contain the retroviral genes gag, pol and env (FIG. 1) and the sequences required for packaging the retroviral RNA are deleted (C. Baum et al., (1998), loc. cit.).

The second type of known packaging systems is derived from the lentiviruses (R. Carroll et al., J. Virol. 68 (1994) 6047–6051; P. Corbeau et al., Proc. Natl. Acad. Sci. USA 93 (1996) 14070–14075; L. Naldini et al., Science 272 (1996) 263–267; C. Parolin et al., J. Virol. 68 (1994) 3888–3895; J. Reiser et al., Proc. Natl. Acad. Sci. USA 93 (1996) 15266–15271; J. H. Richardson et al., J. Gen. Virol. 76 (1995) 691–696; T. Shimada et al., J. Clin. Invest. 88 (1991) 1043–1047). Lentiviruses are complex retroviruses which, in addition to the gag, pol and env gene products also express a series of regulatory genes. Examples of lentiviruses from which packaging systems were derived are the human immunodeficiency virus (HIV), the "simian immunodeficiency virus" (SIV) and the "feline immunodeficiency virus" (FIV). The structure of the lentiviral packaging systems is similar, in principle, to that of the MLV vectors.

An advantage of lentiviral vectors is that they are also able to infect resting cells. In the case of MLV vectors, on the other hand, the vector genome can be transported into the cell nucleus only during cell division, i.e. when the nuclear membrane is dissolved. However, in view of the complex structure of the lentiviral genome, packaging systems derived from lentiviruses have disadvantages which are manifested in a comparatively low titre and relatively poor stability. Due to the complex genome structure, cis and trans elements in the genome cannot be separated clearly from one another. In the packaging constructs that express lentiviral gag, pol and env genes there are also to be found, therefore, important cis-regulatory sequences (e.g. parts of the packaging signal) which must also be contained in the vector genome. Due to these homologies, recombinations between vector genome and the packaging constructs may occur and thus the release of retroviruses capable of replication (e.g. an HIV wild virus which would be highly undesirable), so these systems are not comparable with MLV packaging lines.

All the vector systems known hitherto in the prior art also have some crucial shortcomings which prevent successful use in gene therapy: 1. Retroviral vectors are mostly produced only in inadequate titres and cannot be concentrated any further due to the instability of their envelope proteins. 2. Vector particles cannot be purified without loss of infectiousness due to the instability of their envelope proteins. Such purification is essential, however, as the cell culture supernatants from which vectors are harvested are contaminated by cellular constituents. 3. Due to their envelope proteins, retroviral vectors are inactivated by human serum complement. 4. The receptor for the envelope protein of the classic amphotrophic vectors is expressed on virtually all the cell lines considered. However, many primary human cells such as hepatocytes and haematopoietic stem cells which are attractive targets of gene therapy are deficient in functional amphotrophic receptors, as a result of which transduction is rendered difficult or prevented.

The object of the present invention is, therefore, to provide retroviral packaging systems which do not have the disadvantages of the packaging cell lines known in the prior art.

In particular, the object of the present invention is to provide packaging systems which permit a stable retroviral transfer of transgenes into the target cells, i.e. which lead to stable integration of the transgene into the genome of the target or host cells followed by stable expression of this gene.

The object according to the invention is achieved in that retroviruses are pseudotyped with lymphocytic choriomeningitis virus (LCMV).

The present invention relates, therefore, to a recombinant virion which is preferably transfected with one or more foreign genes, which may be obtained by pseudotyping the virus particle with lymphocytic choriomeningitis virus (LCMV).

The tropism and also the stability of a virus is determined primarily by the envelope protein. Murine retroviruses are able to incorporate not only the MLV-env coded glycoproteins but also envelope proteins of other types of virus into their virus coat. As a result, so-called pseudotypes are produced. Retroviral pseudotype vectors are produced by expression of foreign viral envelope proteins in MLV packaging lines. Conventional MLV packaging cell lines contain the retroviral genes gag, pol and env. Sequences which are necessary for the packaging of retroviral genomic RNA were deleted. A vector is introduced into such packaging lines which contains not only the gene which is to be transferred but also the retroviral packaging sequence and other retroviral cis elements (LTR, leader). The retroviral RNA genome is inserted with the aid of the gag, pol and env gene products into a virion which is infectious but not capable of replication. This virion can then be used as a retroviral vector for the transduction of cells. Pseudotype packaging lines also contain the envelope protein gene of a foreign virus. The pseudotype packaging lines according to the invention contain the envelope protein gene of LCMV, and expression of the LCMV glycoproteins takes place.

The present invention provides for the first time vector systems which may be produced in high titres and concentrated. The vector particles according to the invention can also be purified without or without any substantial loss of infectiousness. Surprisingly, it has become apparent within the scope of the present invention that the pseudotyping according to the invention is not cytotoxic for the packaging cells. Stable packaging cell lines (packaging systems) are thus provided for the first time which permit a stable retroviral transfer of transgenes into the target cells, i.e. which lead to a stable integration of the transgene into the genome of the target or host cells followed by stable expression of this gene.

The cell lines according to the invention are also characterised by a broad, trans-species host cell spectrum (cell tropism). A crucial advantage of the present invention is the fact that individual mutations in the envelope protein of LCMV can lead to a modification of the tropism of LCMV. That is, due to individual point mutations in gp, viruses that are more likely to infect nerve cells become viruses that are more likely to infect lymphocytes or those that are more likely to infect monocytes.

Within the scope of the present invention, LCMV is used for pseudotyping. It is possible or it may even be preferable to use other strains of LCMV instead of the LCMV wildtype. Slight variations in the gp nucleic acid sequence or in the amino acid sequence of the expressed envelope protein in various strains of LCMV may thus alter substantially the cell tropism (host cell spectrum) of LCMV (M. Matloubian et al., J. Virol. 67 (1993) 7340–7349; M. N. Teng, J. Virol. 70 (1996) 8438–8443; King et al., J. Virol 64; 1990, 5611–5616). No such tropism variants in the glycoprotein are found for any of the other retroviral vector systems known hitherto, and a more targeted transduction of the desired cell type is made possible for the first time according to the invention. According to a preferred embodiment of the invention, it may therefore be advantageous to provide packaging systems with various glycoprotein variants (GP variants) for different applications.

Within the scope of the present invention, the starting material is the gp genes of the neurotropic LCMV strain Armstrong, L(ARM) (L. Villarete et al., J. Virol. 68 (1994) 7490–7496) (region coding for SEQ ID NO: 4; compare appendix to the sequence protocol, re SEQ ID NO: 3), and of the haematotropic strain WE (V. Romanowski et al., Virus Res. 3, (1985) 101–114) (SEQ ID NO: 1). Also included according to the invention are variants (tropism variants) of these two strains in which individual amino acids are exchanged in the gp gene product, since the tropism of the virus can thereby be altered.

It is rather probable that "cryptic splice regions" are located in the RNA sequence, since LCMV is an RNA virus without a nuclear phase during the propagation cycle. The removal of such regions (correction for aberrant splicing) can be utilised to achieve an improved expression. Such "splice-corrected" variants are also, therefore, included according to the invention. Pseudotyping can be improved by such optimisation of GP expression, whereby it is possible to dispense with an additional support by means of at least one further LCMV protein.

A preferred variant is the mutant WE-HPI, which has been developed according to the present invention, which nucleic acid gp coding for GP (Open Reading Frame (ORF) shown in SEQ ID No. 25) contains mutations at positions 281, 329, 385, 397, 463, 521, 543, 631, 793, 1039, 1363 and 1370 as compared to the LCMV strain WE, which encodes the GP variant shown in SEQ ID NO. 26, the latter of which shows amino acid replacements at positions 94, 110, 129, 133, 155, 174, 181, 211, 265, 347, 455 and 457 as compared to SEQ ID NO. 2. This GP variant has the advantage that it is stable even without additional LCMV aiding proteins and, compared to strain WE, achieves an improved pseudotyping.

The invention therefore further relates to a variant of the lymphocytic choriomeningitis virus, containing the gene gp, which encodes the sequence shown in SEQ ID NO. 26 or a part thereof, wherein the gp gene preferably has the sequence shown in SEQ ID NO. 25 or a part thereof. Further included according to the invention is a protein having the amino acid sequence shown in SEQ ID NO. 26 or a part thereof, as well as a nucleic acid encoding this protein, preferably the sequence shown in SEQ ID NO. 25 or a part thereof. This virus variant as well as the nucleic acid sequences and amino acid sequences last mentioned, are obtainable, for example starting from the LCMV variant WE by methods generally known to the skilled person (for example by introducing point mutations).

Generally speaking, expression vectors which permit a high, stable gene expression in eukaryotic cells are suitable for the expression of LCMV. The choice of expression vector is, however, crucial for the packaging of the retroviral LCMV pseudotypes only insofar as it must guarantee a high and stable level of expression, i.e. a level of expression which is high enough to permit the formation of pseudotypes and which is durable (stable) without switching off of the promoter occurring.

The following two expression cassettes are particularly preferred according to the invention:

(CMV promoter)—(β-globin-intron-2)—(gp)—(SV40 poly A-signal)

and (EF-1alpha promoter)—(gp)—(poly-A signal of the G-CSF gene)

(S. Mizushima, Nucleic Acids Res. 18 (1990) 5322, T. Uetsuki, J. Biol. Chem. 264 (1989) 5791–5798).

The sequences for the constituents of the expression cassettes are shown in the sequence protocol or are generally well known:
  cytomegalovirus promoter (CMV promoter):
    (M. Boshart et al., Cell 41 (1958) 521–530; F. Langle-Rouault et al., Virol. 72 (7) 6181-5 (1998))
  betaglobin-intron-2:
    (Jeffreys, A. J. et al., Cell 12 (1977) 1097–1108)
  SV40 poly A signal:
    (M. Boshart et al., Cell 41 (1958) 521–530; F. Langle-Rouault et al., Virol. 72 (7) 6181-5 (1998))
  EF-1alpha promoter: SEQ ID NO: 9
    (S. Mizushima, Nucleic Acids Res. 18 (1990) 5322, T. Uetsuki, J. Biol. Chem. 264 (1989) 5791–5798).
  G-CSF poly A signal:
    (S. Mizushima, Nucleic Acids Res. 18 (1990) 5322, T. Uetsuki, J. Biol. Chem. 264 (1989) 5791–5798).
  gp (LCMV):
    compare SEQ ID NO: 1, 3, region coding for SEQ ID NO: 4 (see also Appendix to the sequence listing).

Within the scope of the present invention, the above-mentioned expression cassettes are also therefore included, changes in the relevant nucleic acid sequences being possible as long as the functionality of the expression cassettes remains intact, i.e. their use according to the invention permits pseudotyping of the packaging cells and also does not prevent the transfection of the target cells and the stable integration of the transgenes into the host genome.

Moreover, an episomal EBV expression vector (Epstein-Barr-Virus; cf. F. Langle-Rouault et al., Virol. 72 (7) 6181–5 (1998)) (pCep4) from Invitrogen also exhibits high expression and is therefore preferred within the scope of the present invention.

The present invention also provides, therefore, a packaging cell which contains the retroviral genes gag (region coding for SEQ ID NO: 12; cf. Appendix to the sequence listing, re SEQ ID NO: 11), pol (region coding for SEQ ID NO: 13; cf. Appendix to the sequence listing, re SEQ ID NO: 11) and optionally the retroviral gene env (region coding for SEQ ID NO: 14; cf. Appendix to the sequence listing, re SEQ ID NO: 11) and/or regulatory retroviral genes (in the case of lentiviral packaging systems, see below, e.g. the gene coding for the lentiviral Rev protein which prevents splicing of the retroviral genomic RNA) and also contains the gene gp coding for the glycoproteins GP-1 and GP-2 of LCMV (region coding for SEQ ID NO: 4; cf. Appendix to the sequence listing, re SEQ ID NO: 3) or a part thereof. Also included are nucleic acid sequences which exhibit modifications or deviations (mutations, deletions etc.) in the sequences as long as, when used according to the invention, the pseudotyping of the packaging cells is guaranteed and the transfection of the target cells and the stable integration of the transgenes into the host geriome is not impeded. This includes fragments of the named sequences. These derivatives should always be included hereinafter when any gene as such is mentioned.

Within the scope of the present invention, "GP" or "GP protein" denotes the GP-C precursor protein from which GP-1 and GP-2 are then produced by proteolytic cleavage, these being denoted hereinafter simply "LCMV glycoprotein".

According to the invention, moreover, pseudotype packaging systems are provided in which, apart from the gp gene product (SEQ ID NO: 4), one or more other genes of LCMV are expressed such as, for example, the gene np coding for the nucleoprotein (region coding for SEQ ID NO: 5; cf. Appendix to the sequence listing, re SEQ ID NO: 3), the gene z coding for a protein with an unknown function (region coding for SEQ ID NO: 8; cf. Appendix to the sequence listing, re SEQ ID NO: 6) and the gene l coding for RNA polymerase (region coding for SEQ ID NO: 7; cf. Appendix to the sequence listing, re SEQ ID NO: 6). According to a particular embodiment of the invention, these genes may stem either from the WE or Armstrong strain of LCMV. In this connection, either the complete sequences of the genes np, z and/or l (SEQ ID NOs: see above) or parts thereof may be used. Sequences included according to the invention are nucleic acid sequences which exhibit modifications or deviations (mutations, deletions etc.) in the sequences (derivatives), as long as pseudotyping of the packaging cells is guaranteed and the transfection of the target cells and the stable integration of the transgenes into the host genome is not impeded. This includes fragments of the named sequences. These derivatives should always be included hereinafter when any gene as such is mentioned.

The invention also provides, therefore, a packaging cell which, in addition to the gp gene of LCMV, contains at least one gene from the group comprising the gene np coding for the nucleoprotein, the gene l coding for RNA polymerase and the gene z of LCMV coding for a protein of unknown function.

The MLV/LCMV pseudotypes, i.e. recombinant retroviral virions which contain the LCMV glycoprotein incorporated in their coat, are produced by the packaging cells according to the invention.

For the production of the recombinant virions, the starting materials for the viral packaging cell lines within the scope of the present invention are preferably all the cell lines that produce high titres of retroviral vectors. Cell lines used in preference are NIH3T3, Te671, 293T, HT1080 (F. L. Cosset et al., J. Virol. 69 (1995) 7430–7436; D. Markowitz et al., Virology 167 (1988) 400–406); W. S. Pear et al., PNAS 90 (1993) 8392–8396). The choice of cell line is not important, however, for the specific advantages of the invention because it has become apparent that GP does not have a toxic effect in any cell line examined hitherto. If, therefore, lines should be found in the future which permit a more efficient vector production (i.e. more stable titre which is at least as high as in the above-mentioned lines, $>10^6$/ml), these may also be used.

The gag and pol genes of the Moloney strain of murine leukaemia viruses (MOMLV) are expressed in the packaging systems used in preference for pseudotyping according to the invention (gag: region coding for SEQ ID NO: 12, pol: SEQ ID NO: 11, Nukleotide 1970–5573; cf. Appendix to the sequence listing, re SEQ ID NO: 11). According to the invention, however, other gag and pol variants of MLV are also included as long as they exhibit the above-mentioned advantages for vector production. In particular, the above-mentioned gene derivatives are included according to the invention.

It was ascertained within the scope of the present invention that LCMV-GP also pseudotypes lentiviral nucleocapsids (see examples). According to a particular embodiment, the packaging systems may also therefore contain the gag and pol gene products of lentiviruses, i.e. lentiviral packaging systems (packaging cell lines) may be used. It is immaterial from which lentivirus the packaging system is derived. Suitable lentiviral packaging cells within the scope of the present invention include, for example, cell lines derived from human immunodeficiency virus (HIV), simian immunodeficiency virus (SIV) or feline immunodeficiency virus (FIV). In this connection, it could be necessary for an efficient production of infectious lentivirus vectors to express, in addition, accessory lentiviral genes such as rev (region coding for SEQ ID NO: 21; cf. Appendix to the sequence listing, re SEQ ID NO: 15) or tat (region coding for SEQ ID NO: 20; cf. Appendix to the sequence listing, re SEQ ID NO: 15) in the case of HIV vectors. Within the scope of the present invention, LCMV proteins may be used for pseudotyping in all the lentiviral packaging systems.

The present invention also provides a (viral) packaging cell or a pseudotyped virion in which the virus is selected from the family of retroviridiae, particularly the MLV-related viruses and the lentiviruses. According to a particular embodiment of the invention, the retroviral packaging cell is selected from the group comprising packaging cells derived from MLV, HIV, SIV and FIV.

According to the invention, moreover, a pseudotyped virion is provided which can be obtained by pseudotyping a retroviral cell of MLV which does not express an ENV protein, the defective mutant L(ARM) of LCMV being used for pseudotyping. Alternatively, other variants of LCMV may also be used.

The present invention also provides a process for the production of the packaging cells/packaging cell lines according to the invention, wherein a retroviral packaging cell line transfected with one or more foreign genes is infected with LCMV according to known methods (cf. e.g. Maniatis, Sambrook, Fritsch: Molecular cloning, a laboratory manual; Cold Spring Harbor Laboratory Press, 1982). The virions which contain LCMV glycoprotein incorporated in their coat are expressed by the packaging lines. According to a particular embodiment of the invention, the pseudotype-producing packaging cells may be produced by transfecting a retroviral packaging cell line transfected with one or more foreign genes with an expression plasmid which contains the gp gene of LCMV or a part thereof and optionally, in addition, one or more genes from the group comprising np, l and z of LCMV.

The present invention also relates, therefore, to a process for the production of retroviral pseudotype vectors wherein retroviral packaging cells containing at least the gp gene of LCMV or a part thereof (see above) are produced initially and these are then cultivated under conditions that are suitable for the production of virions.

Within the scope of the present invention, the retroviral packaging cell line used is preferably an MLV packaging cell line which does not express a functional ENV protein and the LCMV used for pseudotyping is the deleted mutant L(ARM). The cell line described by von Laer et al. (J. Virol. 72 (1998) 1424–1430) may also be used as the ENV-negative packaging cell line.

The virions or packaging cells lines according to the invention may be used advantageously for producing viral pseudotype vectors which may be used advantageously for the transduction of cell lines but also of primary eukaryotic cells for research purposes (in vitro) or within the context of gene therapy.

The use of virions/packaging cells for gene therapy also comes into consideration, however, within the scope of the present invention. In this connection, gene therapy may include the treatment of infectious diseases (such as HIV infections or AIDS) and neoplasms (such as breast cancer/mamma carcinoma) or melanoma and other diseases accessible by gene therapy. The transduction of haematopoietic stem cells also comes into consideration within the scope of the present invention.

The recombinant virion or the recombinant packaging cell (cell line) of the present invention comprises one or more transgenes. Preferably, said transgenes are selected from the group comprising marker genes such as, e.g. neo, lacZ or enhanced green fluorescent protein (EGFP) and/or genes which may be used therapeutically, such as, e.g. the suicide gene herpes simplex virus thymidine kinase (HSV-tk), cytosine deaminase (CD) and sequences with an antiviral effect such as ribozymes, antisense sequences and transdominant-negative genes and genes that may be used in tumour therapy such as mdr-1 for the protection of haematopoietic cells in chemotherapy, and cytokine genes. Moreover, all transgenes which could be of interest within the context of a targeted gene transfer and the expression of the transgene(s) in cells in vitro or within the context of gene therapy may, however, be used.

The invention also includes a process for the preparation of a pharmaceutical preparation for gene therapy wherein viral pseudotype vectors or retroviral packaging cells according to the invention are formulated optionally with pharmaceutically compatible excipients and/or carriers. The present invention also provides a pharmaceutical preparation for gene therapy which comprises retroviral packaging cells according to the invention and optionally pharmaceutically compatible excipients and/or carriers.

It is often essential for gene therapy in vivo that only specific target cells are genetically altered, but not other cells. For example, a suicide gene shall enter tumor cells only but not healthy cells, a chemotherapy resistance gene shall enter healthy blood stem cells but not contaminating tumor cells. For the more targeted gene transfer into specific cells it has been tried already to incorporate ligands into the coat of retroviral vectors or into liposomes. A targeted gene transfer, however, was not possible so far by utilizing these methods since the ligands only mediate the binding to the target cell but not the entry of the vector genome into the cytoplasm (F. L. Cosset et al., J. Virol. 69 (1995) 6314–6322), i.e. no fusion with the membrane of lysosomes occurs. This problem can be solved by using viral coat or envelope proteins having fusion activity, i.e. proteins which surmout the lysosomal membrane as fusion proteins. The use of LCMV GP is a considerable advantage in this context, since this viral envelope protein undergoes a conformational change at low pH, as it predominates in the endosome of the target cell. The conformational change leads to the activation of the fusion function, even without the requirement of receptor binding of the LCMV GP. Since LCMV GP—in contrast to other fusion proteins—does not mediate fusion of cell membranes, it is not cytotoxic and does not lead to formation of giant cells (cf. C. di Simone et al., Virology 198 (1994) 455–465).

According to the present invention, retroviral packaging cells are included, which contain the retroviral genes gag, pol and env and/or regulatory retroviral genes and further the gene gp coding for the glycoproteins GP-1 and GP-2 of LCMV or a part thereof, wherein env is modified in that it encodes an Env protein, which mediates a specific binding to the target cell (so-called targeting-env) and wherein gp is a variant, which encodes a GP protein having fusion activity (so-called fusion helper). Further enclosed are methods for the preparation of these packaging cells, in which a packaging cell is used as retroviral packaging cell, which contains the retroviral gene env, which is modified in that it encodes an Env protein, which mediates a specific binding to the target cell and wherein gp is a variant, which encodes a GP protein having fusion activity. In this context it might be necessary to mutate the part of the sequence encoding the receptor binding site of LCMV GP (without impairing the fusion activity) in order to prevent or reduce binding of GP to its cellular receptor. Alternatively, the use of neutralizing antibodies against GP is to be considered, which are able to neutralize the receptor binding without inhibiting the pH-dependent fusion by GP. Due to the fact that according to the present invention, for the first time stable packaging cell lines are provided, it is now possible to identify the receptor binding site by targeted mutagenesis of GP-1. This method as well as the isolation of the mentioned neutralizing antibodies are well-known to the skilled person.

The present invention provides for the first time vector systems which may be produced in high titres and concentrated. The vector particles according to the invention may also be purified without or without any substantial loss of infectiousness. The cell lines according to the invention are also characterised by a broad, trans-species host cell spectrum (cell tropism). Surprisingly, it has become apparent within the scope of the present invention that the pseudotyping according to the invention is not cytotoxic for the packaging cells. Stable packaging cell lines (packaging systems) are thus provided for the first time which permit stable retroviral transfer of transgenes into the target cells, i.e. which lead to a stable integration of the transgene in the genome of the target or host cells followed by stable expression of this gene.

The present invention will be explained below on the basis of examples, figures and a sequence listing.

EXAMPLES

Materials and Methods

Cells and Viruses

The env-negative packaging cell line TELCeB was provided by F.-L. Cosset (F. L. Cosset et al. J. Virol. 69 (1995) 7430–7436). The env-negative cell line 293gp2 has already been described (D. Von Laer et al., J. Virol. 72 (1997) 1424–1430). The mouse fibroblast cell line Sc-1 was cultivated in Minimal Essential Medium (Sigma, Deisenhofen, Germany) which had been enriched with 10% foetal calf serum (FCS, PAN Systems, Aidenbach, Germany). The human kidney cell line 293, the human hepatoma line HUH-7, the human fibroblast cell line Te671 and TELCeB and the mouse fibroblast cell line L-929 were cultivated in Dulbecco's Minimal Essential Medium (DMEM, Gibco, Paisley, Great Britain) which had been enriched with 10% FCS. The human haematopoietic precursor cell line TF-1 was kept in Iscove's Modified Dulbecco's Medium (Gibco, Paisley, Great Britain) which had been enriched with 10% FCS and IL-3. Conditioned medium of NIH3T3 cells which had been transfected with a BPV vector carrying the IL-3 gene were used as the source of IL-3 in concentrations that are required for maximum growth of TF-1 (H. Karasuyama et al., Eur. J. Immunol 18 (1988) 97–104). The human precursor cell line K562 was kept in RPMI (Gibco) which had been enriched with 10% FCS.

LCMV was deposited on 10.11.1998 at the European Collection of Cell Cultures (ECACC), Salisbury, Wiltshire SP4 OJG, Great Britain under the access number V98111005 according to the Budapest Treaty.

The MESV-type retroviral vector which carries the neomycin phosphotransferase gene (MPLN) has already been described (H.-G. Eckert, Blood 88 (1996) 3407–3415). The amphotrophic helper was a recombinant Moloney MLV capable of replication in which parts of the pol and the majority of the env gene had been replaced with that of the MLV strain 4070A [Mo-Ampho-MP, R320 (C. Munk, Proc. Natl. Acad. Sci. USA 94 (1997) 5837–5842)] as a SaiII to ClaI fragment. The virus was propagated in Sc-1. The plaque-purified WE strain of the LCM virus was propagated in L-929 cells (T. M. Rivers, Virology 26 (1965) 270–282).

Continuous Flow Cytometric Analysis of LCMV-GP Expression

In order to analyse the expression of the LCMV glycoprotein, $3 \times 10^5$ to $10^6$ cells were harvested, pelleted and resuspended in 50 µl of a 1:40 dilution of mouse ascites which contained a murine monoclonal antibody against LCMV GP-1 (M. Bruns et al., Virology 130 (1983) 247–251). After 20 minutes' incubation on ice, the cells were washed three times with phosphate-buffered saline (PBS) and then incubated for a further 20 minutes in a 1:80 dilution of an FITC labelled goat anti-mouse antibody (Dako, Glostrup, Denmark). After three final wash stages in PBS, the cells were analysed using an FACScalibur device (Becton Dickinson, Heidelberg).

Titration of the Viruses

In order to determine the vector titre, $5 \times 10^4$ Sc-1 cells were inoculated with a five-fold dilution of the supernatants in 24-well tissue culture plates. For the retroviral neovector the selection was initiated after 24 hours with 400 µg G418 per ml (dry weight GIBCO). The medium was replaced every four days. The colonies were evaluated after ten days. The titre was expressed as G418 resistance transfer units per ml (GTU/ml). For the retroviral MFGnlsLacZ vector, X-gal (5-bromo-4-chloro-3-indolyl-β-D-galactopyranoside) staining was carried out two days after inoculation as described earlier (G. R. McGregor, Methods Mol. Biol. 7 (1989) 1–19). The titre was expressed in LacZ transfer units (LTU) per ml. Plaque-forming units of LCMV were assayed on L-929 cells as described previously (F. Lehmann-Grube, J. Gen. Virol. 37 (1977) 85–92).

MLV (LCMV) pseudotypes were neutralised by preincubation of an equal volume of a virus-positive supernatant with an anti-LCMV gp44-neutralising monoclonal antibody which was diluted 1:100 (M. Bruns et al., Virology 130 (1983) 247–251). The titres were then determined in LTU per ml as described.

DNA Analysis

The production of DNA and Southern blot analysis were carried out as described earlier (C. Stocking et al., Cell 53 (1988) 869–879). The genomic DNA was digested with HINDIII which makes a single cut at the 3' end of the neo gene in the MP1N vector. A fragment which contains the complete neo gene was used as a probe.

Production and Purification of the Virus

The virions were purified by gradient ultracentrifugation as described in detail earlier (L. Martinez-Peralta et al., J. Gen. Virol. 55 (1981) 475–479). In short, infectious cell culture supernatants were purified by centrifugation at low and high speeds. The virus was pelleted by ultracentrifugation and then purified in a 0–40% Urografin gradient (Schering AG, Berlin, Germany).

Example 1

Figure 6:
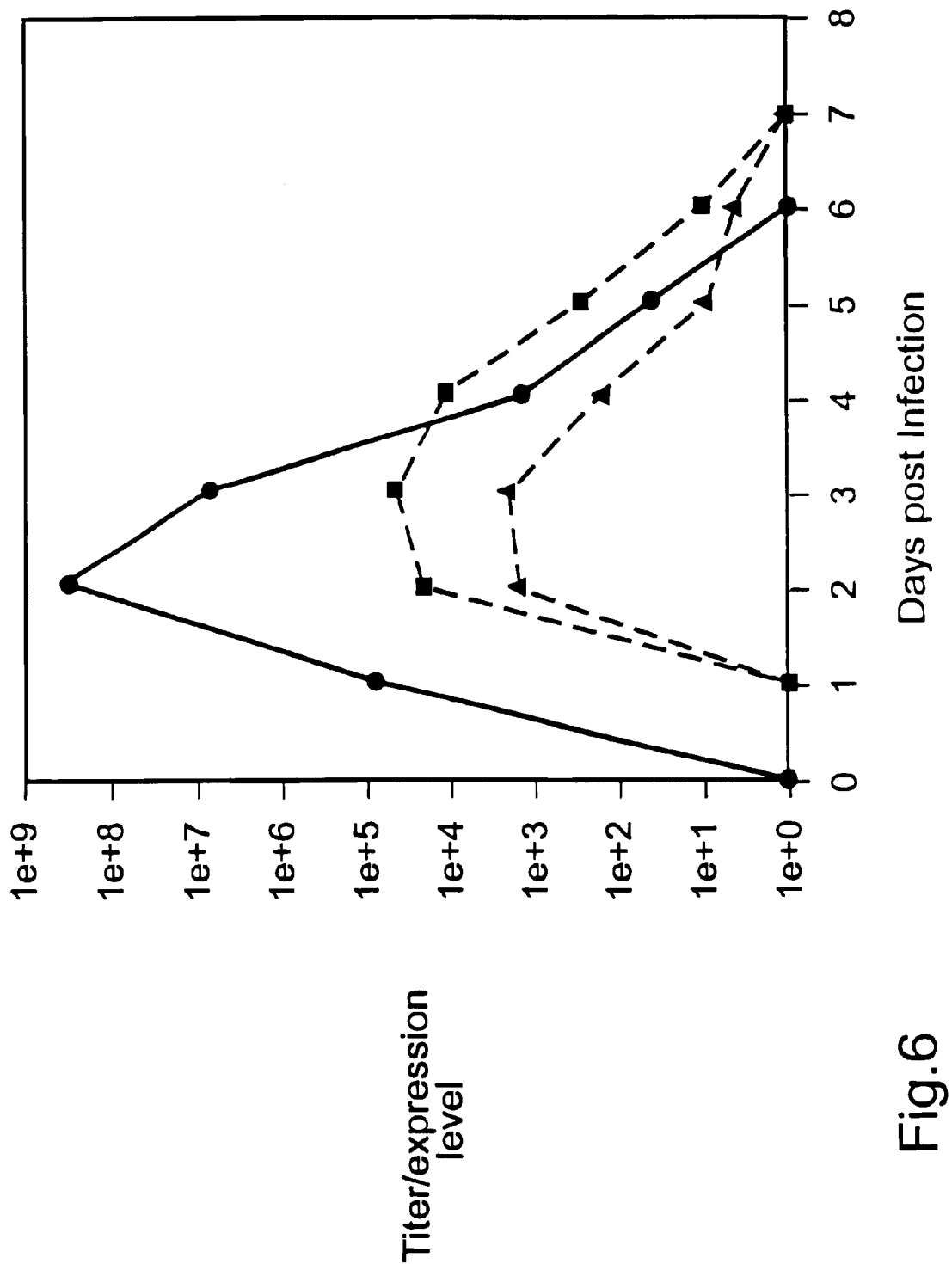

Infection of TeLCeb with LCMV-LacZ Gene Transfer to Target Cells with Neutralisation of the Vector by Anti-GP Mab and Concentration of the Vector in the Gradient Rescue of an envelope protein-negative murine leukaemia virus vector with lymphocytic choriomeningitis virus: In order to find out whether LCMV is able to rescue (mobilise, complete) an envelope protein-negative retroviral vector, the env-negative packaging cell line TELCeB was infected with the LCMV WE strain in an m.o.i. of 0.01 (m.o.i.: multiplicity of infection; denotes the number of virus particles with which a cell is infected). TELCeB stem from the human fibroblast cell line Te671 and contain gag and pol genes as well as the retroviral vector MFGnlsLacZ (G. M. Crooks et al., Blood 82 (1993) 3290–3297). After infection with LCMV, the titre of LacZ transferring units (LTU) and of LCMV wild-type virus was measured by X-gal staining of the mouse fibroblast target cells (Sc-1 ) and by a plaque test (in plaque-forming units, PFU). In addition, the expression of LCMV glycoproteins in the infected TELCeB was measured by continuous flow cytometric analysis. The results are shown in FIG. 6. LTU were prepared for six days with a maximum of $5 \times 10^4$ LTU per ml on day 3. The highest titre for LCMV wild-type virus was $3 \times 10^8$ on day 2. The production of PFU had already decreased on day 3 when the maximum production of LTU together with the highest expression of LCMV glycoprotein was to be seen. The reason for this discrepancy could lie in the production of defective interfering LCMV particles which inhibit the replication of LCMV wild-type, but in all probability not the release of infectious retroviral vector particles. No obvious cytopathic effect was to be observed during the replication of LCMV in the packaging cell lines, although high levels of LCMV glycoproteins were expressed (data not shown).

A test was then carried out to find out whether the infectious virus which was produced by the LCMV-infected TELCeB mediated the LacZ gene transfer specifically by way of LCMV glycoproteins. The supernatants were incubated for one hour with a neutralising anti-LCMV gp44 monoclonal antibody. This led to a more than threefold log reduction of the LTU titre. The amphotrophic pseudotype of the same retroviral vector was not neutralised by the anti-LCMV antibody (Tab. 1). These data show that the MLV/LCMV chimeric virions actually carried LCMV glycoproteins on their surface which are able to mediate gene transfer in the absence of retroviral envelope proteins by means of the LCMV receptor.

Tab. 1: Infectious retroviral vector particles which are produced by LCMV-infected packaging cell lines can be neutralised by anti-LCMV glycoprotein monoclonal antibodies (mab).

| Virus | anti-LCMV mab | Titre (LTU/ml) |
|---|---|---|
| Amphotrophic helper | no | $2 \cdot 10^5$. |
| Amphotrophic helper | yes | $2 \cdot 10^5$ |
| LCMV | no | $7 \cdot 10^4$ |
| LCMV | yes | $3 \cdot 10^1$ |

Figure 7:
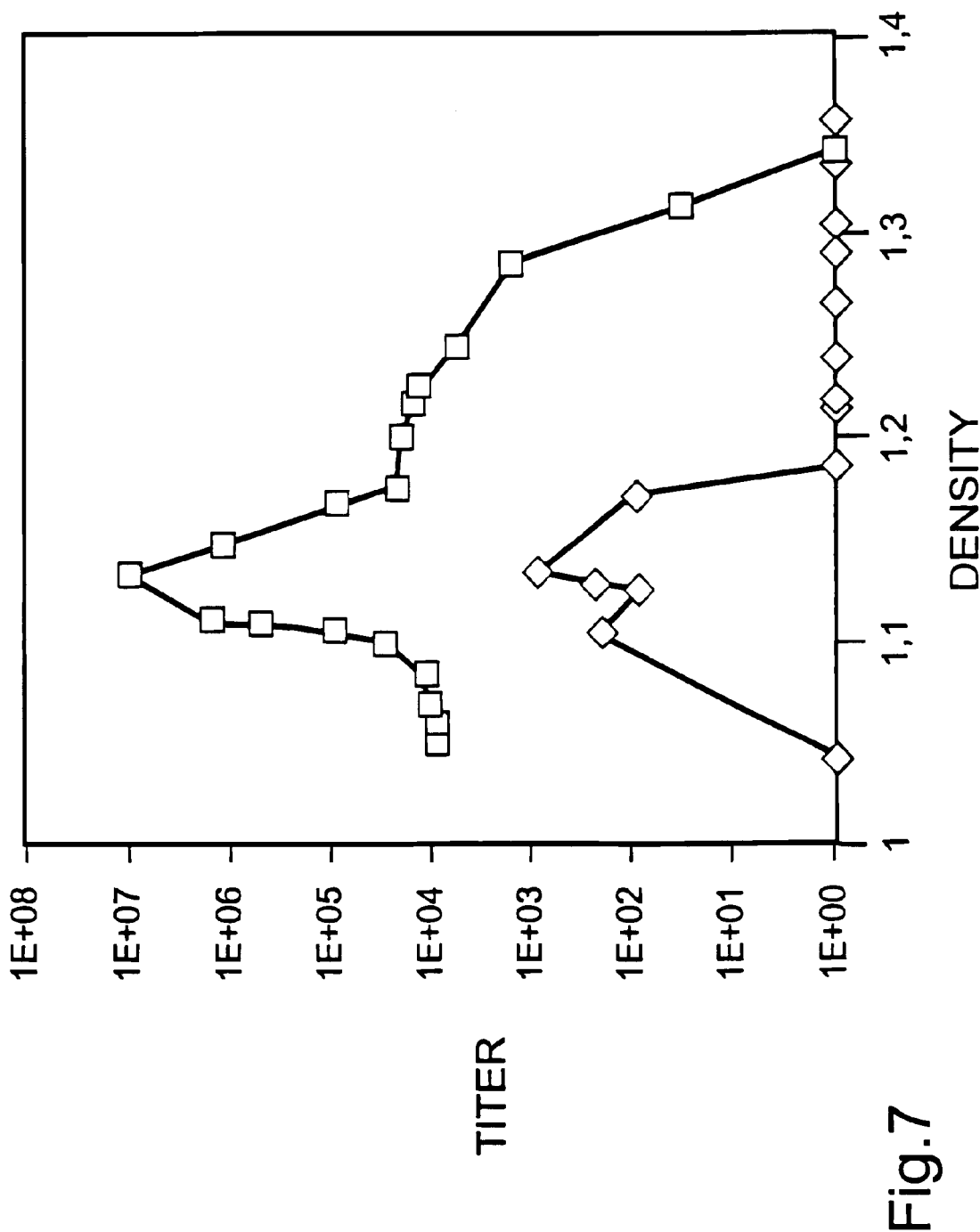

MLV (LCMV) pseudotypes retain infectiousness during concentration by gradient ultracentrifugation: amphotrophic retroviruses lose infectiousness after centrifugation, in all probability due to the lability of the retroviral envelope glycoproteins (V. Moenning et al., Virology 61 (1974) 100–111). A test was carried out to find out whether the MLV(LCMV) pseudotypes are more stable. TELCeB were infected with LCMV or with amphotrophic helper virus. Titres of the viral vector in the direct supernatant were $5 \times 10^4$ LTU per ml for both pseudotypes. Viruses were pelleted from 60 ml supernatant and purified by centrifugation through a 0–40% Urografin gradient. The pseudotype titres (in LTU per ml) are shown in FIG. 7. The total expected yield of $3 \times 10^6$ LTU for the LCMV pseudotype was obtained in full, in contrast to $1 \times 10^3$ LTU for the amphotrophic virus. The reverse transcriptase activity in the bands showed that the amount of virus particles which was obtained from the gradient was similar for both pseudotypes (data not shown). Compared with the amphotrophic virions, the infectiousness of MLV(LCMV) pseudotypes during ultracentrifugation was, however, more stable at least by a factor of 1000.

LCMV pseudotypes were also stable during storage at 4° C. Within the period of observation of three days, the loss of titre was twice as low (compared with the starting titre of MLV (LCMV)). A deep freeze cycle (−80° C.) and thawing led to a loss of pseudotype titre, which was twice as low.

Example 2

Gag and Pol Gene Products are Required for Packaging Retroviral RNA into the LCMV Glycoprotein Pseudotypes A test was carried out to find out whether the retroviral RNA alone could be packaged into the LCMV or whether gag and pol gene products were required. 293 cells and 293gp2 cells, the latter containing gag and pol of MLV, were transfected with a retroviral vector based on MLV which contained the neo gene (MP1N), and cell lines which contained the stably integrated vector were prepared by G418 selection (293MP1N and 293gp2MP1N; a clone of the cell line 293gp2MP1N denoted SF23 was deposited at the Deutsche Sammlung von Mikroorganismen und Zellkulturen (German Collection of Microorganisms and Cell Cultures; DSMZ), Mascheroder Weg 1b, 38124 Braunschweig, Germany under the access number DSM ACC2374 according to the Budapest Treaty). These cells (mass cultures) were then infected either with an amphotrophic helper capable of replication or with the LCMV wild-type virus. The results are shown in Tab. 2. Infectious vector which transferred neomycin resistance was obtained from both cell lines after infection with the amphotrophic helper. After infection with LCMV, however, only 293gpMP1N produced infectious retroviral particles whereas 293MP1N, which expressed no retroviral Gag or Pol, did not. Retroviral genomic RNA was not, therefore, packaged into infectious virions by LCMV in the absence of gag and pol gene products.

Tab. 2: gag and/or pol gene products are essential for the rescue of a retroviral vector by LCMV

| Cell line | Vector titre* released after infection with | | |
|---|---|---|---|
| | LCMV | amphotrophic helper | (control) |
| 293MP1N | 0 | $1 \cdot 10^4$ | 0 |
| 293gp2MP1N | $2 \cdot 10^3$ | $6 \cdot 10^4$ | 0 |

*Vector titres are expressed in G418-resistant cell colonies which were obtained after inoculation of Sc-1 with the viral supernatants (G418 transfer units/ml).

Example 3
Infection of 293gpMP1N with LCMV and Stable Gene Transfer to L929—Detection by Southern Blotting MLV (LCMV) pseudotypes mediate transfer and stable integration of the retroviral vector genome: the transfer of G418 resistance by the retroviral LCMV pseudotype showed that the marker gene had been stably integrated into the host genome. In order to verify that MLV (LCMV) pseudotypes are able to mediate stable transduction with integration of the transgene into the target cell genome, a retroviral vector which contained the neomycin resistance gene (neo) was rescued by LCMV infection of the env-negative packaging cell line 293gp2MP1N. The titres were measured by transfer of G418 resistance to Sc-1 cells and lay between $1 \times 10^3$ and $1 \times 10^4$ G418 transfer units (GTU) per ml. Resistant cell clones appeared after eight days' selection and were cultivated for a further three weeks. The DNA of 12 G418-resistant clones underwent a Southern blot analysis after restriction with HindIII, a single-cut enzyme, using a Neo probe. One copy of the integrated retroviral vector genome per cell was detected in 10 clones, and two copies in the other two clones (data not shown). Transduction with the MLV(LCMV) pseudotype therefore led to stable integration of the transgene.

Example 4
Expression of LCMV Glycoprotein (LCMV-GP) in TeLCeB-L(Arm)
Material and Methods The preparation of the env-negative packaging line TeLCeb, which contains gag and pol of MLV as well as a retroviral vector genome with LacZ as the transgene, has already been described in detail (F. L. Cosset et al., J. Virol. 69 (1995) 7430–7436). The titration of the vector supernatants was carried out on 293-cells by X-Gal staining as has already been described (G. R. McGregor, Methods Mol. Biol. 7 (1989) 1–19). The cells were cultivated in DMEM with 10% FCS. The L(Arm) strain of LCMV is produced after several passages of LCMV in L929 cells (M. Bruns et al., Virology 177 (1990) 615–624). LCMV nucleoprotein (LCMV-NP) of L(Arm) was detected by immunofluorescence staining of the cells on slides with a polyclonal anti-LCMV rabbit serum. This standard method has already been described in detail (M. Bruns et al., Virology 177 (1990) 615–624). For the expression of LCMV-GP, the gp gene was cloned into the episomal EBV vector pCep4 (Invitrogen) which carries a hygromycin resistance gene.

Results

In the experiments for pseudotyping by the sole expression of LCMV-GP in env-negative retroviral packaging lines, a higher GP-mRNA expression was obtained with the expression plasmids than with LCM wild virus infection (FIG. 4). This result shows that the simultaneous presence of at least one further LCMV gene product in addition to the LCMV glycoprotein brings about an increase in glycoprotein production and promotes the formation of pseudotypes. In order to substantiate this conclusion directly, the ectopically expressed (from a plasmid) LCMV-GP was complemented with the LCMV proteins of the L(ARM) strain of LCMV. This defective strain lacks the functional glycoprotein and it therefore forms no plaques, is not pathogenic for mice and proliferates within a cell culture only over several weeks (whereas LCM wild virus does so within 24 hours). All the other gene products of L(ARM) (NP, L and Z) exhibit no detectable defects.

TeLCeb were infected with L(Arm)-containing cell culture supernatant and passages were then run for 5 weeks. Experience has shown that this is the time that the defective virus requires to infect all the cells of a culture. The complete infection of all the cells was verified by immunofluorescence staining with an anti-LCMV serum. TeLCeb-L(Arm) were transfected with pCep-GP by electroporation (electroporator from Dr. Fischer, Heidelberg) and selected for 2 weeks with hygromycin. As a control, cells were transfected with pCep4 (without GP gene). In TeLCeb-L (Arm) which were transfected with pcep-GP, pseudotypes which transferred lacZ to 293-cells were produced after selection. The titre lay between $10^2$ and $10^3$/ml. This result shows clearly that the LCMV-GP in the expression plasmid described was functional and is able to pseudotype retroviral vectors.

Figure 5:
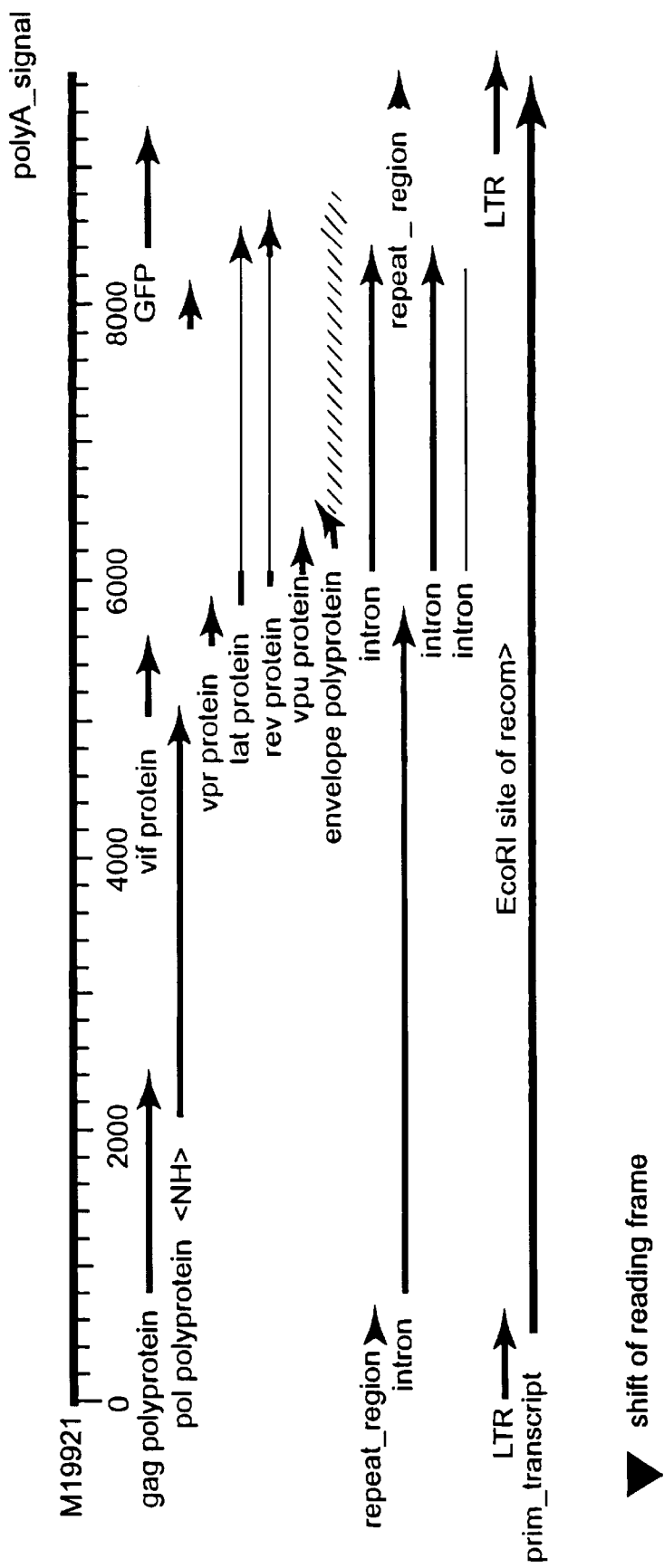

Example 5
Pseudotypina of an HIV Vector which Expresses the Green Fluorescent Protein (GFP)
Material and Methods The lentiviral vector HIV-GFP is derived from the infectious DNA clone pNL4-3 of HIV and has already been described in detail (FIG. 5) (R. I. Connor et al., virology 206 (1995) 935–944). At the beginning of env, the NdeI cleavage site was filled in and religated as a result of which the reading frame shifts and no functional envelope protein is synthesised. Further, instead of nev, the gene for the green fluorescent protein (GFP) was cloned. The titre of the LCMV-WE strain used was determined by a plaque assay on L929 which has already been described in detail (F. Lehmann-Grube et al., J. Gen. Virol. 37 (1977) 85–92). The calcium phosphate transfections were carried out on 293 with a standard protocol (Maniatis, et al., Molecular cloning, a laboratory manual; Cold Spring Harbor Laboratory Press, 1982).

Results 293-cells were infected with an m.o.i. of 0.1 of the LCMV-WE strain. After one hour transfection was carried out with HIV-GFP and after two days the supernatants were harvested and transferred to 293-cells. The titre was determined by the GFP expression in the 293-target cells by means of immunofluorescence and lay between $10^2$ and $10^3$ per ml. After transfection with HIV-GFP alone (without prior infection with LCMV), no production of infectious vector particles occurred, as expected.

Example 6
Investigation of Cell Tropism

MLV(LCMV) pseudotypes infect various human cell lines: the tropism of MLV(LCMV) pseudotypes was analysed. Several human cell lines derived from cells which are attractive targets for gene therapy such as haematopoietic progenitor cells and hepatocytes were analysed. The transfer efficiency relative to mouse fibroblasts is shown in Tab. 3. All the cell lines analysed were susceptible to MLV(LCMV)

pseudotypes. Even hamster cells which are normally resistant to transduction with MLV-derived vectors could be transduced efficiently with the MLV(LCMV) pseudotypes.

TABLE 3

Host spectrum of MLV(LCMV) pseudotypes

| Cell line | Origin | Transduction efficiency |
|---|---|---|
| 293 | epithelium, human | +++ |
| K-562 | myeloid progenitor cells, human | +++ |
| TF-1 | myeloid progenitor cells, human | + |
| HUH-1 | hepatoma, human | ++ |
| Jurkat | lymphocyte, human | ++* |
| Sc-1 | fibroblast, mouse | +++ |
| CHO | epithelium, hamster | +++ |
| Cf2Th | thymus stroma, dog | +++ |

*The pseudotypes were prepared using LCMV passed on (adapted to) lymphocytes. Pseudotypes of LCMV passaged on fibroblasts do not transduce lymphocytes.

BRIEF DESCRIPTION OF THE FIGURES

FIG. 1: Retroviral packaging lines

The retroviral genes gag, pol and env are stably integrated into the genome of the retroviral packaging lines. Env is usually expressed separately from gag and pol. Moreover, the vector genome is expressed with the transgene and regulatory cis elements (1). The genomic RNA of the vector contains a packaging signal which was deleted on the gag, pol and env genes. In the cytoplasm, the retroviral proteins therefore package the vector genome selectively (2). A complete retroviral nucleocapsid forms (3) and is released by budding on the cell membrane (4). In so doing, retroviral envelope protein or, in the case of the pseudotypes, a foreign viral envelope protein is carried along. Outside the cell, the virus matures by proteolytic cleavage of the retroviral precursor proteins in the nucleocapsid.

FIG. 2: The genomic RNA of the LCM virus. The genome of LCMV is composed of 2 ambisense RNA molecules each with two open reading frames. The 4 genes and their orientation are given.

FIG. 3: The production of MLV(LCMV) pseudotypes. Packaging lines which produce no viral envelope proteins also release no infectious retroviral vectors. If such an env-negative packaging line is infected with LCM virus, the retroviruses can insert the LCMV glycoprotein into their coat. So-called pseudotypes are produced. Moreover, LCM wild virus is released during LCMV replication.

FIG. 4: Discrepancy between high mRNA and low protein concentration in the case of ectopic GP-C expression. 293-cells were transfected with different expression constructs for LCMV glycoprotein (Ef-1 alpha promoter, alphavirus vector from Invitrogen, CMV promoter+beta globin intron, see above: preferred expression cassettes). After 2 days, the gp-mRNA concentration in the Northern blot and the GP-1/GP-2 protein quantities on the cells were measured in parallel by continuous flow cytometry. 293-cells that were infected with LCMV wild-type were used as a control. In the case of wild virus infection, the GP-1/GP-2 protein expression was 2–3 log stages above the negative control, with a relatively weak mRNA band in the Northern blot (upper band LCMV-genomic RNA, lower band gp-mRNA). In the case of ectopic expression, the protein concentration for GP-1/GP-2 was only at most one log stage above the negative control despite a higher mRNA concentration than with wild virus infection.

FIG. 5: HIV-GFP. The infectious DNA clone of HIV pNL4-3 was cut at the beginning of the env gene with NdeI, the cleavage site was filled in and religated(s). As a result, the reading frame shifts and no functional env gene product is produced. Instead of nef, the gene for the "green fluorescent protein" (GFP) was cloned between XhoI and BamHI.

FIG. 6: Rescue of the retroviral vector MFGlnsLacZ by LCMV.

The retroviral env-negative packaging cell line TELCeB was infected by LCMV with an m.o.i. of 0.01. Between day 1 and 7 after infection, the supernatants were replaced daily and the titres of the LCMV wild-type and LacZ vector were determined by a plaque assay on L-929 and by LacZ gene transfer to Sc-1. In addition, a part of the LCMV-infected TELCeB cells were stained daily with a monoclonal antibody directed against the LCMV glycoprotein GP-1 and analysed by continuous flow cytometry. The mean fluorescence is shown. ○-○ LCMV wild-type titre; □-□LacZ transfer units; Δ-Δ mean fluorescence of the LCMV glycoprotein GP expression.

FIG. 7: MLV(LCMV) pseudotypes retain their infectiousness after ultracentrifugation.

TELCeB were infected with LCMV or amphotrophic helper virus. The supernatants were harvested and frozen. The MLV(LCMV) and amphotrophic pseudotype titres were determined. Equal quantities of the infectious virus were pelleted by ultracentrifugation and then underwent purification on a 0%–40% Urografin gradient. Vector titres and densities were determined in each fraction. ○-○ amphotrophic pseudotype; □-□ MLV(LCMV) pseudotype.

What is claimed is:

1. A retroviral packaging cell, which comprises gag and pol genes of a retrovirus and a nucleic acid sequence coding for a glycoprotein having the amino acid sequence of SEQ ID NO:26 which is operably linked to a promoter, wherein the gag and pol genes and said glycoprotein are expressed in said retroviral packaging cell.

2. The retroviral packaging cell according to claim 1, wherein the nucleic acid sequence is the nucleic acid sequence shown in SEQ ID NO:25.

3. The retroviral packaging cell according to claim 1, which further comprises at least one gene from the group consisting of an env gene of a retrovirus, retroviral regulatory genes, the gene np of lymphocytic choriomeningitis virus (LCMV) coding for a nucleoprotein, the gene l of LCMV coding for RNA polymerase, and the gene z of LCMV.

4. The retroviral packaging cell according to claim 1, wherein the retrovirus is an MLV-related virus or a lentivirus.

5. The retroviral packaging cell according to claim 4, wherein the retrovirus is derived from MLV, HIV, SIV or FIV.

6. A retroviral pseudotype vector particle, obtainable by cultivating the packaging cell of claim 5, wherein the particle comprises the glycoprotein having the amino acid sequence of SEQ ID NO:26.

7. The retroviral packaging cell according to claim 1, further comprising a recombinant retroviral vector which comprises one or more transgenes selected from the group consisting of marker genes and genes encoding therapeutic proteins, wherein the retroviral packaging cell produces recombinant retroviral virions.

8. The retroviral packaging cell according to claim 7, wherein the marker gene is neo, lacZ or EGFP.

9. The retroviral packaging cell according to claim 7, wherein said therapeutic proteins are selected from the group of a herpes simplex virus thymidine kinase (HSV-tk), a cytosine deaminase (CD), and a cytokine.

10. The retroviral packaging cell according to claim 7, wherein said therapeutic proteins are mdr-1 proteins.

11. A process for the preparation of a retroviral packaging cell according to claim 7, comprising the step of contacting a retroviral packaging cell with a LCMV under suitable conditions, wherein said retroviral packaging cell comprises gag and pol genes of a retrovirus and a recombinant retroviral vector which comprises one or more transgenes selected from the group consisting of marker genes and genes encoding therapeutic proteins, and wherein said LCMV comprises a nucleotide sequence which encodes a glycoprotein having the amino acid sequence shown in SEQ ID NO:26.

12. The process according to claim 11, wherein the nucleotide sequence is the nucleic acid sequence shown in SEQ ID NO:25.

13. The process according to claim 11, wherein said retroviral packaging cell further comprises an env gene of a retrovirus, and wherein said env gene encodes an Env protein which mediates specific binding to a target cell.

14. A process for the preparation of a retroviral packaging cell according to claim 7, comprising the step of contacting a retroviral packaging cell with a plasmid vector expressing a glycoprotein having the amino acid sequence shown in SEQ ID NO:26 under suitable conditions, wherein said retroviral packaging cell comprises gag and pol genes of a retrovirus and a recombinant retroviral vector which comprises one or more transaenes selected from the group consisting of marker genes and genes encoding therapeutic proteins, and wherein said plasmid vector optionally further contains one or more genes from the group consisting of np, l and z of LCMV.

15. The process according to claim 14, wherein the nucleic acid sequence is the nucleic acid sequence shown in SEQ ID NO:25.

16. The process according to claim 14, wherein said retroviral packaging cell further comprises an env gene of a retrovirus, and wherein said env gene encodes an Env protein which mediates specific binding to a target cell.

17. A process for the preparation of retroviral pseudotype virions, comprising the steps of performing the process according to claim 11, and cultivating the resulting packaging cells under conditions which are suitable for the production of retroviral pseudotype virions.

18. A process for the preparation of retroviral pseudotype virions, comprising the steps of performing the process according to claim 14, and cultivating the resulting packaging cells under conditions which are suitable for the production of retroviral pseudotype virions.

19. A method for in vitro infection of cells and for the expression of a transgene in said cells, said method comprising contacting the cells with the retroviral packaging cell of claim 7 or with cell culture supernatants of said retroviral packaging cell, wherein the contacting is performed under conditions which allow infection of the cells, and wherein the infected cells are cultured under conditions which allow expression of the transgene.

20. The process according to claim 11, wherein said retroviral packaging cell further comprises at least one of an env gene of a retrovirus, and a retroviral regulatory gene.

21. The process according to claim 14, wherein said retroviral packaging cell further comprises at least one of an env gene of a retrovirus, and a retroviral regulatory gene.

22. A retroviral packaging cell according to claim 1, which is obtainable by transfection of a retroviral packaging cell with an expression plasmid which comprises a nucleic acid sequence coding for a glycoprotein having the sequence shown in SEQ ID NO:26 and which optionally further comprises a np gene of LCMV, a l gene of LCMV, or a z gene of LCMV.

23. The retroviral packaging cell according to claim 22, wherein the nucleic acid sequence is the nucleic acid sequence shown in SEQ ID NO:25.

24. The retroviral packaging cell according to claim 1, which further comprises an env gene of a retrovirus coding for an Env protein which mediates specific binding to a target cell.

25. A pseudotyped virion, which is produced by the packaging cell according to claim 1, wherein the virion comprises the glycoprotein having the amino acid sequence of SEQ ID NO:26.

26. A retroviral packaging cell, wherein the cell expresses pseudotyped virions which comprise a glycoprotein having the amino acid sequence shown in SEQ ID NO:26 inserted in the coat of said virions.

27. An isolated lymphocytic choriomeningitis virus, which contains a nucleic acid sequence which encodes a glycoprotein having the amino acid sequence shown in SEQ ID NO:26.

28. The isolated lymphocytic choriomeningitis virus according to claim 27, wherein the nucleic acid sequence is the nucleic acid sequence shown in SEQ ID NO:25.

29. An isolated polynucleotide having the nucleic acid sequence shown in SEQ ID NO:25.

30. An isolated protein having the amino acid sequence shown in SEQ ID NO:26.

31. An isolated polynucleotide having the nucleic acid sequence which encodes a glycoprotein having the amino acid sequence shown in SEQ ID NO:26.

* * * * *

SEQUENCE LISTING

```
<160> NUMBER OF SEQ ID NOS:  26

<210> SEQ ID NO 1
<211> LENGTH: 3375
<212> TYPE: DNA
<213> ORGANISM: Lymphocytic choriomeningitis virus

<400> SEQUENCE: 1
cgcaccgggg atcctaggct ttttggattg cgctttcctt taggacaact gggtgctgga     60
ttctatccag taaaaggatg ggtcagattg tgacaatgtt tgaggctttg cctcacatca    120
```

-continued

| | |
|---|---|
| ttgatgaggt catcaacatt gtcattattg tgctcattat aatcacgagc atcaaagctg | 180 |
| tgtacaattt cgccacctgt gggatattag cactggtcag cttccttttt ctggctggta | 240 |
| ggtcctgtgg catgtacggc cttaatggtc ccgatatcta taaagggggtt taccagttca | 300 |
| aatcagtgga gtttgatatg tctcacttaa atctgacgat gcccaatgcg tgctcagtca | 360 |
| acaactctca tcactacatc agtatgggaa gctctggact ggagccaact ttcaccaacg | 420 |
| actccatcct taatcacaac ttctgcaact taacctccgc tctcaacaaa agtcttttg | 480 |
| accatacact catgagtata gtctcgagtc tacacctcag tatcagaggg aattccaact | 540 |
| acaaagcagt gtcttgtgat tttaacaatg gcatcaccat tcaatacaac ttgtcatctt | 600 |
| cggacccaca gagcgccatg agccagtgta ggactttcag aggtagagtc ttggacatgt | 660 |
| ttagaactgc ctttggagga agtacatga aagtggctg gggctggaca ggttcagatg | 720 |
| gcaagaccac ttggtgcagc caaacaagct atcagtacct aatcatacaa acaggactt | 780 |
| gggaaaacca ctgtagatat gcaggccctt tgggatgtc tagaatcctc tttgctcagg | 840 |
| aaaagacaaa gtttctcact aggagacttt caggcacatt cacctggacc ctgtcagact | 900 |
| cctcaggagt agaaaatcca ggtggttatt gcctgaccaa atggatgatc cttgctgcag | 960 |
| agctcaaatg ttttgggaat acagctgttg caaaatgtaa tgtcaatcat gatgaagagt | 1020 |
| tctgtgacat gctacgacta attgattaca acaaggctgc cctgagtaag ttcaagcaag | 1080 |
| atgtagagtc tgccttgcat gtattcaaaa caacattaaa ttctctgatt ccgatcagc | 1140 |
| tgttgatgag gaatcatcta agagatctaa tgggggtacc atactgtaat tactcaaagt | 1200 |
| tctggtatct ggaacatgct aagactggtg agactagtgt acccaagtgt tggcttgtca | 1260 |
| ctaatggctc ctacttgaat gagacccatt ttagtgatca aatcgaacaa gaagcagata | 1320 |
| acatgatcac agagatgttg aggaaggact acataaaaag acaagggagt actccttttag | 1380 |
| ccttaatgga tcttttgatg ttttcaacat cagcatactt gatcagcatc tttctgcatt | 1440 |
| ttgtgaggat accaacacat agacacataa agggcggttc atgtccaaag ccacatcgct | 1500 |
| tgaccaacaa ggggatctgt agttgtggtg cattcaaggt gcctggtgta aaaactatct | 1560 |
| ggaaaagacg ctgatcagca gcgcctccct gactctccac ctcgaaagag gtggagagtc | 1620 |
| agggaggccc agcgggtctt agagtgtcac aacattgggt cctctgaaga tcaaatcatg | 1680 |
| tggcaggatg ttgtgaacgg tctttagatc agggagtctt gccttggaag cactctcaaa | 1740 |
| gatgatgcag tccatgagtg cacagtgtgg ggtgatttct ttcttctttt tgtctctcac | 1800 |
| taccccagtg tgcattttgc atagccagcc atatttgtcc cacactttat cttcatattc | 1860 |
| tcttgaggcc tccttagtca tctcaacatc aatgagtttt atgtcccttc tattctgtga | 1920 |
| gtccagaagc tttctgatgt catcagaacc ttgacagctc aagaccatcc cttgtgggag | 1980 |
| agcacctata actgatgagg tcagcccagc ctgtgcattg aagaggtcag caagatccat | 2040 |
| gccgtgtgaa tacttggagt cctgcttgaa ttgcttctgg tccgtaggtt ctctgtaaaa | 2100 |
| atgtatgaat tgcccatttt gtggttgaaa tattgctatc tccactggat cattgaacct | 2160 |
| gccttcaatg tcaatccatg tgggagcatt gggatcaatc cctcccatca agtcttttcaa | 2220 |
| cagcattgtt tgactgtaac tcaagcccac ctgaggtggg cctgctgctc caggcactgg | 2280 |
| cctagatgag ttggccacaa gtttttcatt tgtgagatca attgtcgtgt ctcccatgc | 2340 |
| tctccccaca actgacgttc tacaggctat gtatggccat ccttcacctg aaagacagac | 2400 |
| tttataaagg atgttttcat aaggatttct atccccaact tgatctgaga caaacatgtt | 2460 |
| gagtttcttc ttggccccaa ggactgcttt taggagatcc tcactattgc ttggtttgat | 2520 |

-continued

```
caaatagat tccagcatgt tccctccatg tagcagagct gcccccgctt tcacagccgc    2580
accaagactg aaattataac cagagatatt gatactagat tgctgttcag taatgacccc    2640
cagaactggg tgtttatctt ttagcctttc taggtcactg agattcgggt atttgactgt    2700
gtaaagtaag ccaaggtctg tgagtgcctg cacaacatca ttgagtgggg tctgtgactg    2760
ttttgccatg caagccattg tcaggcttgg cattgtgccg aactgattgt tcagaagtga    2820
tgagtccttc acatcccaaa cccttactac accacttgca ccctgctgag gtcttctcat    2880
cccaaccatt tgcagtattt gggatctctg atcaagttgt tgtgctgtca aatttcccat    2940
gtagactcca gaagcttgag gcctctcagt tctcataatt ttggccttca gcttctcaag    3000
atcagctgca agggtcatca attcctctgc actaagtctt cccactttca gaacattttt    3060
ctttgatgta gacttcggat caacaagaga atgcacagtc tggttaagac tcctgagtct    3120
ctgcaagtct ttatcgtccc tcctttcctt tctcatgatc ctctgaacgt tgctgacttc    3180
agaaaagtcc aacccattta gaagactggt tgcgtccttg atgacggcag cctttacatc    3240
tgatgtaaaa ccctgcaact ccctcctcaa cgcctgtgtc cactgaaagc ttttgacttc    3300
tttggacaaa gacattttgt cacacaatga atttccaaat aaaagcgcaa tcaaatgcct    3360
aggatccact gtgcg                                                    3375
```

<210> SEQ ID NO 2
<211> LENGTH: 498
<212> TYPE: PRT
<213> ORGANISM: Lymphocytic choriomeningitis virus
<220> FEATURE:
<223> OTHER INFORMATION: S protein

<400> SEQUENCE: 2

```
Met Gly Gln Ile Val Thr Met Phe Glu Ala Leu Pro His Ile Ile Asp
  1               5                  10                  15

Glu Val Ile Asn Ile Val Ile Ile Val Leu Ile Ile Ile Thr Ser Ile
             20                  25                  30

Lys Ala Val Tyr Asn Phe Ala Thr Cys Gly Ile Leu Ala Leu Val Ser
         35                  40                  45

Phe Leu Phe Leu Ala Gly Arg Ser Cys Gly Met Tyr Gly Leu Asn Gly
     50                  55                  60

Pro Asp Ile Tyr Lys Gly Val Tyr Gln Phe Lys Ser Val Glu Phe Asp
 65                  70                  75                  80

Met Ser His Leu Asn Leu Thr Met Pro Asn Ala Cys Ser Val Asn Asn
                 85                  90                  95

Ser His His Tyr Ile Ser Met Gly Ser Ser Gly Leu Glu Pro Thr Phe
            100                 105                 110

Thr Asn Asp Ser Ile Leu Asn His Asn Phe Cys Asn Leu Thr Ser Ala
        115                 120                 125

Leu Asn Lys Lys Ser Phe Asp His Thr Leu Met Ser Ile Val Ser Ser
    130                 135                 140

Leu His Leu Ser Ile Arg Gly Asn Ser Asn Tyr Lys Ala Val Ser Cys
145                 150                 155                 160

Asp Phe Asn Asn Gly Ile Thr Ile Gln Tyr Asn Leu Ser Ser Ser Asp
                165                 170                 175

Pro Gln Ser Ala Met Ser Gln Cys Arg Thr Phe Arg Gly Arg Val Leu
            180                 185                 190

Asp Met Phe Arg Thr Ala Phe Gly Gly Lys Tyr Met Arg Ser Gly Trp
        195                 200                 205
```

```
Gly Trp Thr Gly Ser Asp Gly Lys Thr Thr Trp Cys Ser Gln Thr Ser
    210                 215                 220
Tyr Gln Tyr Leu Ile Ile Gln Asn Arg Thr Trp Glu Asn His Cys Arg
225                 230                 235                 240
Tyr Ala Gly Pro Phe Gly Met Ser Arg Ile Leu Phe Ala Gln Glu Lys
                245                 250                 255
Thr Lys Phe Leu Thr Arg Arg Leu Ser Gly Thr Phe Thr Trp Thr Leu
            260                 265                 270
Ser Asp Ser Ser Val Glu Asn Pro Gly Gly Tyr Cys Leu Thr Lys
        275                 280                 285
Trp Met Ile Leu Ala Ala Glu Leu Lys Cys Phe Gly Asn Thr Ala Val
    290                 295                 300
Ala Lys Cys Asn Val Asn His Asp Glu Glu Phe Cys Asp Met Leu Arg
305                 310                 315                 320
Leu Ile Asp Tyr Asn Lys Ala Ala Leu Ser Lys Phe Lys Gln Asp Val
                325                 330                 335
Glu Ser Ala Leu His Val Phe Lys Thr Thr Leu Asn Ser Leu Ile Ser
            340                 345                 350
Asp Gln Leu Leu Met Arg Asn His Leu Arg Asp Leu Met Gly Val Pro
        355                 360                 365
Tyr Cys Asn Tyr Ser Lys Phe Trp Tyr Leu Glu His Ala Lys Thr Gly
    370                 375                 380
Glu Thr Ser Val Pro Lys Cys Trp Leu Val Thr Asn Gly Ser Tyr Leu
385                 390                 395                 400
Asn Glu Thr His Phe Ser Asp Gln Ile Glu Gln Glu Ala Asp Asn Met
                405                 410                 415
Ile Thr Glu Met Leu Arg Lys Asp Tyr Ile Lys Arg Gln Gly Ser Thr
            420                 425                 430
Pro Leu Ala Leu Met Asp Leu Leu Met Phe Ser Thr Ser Ala Tyr Leu
        435                 440                 445
Ile Ser Ile Phe Leu His Phe Val Arg Ile Pro Thr His Arg His Ile
    450                 455                 460
Lys Gly Gly Ser Cys Pro Lys Pro His Arg Leu Thr Asn Lys Gly Ile
465                 470                 475                 480
Cys Ser Cys Gly Ala Phe Lys Val Pro Gly Val Lys Thr Ile Trp Lys
                485                 490                 495
Arg Arg

<210> SEQ ID NO 3
<211> LENGTH: 3376
<212> TYPE: DNA
<213> ORGANISM: Lymphocytic choriomeningitis virus

<400> SEQUENCE: 3
cgcaccgggg atcctaggct ttttggattg cgctttcctc tagatcaact gggtgtcagg      60
ccctatccta cagaaggatg ggtcagattg tgacaatgtt tgaggctctg cctcacatca    120
tcgatgaggt gatcaacatt gtcattattg tgcttatcgt gatcacgggt atcaaggctg    180
tctacaattt tgccacctgt gggatattcg cattgatcag tttcctactt ctggctggca    240
ggtcctgtgg catgtacggc cttaagggac ccgacattta caaggagtt taccaattta    300
agtcagtgga gtttgatatg tcacatctga acctgaccat gcccaacgca tgttcagcca    360
acaactccca ccattacatc agtatgggga cttctggact agaattgacc ttcaccaatg    420
```

```
attccatcat cagtcacaac ttttgcaatc tgacctctgc cttcaacaaa aagacctttg    480
accacacact catgagtata gtttcgagcc tacacctcag tatcagaggg aactccaact    540
ataaggcagt atcctgcgac ttcaacaatg cataaccat ccaatacaac ttgacattct     600
cagatcgaca aagtgctcag agccagtgta gaaccttcag aggtagagtc ctagatatgt    660
ttagaactgc cttcgggggg aaatacatga ggagtggctg gggctggaca ggctcagatg    720
gcaagaccac ctggtgtagc cagacgagtt accaataccct gattatacaa aatagaacct   780
gggaaaacca ctgcacatat gcaggtcctt ttgggatgtc caggattctc ctttcccaag    840
agaagactaa gttcttcact aggagactag cgggcacatt cacctggact tgtcagact    900 cttcaggggt ggagaatcca ggtggttatt gcctgaccaa atggatgatt cttgctgcag    960
agcttaagtg tttcgggaac acagcagttg cgaaatgcaa tgtaaatcat gatgccgaat   1020
tctgtgacat gctgcgacta attgactaca acaaggctgc tttgagtaag ttcaaagagg   1080
acgtagaatc tgccttgcac ttattcaaaa caacagtgaa ttctttgatt tcagatcaac   1140
tactgatgag gaaccacttg agagatctga tgggggtgcc atattgcaat tactcaaagt   1200
tttggtacct agaacatgca aagaccggcg aaactagtgt ccccaagtgc tggcttgtca   1260
ccaatggttc ttacttaaat gagacccact tcagtgatca aatcgaacag gaagccgata   1320
acatgattac agagatgttg aggaaggatt acataaagag gcaggggagt accccctag    1380 cattgatgga ccttctgatg ttttccacat ctgcatatct agtcagcatc ttcctgcacc   1440
ttgtcaaaat accaacacac aggcacataa aaggtggctc atgtccaaag ccacaccgat   1500
taaccaacaa aggaatttgt agttgtggtg catttaaggt gcctggtgta aaaaccgtct   1560
ggaaaagacg ctgaagaaca gcgcctccct gactctccac ctcgaaagag gtggagagtc   1620
agggaggccc agagggtctt agagtgtcac aacatttggg cctctaaaaa ttaggtcatg   1680
tggcagaatg ttgtgaacag ttttcagatc tgggagcctt gctttggagg cgctttcaaa   1740
aatgatgcag tccatgagtg cacagtgcgg ggtgatctct ttcttctttt tgtcccttac   1800
tattccagta tgcatcttac acaaccagcc atatttgtcc cacactttgt cttcatactc   1860
cctcgaagct tccctggtca tttcaacatc gataagctta atgtccttcc tattctgtga   1920
gtccagaagc tttctgatgt catcggagcc ttgacagctt agaaccatcc cctgcggaag   1980
agcacctata actgacgagg tcaacccggg ttgcgcattg aagaggtcgg caagatccat   2040
gccgtgtgag tacttggaat cttgcttgaa ttgtttttga tcaacgggtt ccctgtaaaa   2100
gtgtatgaac tgcccgttct gtggttggaa aattgctatt tccactggat cattaaatct   2160
accctcaatg tcaatccatg taggagcgtt ggggtcaatt cctcccatga ggtcttttaa   2220
aagcattgtc tggctgtagc ttaagcccac ctgaggtgga cctgctgctc caggcgctgg   2280
cctgggtgaa ttgactgcag gtttctcgct tgtgagatca attgttgtgt tttcccatgc   2340
tctccccaca atcgatgttc tacaagctat gtatggccat ccttcacctg aaaggcaaac   2400
tttatagagg atgttttcat aagggttcct gtccccaact tggtctgaaa caaacatgtt   2460
gagttttctc ttggccccga gaactgcctt caagaggtcc tcgctgttgc ttggcttgat   2520
caaaattgac tctaacatgt tacccccatc aacagggct gccctgcct tcacggcagc     2580 accaagacta aagttatagc cagaaatgtt gatgctggac tgctgttcag tgatgacccc   2640
cagaactggg tgcttgtctt tcagcctttc aagatcatta agatttggat acttgactgt   2700
gtaaagcaag ccaaggtctg tgagcgcttg tacaacgtca ttgagcggag tctgtgactg   2760
tttggccata caagccatag ttagacttgg cattgtgcca aattgattgt tcaaaagtga   2820
```

-continued

```
tgagtctttc acatcccaaa ctcttaccac accacttgca ccctgctgag gctttctcat    2880
cccaactatc tgtaggatct gagatctttg gtctagttgc tgtgttgtta agttccccat    2940 atataccct gaagcctggg gcctttcaga cctcatgatc ttggccttca gcttctcaag    3000
gtcagccgca agagacatca gttcttctgc actgagcctc cccactttca aaacattctt    3060
ctttgatgtt gactttaaat ccacaagaga atgtacagtc tggttgagac ttctgagtct    3120
ctgtaggtct ttgtcatctc tcttttcctt cctcatgatc ctctgaacat tgctgacctc    3180
agagaagtcc aacccattca gaaggttggt tgcatcctta atgacagcag ccttcacatc    3240
tgatgtgaag ctctgcaatt ctcttctcaa tgcttgcgtc cattggaagc tcttaacttc    3300
cttagacaag gacatcttgt tgctcaatgg tttctcaaga caaatgcgca atcaaatgcc    3360
taggatccac tgtgcg                                                    3376
```

<210> SEQ ID NO 4
<211> LENGTH: 498
<212> TYPE: PRT
<213> ORGANISM: Lymphocytic choriomeningitis virus
<220> FEATURE:
<223> OTHER INFORMATION: envelope glycoprotein

<400> SEQUENCE: 4

```
Met Gly Gln Ile Val Thr Met Phe Glu Ala Leu Pro His Ile Ile Asp
  1               5                  10                  15

Glu Val Ile Asn Ile Val Ile Val Leu Ile Val Ile Thr Gly Ile
                 20                  25                  30

Lys Ala Val Tyr Asn Phe Ala Thr Cys Gly Ile Phe Ala Leu Ile Ser
         35                  40                  45

Phe Leu Leu Leu Ala Gly Arg Ser Cys Gly Met Tyr Gly Leu Lys Gly
     50                  55                  60

Pro Asp Ile Tyr Lys Gly Val Tyr Gln Phe Lys Ser Val Glu Phe Asp
 65                  70                  75                  80

Met Ser His Leu Asn Leu Thr Met Pro Asn Ala Cys Ser Ala Asn Asn
                 85                  90                  95

Ser His His Tyr Ile Ser Met Gly Thr Ser Gly Leu Glu Leu Thr Phe
                100                 105                 110

Thr Asn Asp Ser Ile Ile Ser His Asn Phe Cys Asn Leu Thr Ser Ala
            115                 120                 125

Phe Asn Lys Lys Thr Phe Asp His Thr Leu Met Ser Ile Val Ser Ser
        130                 135                 140

Leu His Leu Ser Ile Arg Gly Asn Ser Asn Tyr Lys Ala Val Ser Cys
145                 150                 155                 160

Asp Phe Asn Asn Gly Ile Thr Ile Gln Tyr Asn Leu Thr Phe Ser Asp
                165                 170                 175

Arg Gln Ser Ala Gln Ser Gln Cys Arg Thr Phe Arg Gly Arg Val Leu
            180                 185                 190

Asp Met Phe Arg Thr Ala Phe Gly Gly Lys Tyr Met Arg Ser Gly Trp
        195                 200                 205

Gly Trp Thr Gly Ser Asp Gly Lys Thr Thr Trp Cys Ser Gln Thr Ser
    210                 215                 220

Tyr Gln Tyr Leu Ile Ile Gln Asn Arg Thr Trp Glu Asn His Cys Thr
225                 230                 235                 240

Tyr Ala Gly Pro Phe Gly Met Ser Arg Ile Leu Leu Ser Gln Glu Lys
                245                 250                 255
```

```
Thr Lys Phe Phe Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
            275                 280                 285

Trp Met Ile Leu Ala Ala Glu Leu Lys Cys Phe Gly Asn Thr Ala Val
            290                 295                 300

Ala Lys Cys Asn Val Asn His Asp Ala Glu Phe Cys Asp Met Leu Arg
305                 310                 315                 320

Leu Ile Asp Tyr Asn Lys Ala Ala Leu Ser Lys Phe Lys Glu Asp Val
                325                 330                 335

Glu Ser Ala Leu His Leu Phe Lys Thr Thr Val Asn Ser Leu Ile Ser
            340                 345                 350

Asp Gln Leu Leu Met Arg Asn His Leu Arg Asp Leu Met Gly Val Pro
            355                 360                 365

Tyr Cys Asn Tyr Ser Lys Phe Trp Tyr Leu Glu His Ala Lys Thr Gly
            370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
            435                 440                 445

Val Ser Ile Phe Leu His Leu Val Lys Ile Pro Thr His Arg His Ile
450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Val Trp Lys
                485                 490                 495

Arg Arg

<210> SEQ ID NO 5
<211> LENGTH: 558
<212> TYPE: PRT
<213> ORGANISM: Lymphocytic choriomeningitis virus
<220> FEATURE:
<223> OTHER INFORMATION: nucleoprotein

<400> SEQUENCE: 5

Met Ser Leu Ser Lys Glu Val Lys Ser Phe Gln Trp Thr Gln Ala Leu
  1               5                  10                  15

Arg Arg Glu Leu Gln Ser Phe Thr Ser Asp Val Lys Ala Ala Val Ile
            20                  25                  30

Lys Asp Ala Thr Asn Leu Leu Asn Gly Leu Asp Phe Ser Glu Val Ser
            35                  40                  45

Asn Val Gln Arg Ile Met Arg Lys Glu Lys Arg Asp Asp Lys Asp Leu
        50                  55                  60

Gln Arg Leu Arg Ser Leu Asn Gln Thr Val His Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Ser Leu Ala Ala Asp Leu Glu Lys Leu Lys Ala Lys
            100                 105                 110

Ile Met Arg Ser Glu Arg Pro Gln Ala Ser Gly Val Tyr Met Gly Asn
```

-continued

```
            115                 120                 125
Leu Thr Thr Gln Gln Leu Asp Gln Arg Ser Gln Ile Leu Gln Ile Val
130                 135                 140

Gly Met Arg Lys Pro Gln Gln Gly Ala Ser Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Pro Leu Asn
                180                 185                 190

Asp Val Gln Ala Leu Thr Asp Leu Gly Leu Leu Tyr Thr Val Lys
                195                 200                 205

Tyr Pro Asn Leu Asn Asp Leu Glu Arg Leu Lys Asp Lys His Pro Val
210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
                260                 265                 270

Asp Leu Leu Lys Ala Val Leu Gly Ala Lys Arg Lys Leu Asn Met Phe
                275                 280                 285

Val Ser Asp Gln Val Gly Asp Arg Asn Pro Tyr Glu Asn Ile Leu Tyr
290                 295                 300

Lys Val Cys Leu Ser Gly Glu Gly Trp Pro Tyr Ile Ala Cys Arg Thr
305                 310                 315                 320

Ser Ile Val Gly Arg Ala Trp Glu Asn Thr Thr Ile Asp Leu Thr Ser
                325                 330                 335

Glu Lys Pro Ala Val Asn Ser Pro Arg Pro Ala Pro Gly Ala Ala Gly
                340                 345                 350

Pro Pro Gln Val Gly Leu Ser Tyr Ser Gln Thr Met Leu Leu Lys Asp
                355                 360                 365

Leu Met Gly Gly Ile Asp Pro Asn Ala Pro Thr Trp Ile Asp Ile Glu
                370                 375                 380

Gly Arg Phe Asn Asp Pro Val Glu Ile Ala Ile Phe Gln Pro Gln Asn
385                 390                 395                 400

Gly Gln Phe Ile His Phe Tyr Arg Glu Pro Val Asp Gln Lys Gln Phe
                405                 410                 415

Lys Gln Asp Ser Lys Tyr Ser His Gly Met Asp Leu Ala Asp Leu Phe
                420                 425                 430

Asn Ala Gln Pro Gly Leu Thr Ser Ser Val Ile Gly Ala Leu Pro Gln
                435                 440                 445

Gly Met Val Leu Ser Cys Gln Gly Ser Asp Asp Ile Arg Lys Leu Leu
450                 455                 460

Asp Ser Gln Asn Arg Lys Asp Ile Lys Leu Ile Asp Val Glu Met Thr
465                 470                 475                 480

Arg Glu Ala Ser Arg Glu Tyr Glu Asp Lys Val Trp Asp Lys Tyr Gly
                485                 490                 495

Trp Leu Cys Lys Met His Thr Gly Ile Val Arg Asp Lys Lys Lys
                500                 505                 510

Glu Ile Thr Pro His Cys Ala Leu Met Asp Cys Ile Ile Phe Glu Ser
                515                 520                 525

Ala Ser Lys Ala Arg Leu Pro Asp Leu Lys Thr Val His Asn Ile Leu
530                 535                 540
```

Pro His Asp Leu Ile Phe Arg Gly Pro Asn Val Val Thr Leu
545                 550                 555

<210> SEQ ID NO 6
<211> LENGTH: 6680
<212> TYPE: DNA
<213> ORGANISM: Lymphocytic choriomeningitis virus

<400> SEQUENCE: 6

| | | | | | |
|---|---|---|---|---|---|
| cgcaccgagg | atcctaggct | ttttgatgcg | caatggatga | aatcatctca | gaattgagag | 60 |
| agttatgttt | aaactatata | gaacaggatg | agaggttgtc | aaggcagaaa | ctcaactttc | 120 |
| tgggacaaag | gaacccaga | atggttctga | ttgagggact | caagttgctg | tcacgctgca | 180 |
| ttgaaataga | cagtgcagac | aagagtggct | gcacacacaa | ccacgacgat | aagtctgtgg | 240 |
| aaacaatttt | ggtggagtct | ggaattgtat | gcccaggact | accacttatc | attcctgatg | 300 |
| gttacaagct | gatagacaat | tctctcattc | ttcttgagtg | ttttgttagg | agctcaccag | 360 |
| ccagttttga | aagaaattt | atagaggaca | ctaacaaatt | ggcatgcatc | agggaagacc | 420 |
| ttgctgttgc | gggtgtcaca | ttagttccaa | tagtagatgg | tcgttgtgat | tatgataata | 480 |
| gttttatgcc | agagtgggca | aacttcaaat | ttagagacct | tttattcaaa | cttttggagt | 540 |
| attctaacca | aaatgagaaa | gtctttgaag | agtctgaata | ttttagactc | tgtgagtccc | 600 |
| tgaagactac | tatcgacaag | cgctccggta | tggactctat | gaaaattctg | aaagatgcga | 660 |
| ggtcaactca | caatgatgaa | attatgagga | tgtgccacga | aggcatcaac | ccaacatga | 720 |
| gctgtgatga | tgtggttttt | ggaataaact | ctcttttcag | caggtttaga | agagatttag | 780 |
| aaagtgggaa | attaaagaga | aactttcaga | agtaaaccc | tgaaggcttg | atcaaggaat | 840 |
| tctctgagct | ctatgaaaac | cttgctgata | gtgatgatat | cttaacatta | agcagggagg | 900 |
| cagtcgaatc | ctgtcctttg | atgagattca | taactgcaga | gacccatggg | cacgaaaggg | 960 |
| gaagtgagac | tagcactgaa | tatgagaggc | tcctctctat | gttaaacaaa | gtcaagagtt | 1020 |
| tgaaactgtt | gaatactaga | aggagacagt | tgttaaatct | ggatgttttg | tgtctttcct | 1080 |
| cattgataaa | acagtcgaaa | ttcaaagggt | taaaaatga | taaacactgg | gtgggttgtt | 1140 |
| gctatagtag | tgtgaatgat | aggctggtaa | gctttcacag | cactaaagag | gagttcatta | 1200 |
| gacttttgag | gaatagaaaa | agtcaaagg | tgtttagaaa | ggtgtctttt | gaggaattgt | 1260 |
| ttagggcgtc | tattagtgag | ttcattgcaa | aaattcaaaa | atgcctgtta | gtggtgggac | 1320 |
| tgagtttcga | gcattacgga | ctgtctgaac | accttgagca | agaatgccac | ataccattca | 1380 |
| ctgaatttga | gaactttatg | aaaattggag | ctcacccgat | aatgtattat | acgaagtttg | 1440 |
| aagattacaa | tttccaaccc | agcacagagc | agctgaagaa | catacagagc | ctgagaagat | 1500 |
| tatcatctgt | ttgtctggcc | ttaacaaaca | gtatgaaaac | tagctcagtt | gctagactaa | 1560 |
| ggcaaaatca | aatagggtct | gtgagatatc | aagtggtaga | atgcaaagaa | gtgttttgcc | 1620 |
| aagtaataaa | actggactct | gaagaatacc | acctattata | ccagaagact | ggagaatctt | 1680 |
| caaggtgcta | ctccatacaa | ggcccggatg | gtcatttaat | ttccttctat | gcagatccta | 1740 |
| aaaggttctt | tttaccaatt | ttttcagatg | aggtcttata | caatatgata | gacatcatga | 1800 |
| tttcatggat | tagatcatgt | cctgatttga | agactgtct | caccgacatt | gaggttgcac | 1860 |
| tgaggaccct | attgttgcta | atgctcacca | acccaacaaa | gagaaatcaa | aagcaggtac | 1920 |
| agagtgtcag | atatttggtg | atggcaatag | tgtcagattt | ttcatctaca | tcattaatgg | 1980 |
| ataagttgag | ggaggatctg | atcacacctg | ctgagaaggt | ggtgtataag | ctgcttagat | 2040 |

-continued

```
tcctaataaa aactattttt ggtactggtg agaaggtgtt gttgagtgca aaatttaaat    2100
ttatgttgaa tgtgtcatac ctgtgtcatt tgatcacaaa ggagacccct gacaggctaa    2160
cagatcagat aaaatgtttt gaaaagttct ttgagcccaa aagtcaattt ggttttttg     2220 tcaaccccaa ggaagcaatc actcctgagg aagaatgtgt gttctatgag caaatgaaga    2280
gattcactag taaagaaatt gactgtcagc atacaactcc agtgttaat  ctggaagcct    2340 ttagcctaat ggtgtcttca tttaacaacg gcactttaat tttcaaagga gagaagaagc    2400
taaacagcct agatcccatg actaactctg gatgtgcgac agcattagat cttgctagta    2460
acaaaagtgt ggtggttaat aagcatctaa atggagaacg acttctggaa tatgacttta    2520
acaaattgct tgttagtgct gtgagtcaaa ttacggagag tttcgtaaga aaacaaaagt    2580
ataagttgag ccactcagac tatgaatata agtttccaa  gttagtctct agattggtca    2640
tcggttccaa gggagaagag acagggagat cggaagacaa cctggcagaa atatgttttg    2700
atggagaaga agagacaagc ttcttcaaaa gtctcgaaga aaaggtcaac accacaatag    2760
cacggtacag aagaggtagg agggccaatg acaaaggaga tggagaaaaa cttacaaata    2820
caaaaggact acatcattta cagcttattc taacagggaa gatggctcac ttaagaaaag    2880
ttatcttgtc agaaatatct ttccatttag tagaagactt tgacccatca tgtctaacca    2940
atgatgacat gaaatttatc tgtgaggctg ttgagggttc cacagagctg tcacctttgt    3000
atttcacctc agtcattaaa gatcagtgtg gcctcgatga gatggcaaaa aacctttgta    3060
gaaagttctt ttctgagaat gattggtttt cttgcatgaa gatgattctg ttgcaaatga    3120
atgcaaatgc gtactcaggg aaatacaggc atatgcaaag gcaaggcttg aatttcaaat    3180
ttgactggga caaactggaa gaagacgtga gaatcagtga gagggaaagt aattctgagt    3240
cccttagtaa agctctgtcg ttgacaaaat gtatgagtgc tgctttgaaa atctgtgct     3300 tctactcaga agaatcacca acatcataca cctcagtagg tcctgactct ggaaggctga    3360
aatttgcact atcttataaa gagcaggttg ggggaaatag agaactctat attggagatt    3420
tgaggacaaa aatgttcaca aggttaatag aagattattt tgagtctttt tcaagtttct    3480
tttcaggctc ctgtttaaac aatgataagg aatttgaaaa tgcaatcttg tcaatgacta    3540
tcaatgtgcg ggaagggttc ttaaactata gtatggatca cagcaaatgg ggaccaatga    3600
tgtgcccatt tttgttctta atgtttctac aaaatctcaa actaggtgat gaccagtatg    3660
tgcgttccgg gaaagatcat gttagcactt tgttaacttg gcacatgcat aagcttgtcg    3720
aggtcccctt tcctgttgtg aatgcaatga tgaaatcata tgtcaagtcg aagctaaaac    3780
ttctcagggg ttcagaaaca actgttactg agagaatttt cagacaatat tttgaaatgg    3840
ggatagtgcc atcccatata tccagcctta ttgatatggg gcagggaatc ttgcataatg    3900
cttctgactt ctatggtttg cttagcgaga ggttcatcaa ctactgcatt ggtgttatct    3960
ttggcgaaag accagaggct tacacatcaa gtgatgatca gatcacttta tttgatagga    4020
ggctgagtga cctggttgta agtgatccgg aggaagtcct tgtcctgttg gaattccaat    4080
ctcatctgag cggcttgtta aacaaattta tcagcccaaa aagtgtggct gggaggttcg    4140
ctgcagaatt taaatctaga ttctatgtat gggggagga  agtccctctt ctcacaaagt    4200
ttgtatctgc agcgctacac aatgtcaagt gtaaagagcc acatcaactt tgtgaaacaa    4260
tagatacaat tgcagatcaa gccatcgcaa atggcgtccc agtctcccta gttaatagta    4320
tccaaaggag aacactggac ctcctaaagt atgccaattt ccctttggat ccatttctac    4380
```

```
tgaataccaa cactgatgtg aaagattggc tggatggttc tagaggttac agaatacaaa    4440
gactcattga ggaactgtgt cctaatgaaa caaaggttgt aagaaagctt gtaaggaaac    4500
tgcatcataa gctcaaaaat ggtgaattta atgaagaatt tttcttagac ctatttaaca    4560
gagataaaac ggaggccatt cttcaattgg agacctcct cggtcttgaa gaagatctga     4620
atcagttagc agatgttaac tggttgaatt tgaatgaaat gttcccatta aggatggttt    4680
taagacaaaa ggtggtttat ccatcagtga tgactttcca agaggaaaga atcccatcat    4740
tgatcaagac actccagaac aaactttgta gtaaattcac aaggggtgca cagaagctgc    4800
tgtcagaagc aatcaacaag tcagctttcc agagttgtat ctcatctggc tttataggcc    4860
tttgcaaaac tctaggaagc aggtgtgtga gaaacaaaaa tagggaaaat ctgtatatca    4920
aaaagctgct tgaggatcta accacagatg atcatgtgac aagagtttgc aatcgggatg    4980
gtataacgct gtacatttgt gacaaacagt ctcatccaga agcccaccgt gatcatatat    5040
gcctttaag gcctcttctt tgggactaca tttgtatttc attgagcaac tcttttgagt     5100
tgggtgtttg ggtcctagca gaaccgacca aagggaagaa taacagtgag aacctaactc    5160
ttaagcactt aaacccatgt gattatgtag caagaaagcc tgagagctca aggctactgg    5220
aggacaaagt gaatttgaac caagtgattc aatctgtgag gcggctatat cccaagatct    5280
tgaggatca gcttcttcca tttatgtctg acatgagctc aaaaaacatg aggtggagtc     5340
ccagaattaa attccttgac ctctgtgttt taattgatat taactcagaa tccttgtcac    5400
tcatttctca tgttgttaag tggaaaaggg atgaacatta cactgttctg ttttctgacc    5460
ttgccaattc tcatcagcga tctgactcca gtctggttga tgaatttgtt gttagcacga    5520
gggatgtctg caagaacttc ttaaaacagg tgtattttga atcatttgtt cgagaatttg    5580
ttgcaacaac caggacatta ggcaattttt catggttccc tcataaagaa atgatgccat    5640
ctgaagatgt tgctgaggca ctgggccct ttcaatcatt tgtctcaaag gtggtgaaca     5700
aaaatgtgga gaggcctatg tttaggaatg atttgcagtt tggttttggg tggttctctt    5760
accgaatggg agatgttgtg tgtaatgctg ccatgttgat taggcagggc ctgacaaacc    5820
caaaggcatt taaatcctta aaggatctgt gggactacat gctcaactac acaaaagggg    5880
tattggagtt ttcaatttca gtggacttta cgcacaatca gaataatact gactgtttaa    5940
ggaaatttc attgatattc ttggttaggt gccaattaca gaatccaggt gtggctgaac     6000
ttttatcatg ctctcacctc tttaagggtg agatagatag aagaatgttg gatgaatgcc    6060
tccacttact gaggacagac tctgtcttca aggtgaacga tggtgtcttt gatatcagat    6120
ctgaagagtt tgaggattac atggaagatc ccttgatact tggtgattct cttgagcttg    6180
agttgttggg ctccaaaaga atactggatg ggattagatc tattgacttt gagagagttg    6240
gacctgagtg ggagcctgtg ccactgactg taaagatggg tgccctttt gaaggaagaa     6300
accttgtcca aaatatcatt gtgaagctgg agaccaagga catgaaagtc tttctagcag    6360
gacttgaggc ctatgaaaag attagtgatg tccttgggaa cctcttcctg catccgattca    6420
gaactggtga acatttgttg ggttcagaga taagtgtaat cctccaggaa ctatgtatag    6480
acagatctat tctgctgatt ccactgtcgc ttttgccaga ctggttcgcc tttaaggatt    6540
gcagactttg ttttagcaaa tctaggagca ctttgatgta tgaaatagtg gggggcaggt    6600
ttagactcaa ggggaggtcc tgcgacgatt ggctaggcgg gtcggtggcc gaggacatcg    6660
actgatgggc atctcctggg                                               6680
```

```
<210> SEQ ID NO 7
<211> LENGTH: 2210
<212> TYPE: PRT
<213> ORGANISM: Lymphocytic choriomeningitis virus
<220> FEATURE:
<223> OTHER INFORMATION: L protein

<400> SEQUENCE: 7

Met Asp Glu Ile Ile Ser Glu Leu Arg Glu Leu Cys Leu Asn Tyr Ile
  1               5                  10                  15

Glu Gln Asp Glu Arg Leu Ser Arg Gln Lys Leu Asn Phe Leu Gly Gln
             20                  25                  30

Arg Glu Pro Arg Met Val Leu Ile Glu Gly Leu Lys Leu Leu Ser Arg
         35                  40                  45

Cys Ile Glu Ile Asp Ser Ala Asp Lys Ser Gly Cys Thr His Asn His
 50                  55                  60

Asp Asp Lys Ser Val Glu Thr Ile Leu Val Glu Ser Gly Ile Val Cys
 65                  70                  75                  80

Pro Gly Leu Pro Leu Ile Ile Pro Asp Gly Tyr Lys Leu Ile Asp Asn
                 85                  90                  95

Ser Leu Ile Leu Leu Glu Cys Phe Val Arg Ser Ser Pro Ala Ser Phe
                100                 105                 110

Glu Lys Lys Phe Ile Glu Asp Thr Asn Lys Leu Ala Cys Ile Arg Glu
            115                 120                 125

Asp Leu Ala Val Ala Gly Val Thr Leu Val Pro Ile Val Asp Gly Arg
        130                 135                 140

Cys Asp Tyr Asp Asn Ser Phe Met Pro Glu Trp Ala Asn Phe Lys Phe
145                 150                 155                 160

Arg Asp Leu Leu Phe Lys Leu Leu Glu Tyr Ser Asn Gln Asn Glu Lys
                165                 170                 175

Val Phe Glu Glu Ser Glu Tyr Phe Arg Leu Cys Glu Ser Leu Lys Thr
            180                 185                 190

Thr Ile Asp Lys Arg Ser Gly Met Asp Ser Met Lys Ile Leu Lys Asp
        195                 200                 205

Ala Arg Ser Thr His Asn Asp Glu Ile Met Arg Met Cys His Glu Gly
    210                 215                 220

Ile Asn Pro Asn Met Ser Cys Asp Asp Val Val Phe Gly Ile Asn Ser
225                 230                 235                 240

Leu Phe Ser Arg Phe Arg Arg Asp Leu Glu Ser Gly Lys Leu Lys Arg
                245                 250                 255

Asn Phe Gln Lys Val Asn Pro Glu Gly Leu Ile Lys Glu Phe Ser Glu
            260                 265                 270

Leu Tyr Glu Asn Leu Ala Asp Ser Asp Ile Leu Thr Leu Ser Arg
        275                 280                 285

Glu Ala Val Glu Ser Cys Pro Leu Met Arg Phe Ile Thr Ala Glu Thr
    290                 295                 300

His Gly His Glu Arg Gly Ser Glu Thr Ser Thr Glu Tyr Glu Arg Leu
305                 310                 315                 320

Leu Ser Met Leu Asn Lys Val Lys Ser Leu Lys Leu Asn Thr Arg
                325                 330                 335

Arg Arg Gln Leu Leu Asn Leu Asp Val Leu Cys Leu Ser Ser Leu Ile
            340                 345                 350

Lys Gln Ser Lys Phe Lys Gly Leu Lys Asn Asp Lys His Trp Val Gly
        355                 360                 365

Cys Cys Tyr Ser Ser Val Asn Asp Arg Leu Val Ser Phe His Ser Thr
```

-continued

```
              370                 375                 380
Lys Glu Glu Phe Ile Arg Leu Leu Arg Asn Arg Lys Lys Ser Lys Val
385                 390                 395                 400
Phe Arg Lys Val Ser Phe Glu Glu Leu Phe Arg Ala Ser Ile Ser Glu
                    405                 410                 415
Phe Ile Ala Lys Ile Gln Lys Cys Leu Leu Val Val Gly Leu Ser Phe
                420                 425                 430
Glu His Tyr Gly Leu Ser Glu His Leu Glu Gln Glu Cys His Ile Pro
            435                 440                 445
Phe Thr Glu Phe Glu Asn Phe Met Lys Ile Gly Ala His Pro Ile Met
        450                 455                 460
Tyr Tyr Thr Lys Phe Glu Asp Tyr Asn Phe Gln Pro Ser Thr Glu Gln
465                 470                 475                 480
Leu Lys Asn Ile Gln Ser Leu Arg Arg Leu Ser Ser Val Cys Leu Ala
                    485                 490                 495
Leu Thr Asn Ser Met Lys Thr Ser Ser Val Ala Arg Leu Arg Gln Asn
                500                 505                 510
Gln Ile Gly Ser Val Arg Tyr Gln Val Val Glu Cys Lys Glu Val Phe
            515                 520                 525
Cys Gln Val Ile Lys Leu Asp Ser Glu Glu Tyr His Leu Leu Tyr Gln
        530                 535                 540
Lys Thr Gly Glu Ser Ser Arg Cys Tyr Ser Ile Gln Gly Pro Asp Gly
545                 550                 555                 560
His Leu Ile Ser Phe Tyr Ala Asp Pro Lys Arg Phe Phe Leu Pro Ile
                    565                 570                 575
Phe Ser Asp Glu Val Leu Tyr Asn Met Ile Asp Ile Met Ile Ser Trp
                580                 585                 590
Ile Arg Ser Cys Pro Asp Leu Lys Asp Cys Leu Thr Asp Ile Glu Val
            595                 600                 605
Ala Leu Arg Thr Leu Leu Leu Met Leu Thr Asn Pro Thr Lys Arg
        610                 615                 620
Asn Gln Lys Gln Val Gln Ser Val Arg Tyr Leu Val Met Ala Ile Val
625                 630                 635                 640
Ser Asp Phe Ser Ser Thr Ser Leu Met Asp Lys Leu Arg Glu Asp Leu
                    645                 650                 655
Ile Thr Pro Ala Glu Lys Val Val Tyr Lys Leu Leu Arg Phe Leu Ile
                660                 665                 670
Lys Thr Ile Phe Gly Thr Gly Glu Lys Val Leu Leu Ser Ala Lys Phe
            675                 680                 685
Lys Phe Met Leu Asn Val Ser Tyr Leu Cys His Leu Ile Thr Lys Glu
        690                 695                 700
Thr Pro Asp Arg Leu Thr Asp Gln Ile Lys Cys Phe Glu Lys Phe Phe
705                 710                 715                 720
Glu Pro Lys Ser Gln Phe Gly Phe Val Asn Pro Lys Glu Ala Ile
                    725                 730                 735
Thr Pro Glu Glu Cys Val Phe Tyr Glu Gln Met Lys Arg Phe Thr
                740                 745                 750
Ser Lys Glu Ile Asp Cys Gln His Thr Thr Pro Gly Val Asn Leu Glu
            755                 760                 765
Ala Phe Ser Leu Met Val Ser Ser Phe Asn Asn Gly Thr Leu Ile Phe
        770                 775                 780
Lys Gly Glu Lys Lys Leu Asn Ser Leu Asp Pro Met Thr Asn Ser Gly
785                 790                 795                 800
```

-continued

```
Cys Ala Thr Ala Leu Asp Leu Ala Ser Asn Lys Ser Val Val Asn
            805                 810                 815

Lys His Leu Asn Gly Glu Arg Leu Leu Glu Tyr Asp Phe Asn Lys Leu
            820                 825                 830

Leu Val Ser Ala Val Ser Gln Ile Thr Glu Ser Phe Val Arg Lys Gln
            835                 840                 845

Lys Tyr Lys Leu Ser His Ser Asp Tyr Glu Tyr Lys Val Ser Lys Leu
            850                 855                 860

Val Ser Arg Leu Val Ile Gly Ser Lys Gly Glu Glu Thr Gly Arg Ser
865                 870                 875                 880

Glu Asp Asn Leu Ala Glu Ile Cys Phe Asp Gly Glu Glu Thr Ser
            885                 890                 895

Phe Phe Lys Ser Leu Glu Glu Lys Val Asn Thr Thr Ile Ala Arg Tyr
            900                 905                 910

Arg Arg Gly Arg Arg Ala Asn Asp Lys Gly Asp Gly Lys Leu Thr
            915                 920                 925

Asn Thr Lys Gly Leu His His Leu Gln Leu Ile Leu Thr Gly Lys Met
            930                 935                 940

Ala His Leu Arg Lys Val Ile Leu Ser Glu Ile Ser Phe His Leu Val
945                 950                 955                 960

Glu Asp Phe Asp Pro Ser Cys Leu Thr Asn Asp Asp Met Lys Phe Ile
            965                 970                 975

Cys Glu Ala Val Glu Gly Ser Thr Glu Leu Ser Pro Tyr Tyr Phe Thr
            980                 985                 990

Ser Val Ile Lys Asp Gln Cys Gly Leu Asp Glu Met Ala Lys Asn Leu
            995                 1000                1005

Cys Arg Lys Phe Phe Ser Glu Asn Asp Trp Phe Ser Cys Met Lys Met
        1010                1015                1020

Ile Leu Leu Gln Met Asn Ala Asn Ala Tyr Ser Gly Lys Tyr Arg His
1025                1030                1035                1040

Met Gln Arg Gln Gly Leu Asn Phe Lys Phe Asp Trp Asp Lys Leu Glu
            1045                1050                1055

Glu Asp Val Arg Ile Ser Glu Arg Glu Ser Asn Ser Glu Ser Leu Ser
            1060                1065                1070

Lys Ala Leu Ser Leu Thr Lys Cys Met Ser Ala Ala Leu Lys Asn Leu
            1075                1080                1085

Cys Phe Tyr Ser Glu Glu Ser Pro Thr Ser Tyr Thr Ser Val Gly Pro
            1090                1095                1100

Asp Ser Gly Arg Leu Lys Phe Ala Leu Ser Tyr Lys Glu Gln Val Gly
1105                1110                1115                1120

Gly Asn Arg Glu Leu Tyr Ile Gly Asp Leu Arg Thr Lys Met Phe Thr
            1125                1130                1135

Arg Leu Ile Glu Asp Tyr Phe Glu Ser Phe Ser Ser Phe Phe Ser Gly
            1140                1145                1150

Ser Cys Leu Asn Asn Asp Lys Gly Phe Glu Asn Ala Ile Leu Ser Met
            1155                1160                1165

Thr Ile Asn Val Arg Glu Gly Phe Leu Asn Tyr Ser Met Asp His Ser
    1170                1175                1180

Lys Trp Gly Pro Met Met Cys Pro Phe Leu Phe Leu Met Phe Leu Gln
1185                1190                1195                1200

Asn Leu Lys Leu Gly Asp Asp Gln Tyr Val Arg Ser Gly Lys Asp His
            1205                1210                1215
```

-continued

Val Ser Thr Leu Leu Thr Trp His Met His Lys Leu Val Glu Val Pro
            1220                1225                1230

Phe Pro Val Val Asn Ala Met Met Lys Ser Tyr Val Lys Ser Lys Leu
        1235                1240                1245

Lys Leu Leu Arg Gly Ser Glu Thr Thr Val Thr Glu Arg Ile Phe Arg
    1250                1255                1260

Gln Tyr Phe Glu Met Gly Ile Val Pro Ser His Ile Ser Ser Leu Ile
1265                1270                1275                1280

Asp Met Gly Gln Gly Ile Leu His Asn Ala Ser Asp Phe Tyr Gly Leu
                1285                1290                1295

Leu Ser Glu Arg Phe Ile Asn Tyr Cys Ile Gly Val Ile Phe Gly Glu
            1300                1305                1310

Arg Pro Glu Ala Tyr Thr Ser Ser Asp Asp Gln Ile Thr Leu Phe Asp
        1315                1320                1325

Arg Arg Leu Ser Asp Leu Val Val Ser Asp Pro Glu Glu Val Leu Val
    1330                1335                1340

Leu Leu Glu Phe Gln Ser His Leu Ser Gly Leu Leu Asn Lys Phe Ile
1345                1350                1355                1360

Ser Pro Lys Ser Val Ala Gly Arg Phe Ala Ala Glu Phe Lys Ser Arg
                1365                1370                1375

Phe Tyr Val Trp Gly Glu Glu Val Pro Leu Leu Thr Lys Phe Val Ser
            1380                1385                1390

Ala Ala Leu His Asn Val Lys Cys Lys Glu Pro His Gln Leu Cys Glu
        1395                1400                1405

Thr Ile Asp Thr Ile Ala Asp Gln Ala Ile Ala Asn Gly Val Pro Val
    1410                1415                1420

Ser Leu Val Asn Ser Ile Gln Arg Arg Thr Leu Asp Leu Leu Lys Tyr
1425                1430                1435                1440

Ala Asn Phe Pro Leu Asp Pro Phe Leu Leu Asn Thr Asn Thr Asp Val
                1445                1450                1455

Lys Asp Trp Leu Asp Gly Ser Arg Gly Tyr Arg Ile Gln Arg Leu Ile
            1460                1465                1470

Glu Glu Leu Cys Pro Asn Glu Thr Lys Val Val Arg Lys Leu Val Arg
        1475                1480                1485

Lys Leu His His Lys Leu Lys Asn Gly Glu Phe Asn Glu Glu Phe Phe
    1490                1495                1500

Leu Asp Leu Phe Asn Arg Asp Lys Thr Glu Ala Ile Leu Gln Leu Gly
1505                1510                1515                1520

Asp Leu Leu Gly Leu Glu Glu Asp Leu Asn Gln Leu Ala Asp Val Asn
                1525                1530                1535

Trp Leu Asn Leu Asn Glu Met Phe Pro Leu Arg Met Val Leu Arg Gln
            1540                1545                1550

Lys Val Val Tyr Pro Ser Val Met Thr Phe Gln Glu Glu Arg Ile Pro
        1555                1560                1565

Ser Leu Ile Lys Thr Leu Gln Asn Lys Leu Cys Ser Lys Phe Thr Arg
    1570                1575                1580

Gly Ala Gln Lys Leu Leu Ser Glu Ala Ile Asn Lys Ser Ala Phe Gln
1585                1590                1595                1600

Ser Cys Ile Ser Ser Gly Phe Ile Gly Leu Cys Lys Thr Leu Gly Ser
                1605                1610                1615

Arg Cys Val Arg Asn Lys Asn Arg Glu Asn Leu Tyr Ile Lys Lys Leu
            1620                1625                1630

Leu Glu Asp Leu Thr Thr Asp Asp His Val Thr Arg Val Cys Asn Arg

-continued

```
          1635              1640              1645

Asp Gly Ile Thr Leu Tyr Ile Cys Asp Lys Gln Ser His Pro Glu Ala
    1650              1655              1660

His Arg Asp His Ile Cys Leu Leu Arg Pro Leu Leu Trp Asp Tyr Ile
1665              1670              1675              1680

Cys Ile Ser Leu Ser Asn Ser Phe Glu Leu Gly Val Trp Val Leu Ala
        1685              1690              1695

Glu Pro Thr Lys Gly Lys Asn Asn Ser Glu Asn Leu Thr Leu Lys His
    1700              1705              1710

Leu Asn Pro Cys Asp Tyr Val Ala Arg Lys Pro Glu Ser Ser Arg Leu
        1715              1720              1725

Leu Glu Asp Lys Val Asn Leu Asn Gln Val Ile Gln Ser Val Arg Arg
    1730              1735              1740

Leu Tyr Pro Lys Ile Phe Glu Asp Gln Leu Leu Pro Phe Met Ser Asp
1745              1750              1755              1760

Met Ser Ser Lys Asn Met Arg Trp Ser Pro Arg Ile Lys Phe Leu Asp
            1765              1770              1775

Leu Cys Val Leu Ile Asp Ile Asn Ser Glu Ser Leu Ser Leu Ile Ser
            1780              1785              1790

His Val Val Lys Trp Lys Arg Asp Glu His Tyr Thr Val Leu Phe Ser
        1795              1800              1805

Asp Leu Ala Asn Ser His Gln Arg Ser Asp Ser Ser Leu Val Asp Glu
    1810              1815              1820

Phe Val Val Ser Thr Arg Asp Val Cys Lys Asn Phe Leu Lys Gln Val
1825              1830              1835              1840

Tyr Phe Glu Ser Phe Val Arg Glu Phe Val Ala Thr Thr Arg Thr Leu
            1845              1850              1855

Gly Asn Phe Ser Trp Phe Pro His Lys Glu Met Met Pro Ser Glu Asp
        1860              1865              1870

Gly Ala Glu Ala Leu Gly Pro Phe Gln Ser Phe Val Ser Lys Val Val
        1875              1880              1885

Asn Lys Asn Val Glu Arg Pro Met Phe Arg Asn Asp Leu Gln Phe Gly
    1890              1895              1900

Phe Gly Trp Phe Ser Tyr Arg Met Gly Asp Val Val Cys Asn Ala Ala
1905              1910              1915              1920

Met Leu Ile Arg Gln Gly Leu Thr Asn Pro Lys Ala Phe Lys Ser Leu
            1925              1930              1935

Lys Asp Leu Trp Asp Tyr Met Leu Asn Tyr Thr Lys Gly Val Leu Glu
            1940              1945              1950

Phe Ser Ile Ser Val Asp Phe Thr His Asn Gln Asn Asn Thr Asp Cys
    1955              1960              1965

Leu Arg Lys Phe Ser Leu Ile Phe Leu Val Arg Cys Gln Leu Gln Asn
    1970              1975              1980

Pro Gly Val Ala Glu Leu Leu Ser Cys Ser His Leu Phe Lys Gly Glu
1985              1990              1995              2000

Ile Asp Arg Arg Met Leu Asp Glu Cys Leu His Leu Leu Arg Thr Asp
            2005              2010              2015

Ser Val Phe Lys Val Asn Asp Gly Val Phe Asp Ile Arg Ser Glu Glu
            2020              2025              2030

Phe Glu Asp Tyr Met Glu Asp Pro Leu Ile Leu Gly Asp Ser Leu Glu
        2035              2040              2045

Leu Glu Leu Leu Gly Ser Lys Arg Ile Leu Asp Gly Ile Arg Ser Ile
    2050              2055              2060
```

-continued

```
Asp Phe Glu Arg Val Gly Pro Glu Trp Glu Pro Val Pro Leu Thr Val
2065                2070                2075                2080

Lys Met Gly Ala Leu Phe Glu Gly Arg Asn Leu Val Gln Asn Ile Ile
            2085                2090                2095

Val Lys Leu Glu Thr Lys Asp Met Lys Val Phe Leu Ala Gly Leu Glu
        2100                2105                2110

Gly Tyr Glu Lys Ile Ser Asp Val Leu Gly Asn Leu Phe Leu His Arg
    2115                2120                2125

Phe Arg Thr Gly Glu His Leu Leu Gly Ser Glu Ile Ser Val Ile Leu
    2130                2135                2140

Gln Glu Leu Cys Ile Asp Arg Ser Ile Leu Ile Pro Leu Ser Leu
2145                2150                2155                2160

Leu Pro Asp Trp Phe Ala Phe Lys Asp Cys Arg Leu Cys Phe Ser Lys
            2165                2170                2175

Ser Arg Ser Thr Leu Met Tyr Glu Ile Val Gly Gly Arg Phe Arg Leu
            2180                2185                2190

Lys Gly Arg Ser Cys Asp Asp Trp Leu Gly Gly Ser Val Ala Glu Asp
        2195                2200                2205

Ile Asp
   2210

<210> SEQ ID NO 8
<211> LENGTH: 95
<212> TYPE: PRT
<213> ORGANISM: Lymphocytic choriomeningitis virus
<220> FEATURE:
<223> OTHER INFORMATION: unknown protein

<400> SEQUENCE: 8

Met Ser Ser Ala Thr Asp Pro Pro Ser Gln Ser Ser Gln Asp Leu Pro
1               5                   10                  15

Leu Ser Leu Asn Leu Pro Pro Thr Ile Ser Tyr Ile Lys Val Leu Leu
            20                  25                  30

Asp Leu Leu Lys Gln Ser Leu Gln Ser Leu Lys Ala Asn Gln Ser Gly
        35                  40                  45

Lys Ser Asp Ser Gly Ile Ser Arg Ile Asp Leu Ser Ile His Ser Ser
    50                  55                  60

Trp Arg Ile Thr Leu Ile Ser Glu Pro Asn Lys Cys Ser Pro Val Leu
65                  70                  75                  80

Asn Arg Cys Arg Lys Arg Phe Pro Arg Thr Ser Leu Ile Phe Ser
            85                  90                  95

<210> SEQ ID NO 9
<211> LENGTH: 4695
<212> TYPE: DNA
<213> ORGANISM: Homo sapiens

<400> SEQUENCE: 9
cccgggctgg gctgagaccc gcagaggaag acgctctagg gatttgtccc ggactagcga      60
gatggcaagg ctgaggacgg gaggctgatt gagaggcgaa ggtacaccct aatctcaata     120
caacctttgg agctaagcca gcaatggtag agggaagatt ctgcacgtcc cttccaggcg     180
gcctccccgt caccaccccc cccaacccgc cccgaccgga gctgagagta attcatacaa     240
aaggactcgc ccctgccttg gggaatccca gggaccgtcg ttaaactccc actaacgtag     300
aacccagaga tcgctgcgtt cccgccccct cacccgcccg ctctcgtcat cactgaggtg     360
```

-continued

| | | |
|---|---|---|
| gagaagagca tgcgtgaggc tccggtgccc gtcagtgggc agagcgcaca tcgcccacag | 420 |
| tccccgagaa gttgggggga ggggtcggca attgaaccgg tgcctagaga aggtggcgcg | 480 |
| gggtaaactg ggaaagtgat gtcgtgtact ggctccgcct ttttcccgag ggtgggggag | 540 |
| aaccgtatat aagtgcagta gtcgccgtga acgttctttt tcgcaacggg tttgccgcca | 600 |
| gaacacaggt aagtgccgtg tgtggttccc gcgggcctgg cctctttacg ggttatggcc | 660 |
| cttgcgtgcc ttgaattact tccacgcccc tggctgcagt acgtgattct tgatcccgag | 720 |
| cttcgggttg gaagtgggtg ggagagttcg aggccttgcg cttaaggagc cccttcgcct | 780 |
| cgtgcttgag ttgaggcctg gcctgggcgc tggggccgcc gcgtgcgaat ctggtggcac | 840 |
| cttcgcgcct gtctcgctgc tttcgataag tctctagcca tttaaaattt ttgatgacct | 900 |
| gctgcgacgc ttttttttctg gcaagatagt cttgtaaatg cgggccaaga tctgcacact | 960 |
| ggtatttcgg ttttttgggc cgcgggcgg gacggggccc gtgcgtccca gcgcacatgt | 1020 |
| tcggcgaggc ggggcctgcg agcgcggcca ccagaaatcg gacggggta gtctcaagct | 1080 |
| ggccggcctg ctctggtgcc tggcctcgcg ccgccgtgta tcgccccgcc ctgggcggca | 1140 |
| aggctggccc ggtcggcacc agttgcgtga gcggaaagat ggccgcttcc cggccctgct | 1200 |
| gcagggagct caaaatggag gacgcggcgc tcgggagagc gggcgggtga gtcacccaca | 1260 |
| caaaggaaaa gggcctttcc gtcctcagcc gtcgcttcat gtgactccac ggagtaccgg | 1320 |
| gcgccgtcca ggcacctcga ttagttctcg agcttttgga gtacgtcgtc tttaggttgg | 1380 |
| ggggaggggt tttatgcgat ggagtttccc cacactgagt gggtggagac tgaagttagg | 1440 |
| ccagcttggc acttgatgta attctccttg gaatttgccc ttttgagtt tggatcttgg | 1500 |
| ttcattctca agcctcagac agtggttcaa agttttttc ttccatttca ggtgtcgtga | 1560 |
| aaactacccc taaaagccaa aatgggaaag gaaaagactc atatcaacat tgtcgtcatt | 1620 |
| ggacacgtag attcgggcaa gtccaccact actggccatc tgatctataa atgcggtggc | 1680 |
| atcgacaaaa gaaccattga aaaatttgag aaggaggctg ctgaggtatg tttaatacca | 1740 |
| gaaagggaaa gatcaactaa aatgagtttt accagcagaa tcattaggtg atttccccag | 1800 |
| aactagtgag tggtttagat ctgaatgcta atagttaaga ccttacttat gaataatttt | 1860 |
| tgcttttggt gacttctgta atcgtattgc tagtgagtag atttggatgt taatagttaa | 1920 |
| gatcctactt ataaaagttt gatttttggt tgcttctgta acccaaagtg accaaaatca | 1980 |
| ctttggactt ggagttgtaa agtggaaact gccaattaag ggctggggac aaggaaattg | 2040 |
| aagctggagt ttgtgttta gtaaccaagt aacgactctt aatccttaca gatgggaaag | 2100 |
| ggctccttca agtatgcctg ggtcttggat aaactgaaag ctgagcgtga acgtggtatc | 2160 |
| accattgata tctccttgtg gaaatttgag accagcaagt actatgtgac tatcattgat | 2220 |
| gccccaggac acagagactt tatcaaaaac atgattacag ggacatctca ggtttgggatt | 2280 |
| aataattcta ggtttctta tcccaaaagg cttgctttgt acactggttt tgtcatttgg | 2340 |
| agagttgaca gggatatgtc tttgctttct ttaaaggctg actgtgctgt cctgattgtt | 2400 |
| gctgctggtg ttggtgaatt tgaagctggt atctccaaga atgggcagac ccgagagcat | 2460 |
| gcccttctgg cttacacact gggtgtgaaa caactaattg tcggtgttaa caaaatggat | 2520 |
| tccactgagc caccctacag ccagaagaga tatgaggaaa ttgttaagga agtcagcact | 2580 |
| tacattaaga aaattggcta caaccccgac acagtagcat ttgtgccaat ttctggttgg | 2640 |
| aatggtgaca acatgctgga gccaagtgct aacgtaagtg gctttcaaga ccattgttaa | 2700 |
| aaagctctgg gaatggcgat ttcatgctta cacaaattgg catgcttgtg tttcagatgc | 2760 |

-continued

```
cttggttcaa gggatggaaa gtcacccgta aggatggcaa tgccagtgga accacgctgc   2820
ttgaggctct ggactgcatc ctaccaccaa ctcgtccaac tgacaagccc ttgcgcctgc   2880
ctctccagga tgtctacaaa attggtggta agttggctgt aaacaaagtt gaatttgagt   2940
tgatagagta ctgtctgcct tcataggtat ttagtatgct gtaaatattt ttaggtattg   3000
gtactgttcc tgttggccga gtggagactg gtgttctcaa acccggtatg gtggtcacct   3060
ttgctccagt caacgttaca acggaagtaa aatctgtcga aatgcaccat gaagctttga   3120
gtgaagctct tcctggggac aatgtgggct tcaatgtcaa gaatgtgtct gtcaaggatg   3180
ttcgtcgtgg caacgttgct ggtgacagca aaaatgaccc accaatggaa gcagctggct   3240
tcactgctca ggtaacaatt taaagtaaca ttaacttatt gcagaggcta aagtcatttg   3300
agactttgga tttgcactga atgcaaatct tttttccaag gtgattatcc tgaaccatcc   3360
aggccaaata agcgccggct atgccccgtgt attggattgc cacacggctc acattgcatg   3420
caagtttgct gagctgaagg aaaagattga tcgccgttct ggtaaaaagc tggaagatgg   3480
ccctaaattc ttgaagtctg gtgatgctgc cattgttgat atggttcctg caagcccat    3540
gtgtgttgag agcttctcag actatccacc tttgggtaag gatgactact taaatgtaaa   3600
aaagttgtgt taaagatgaa aaatacaact gaacagtact ttgggtaata attaactttt   3660
tttttaatag gtcgctttgc tgttcgtgat atgagacaga cagttgcggt gggtgtcatc   3720
aaagcagtgg acaagaaggc tgctggagct ggcaaggtca ccaagtctgc ccagaaagct   3780
cagaaggcta aatgaatatt atccctaata cctgccaccc cactcttaat cagtggtgga   3840
agaacggtct cagaactgtt tgtttcaatt ggccattaa gtttagtagt aaaagactgg   3900
ttaatgataa caatgcatcg taaaaccttc agaaggaaag gagaatgttt tgtggaccac   3960
tttggttttc ttttttgcgt gtggcagttt taagttatta gttttaaaa tcagtacttt    4020
ttaatggaaa caacttgacc aaaaatttgt cacagaattt tgagacccat taaaaagtt    4080
aaatgagaaa cctgtgtgtt cctttggtca acaccgagac atttaggtga agacatcta    4140
attctggttt tacgaatctg gaaacttctt gaaaatgtaa ttcttgagtt aacacttctg   4200
ggtggagaat agggttgttt tccccccaca taattggaag gggaaggaat atcatttaaa   4260
gctatgggag ggtttcttg attacaacac tggagagaaa tgcagcatgt tgctgattgc   4320
ctgtcactaa aacaggccaa aaactgagtc cttgggttgc atagaaagct tcatgttgct   4380
aaaccaatgt taagtgaatc tttggaaaca aaatgtttcc aaattactgg gatgtgcatg   4440
ttgaaacgtg ggttaaaatg actgggcagt gaaagttgac tatttgccat gacataagaa   4500
ataagtgtag tggctagtgt acaccctatg agtggaaggg tccattttga agtcagtgga   4560
gtaagcttta tgccatttttg atggtttcac aagttctatt gagtgctatt cagaatagga   4620
acaaggttct aatagaaaaa gatggcaatt tgaagtagct ataaaattag actaattaca   4680
ttgcttttct ccgac                                                    4695
```

<210> SEQ ID NO 10
<211> LENGTH: 462
<212> TYPE: PRT
<213> ORGANISM: Homo sapiens
<220> FEATURE:
<223> OTHER INFORMATION: elongation factor EF-1-alpha

<400> SEQUENCE: 10

```
Met Gly Lys Glu Lys Thr His Ile Asn Ile Val Val Ile Gly His Val
 1               5                  10                  15
```

```
Asp Ser Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
            35                  40                  45

Met Gly Lys Gly Ser Phe Lys Tyr Ala Trp Val Leu Asp Lys Leu Lys
 50                  55                  60

Ala Glu Arg Glu Arg Gly Ile Thr Ile Asp Ile Ser Leu Trp Lys Phe
 65                  70                  75                  80

Glu Thr Ser Lys Tyr Tyr Val Thr Ile Ile Asp Ala Pro Gly His Arg
                 85                  90                  95

Asp Phe Ile Lys Asn Met Ile Thr Gly Thr Ser Gln Ala Asp Cys Ala
            100                 105                 110

Val Leu Ile Val Ala Ala Gly Val Gly Glu Phe Glu Ala Gly Ile Ser
            115                 120                 125

Lys Asn Gly Gln Thr Arg Glu His Ala Leu Leu Ala Tyr Thr Leu Gly
            130                 135                 140

Val Lys Gln Leu Ile Val Gly Val Asn Lys Met Asp Ser Thr Glu Pro
145                 150                 155                 160

Pro Tyr Ser Gln Lys Arg Tyr Glu Glu Ile Val Lys Glu Val Ser Thr
                165                 170                 175

Tyr Ile Lys Lys Ile Gly Tyr Asn Pro Asp Thr Val Ala Phe Val Pro
            180                 185                 190

Ile Ser Gly Trp Asn Gly Asp Asn Met Leu Glu Pro Ser Ala Asn Met
            195                 200                 205

Pro Trp Phe Lys Gly Trp Lys Val Thr Arg Lys Asp Gly Asn Ala Ser
210                 215                 220

Gly Thr Thr Leu Leu Glu Ala Leu Asp Cys Ile Leu Pro Pro Thr Arg
225                 230                 235                 240

Pro Thr Asp Lys Pro Leu Arg Leu Pro Leu Gln Asp Val Tyr Lys Ile
                245                 250                 255

Gly Gly Ile Gly Thr Val Pro Val Gly Arg Val Glu Thr Gly Val Leu
            260                 265                 270

Lys Pro Gly Met Val Val Thr Phe Ala Pro Val Asn Val Thr Thr Glu
            275                 280                 285

Val Lys Ser Val Glu Met His His Glu Ala Leu Ser Glu Ala Leu Pro
            290                 295                 300

Gly Asp Asn Val Gly Phe Asn Val Lys Asn Val Ser Val Lys Asp Val
305                 310                 315                 320

Arg Arg Gly Asn Val Ala Gly Asp Ser Lys Asn Asp Pro Pro Met Glu
                325                 330                 335

Ala Ala Gly Phe Thr Ala Gln Val Ile Ile Leu Asn His Pro Gly Gln
            340                 345                 350

Ile Ser Ala Gly Tyr Ala Pro Val Leu Asp Cys His Thr Ala His Ile
            355                 360                 365

Ala Cys Lys Phe Ala Glu Leu Lys Glu Lys Ile Asp Arg Arg Ser Gly
            370                 375                 380

Lys Lys Leu Glu Asp Gly Pro Lys Phe Leu Lys Ser Gly Asp Ala Ala
385                 390                 395                 400

Ile Val Asp Met Val Pro Gly Lys Pro Met Cys Val Glu Ser Phe Ser
                405                 410                 415

Asp Tyr Pro Pro Leu Gly Arg Phe Ala Val Arg Asp Met Arg Gln Thr
            420                 425                 430
```

```
Val Ala Val Gly Val Ile Lys Ala Val Asp Lys Lys Ala Ala Gly Ala
        435                 440                 445

Gly Lys Val Thr Lys Ser Ala Gln Lys Ala Gln Lys Ala Lys
    450                 455                 460

<210> SEQ ID NO 11
<211> LENGTH: 8332
<212> TYPE: DNA
<213> ORGANISM: Moloney murine leukemia virus

<400> SEQUENCE: 11
tatgcgcctg cgtcggtact agttagctaa ctagctctgt atctggcgga cccgtggtgg     60
aactgacgag ttcggaacac ccggccgcaa ccctgggaga cgtcccaggg acttcggggg    120 ccgttttgt ggcccgacct gagtccaaaa atcccgatcg ttttggactc tttggtgcac     180
cccccttaga ggagggatat gtggttctgg taggagacga gaacctaaaa cagttcccgc    240
ctccgtctga attttgctt tcggtttggg accgaagccg cgccgcgcgt cttgtctgct     300
gcagcatcgt tctgtgttgt ctctgtctga ctgtgtttct gtatttgtct gagaatatgg    360
gccagactgt taccactccc ttaagtttga ccttaggtca ctggaaagat gtcgagcgga    420
tcgctcacaa ccagtcggta gatgtcaaga agagacgttg ggttaccttc tgctctgcag    480
aatggccaac ctttaacgtc ggatggccgc gagacggcac ctttaaccga gacctcatca    540
cccaggttaa gatcaaggtc ttttcacctg gcccgcatgg acacccagac caggtcccct    600
acatcgtgac ctgggaagcc ttggcttttg accccctcc ctgggtcaag ccctttgtac     660
accctaagcc tccgcctcct cttcctccat ccgcccgtc tctccccctt gaacctcctc     720
gttcgacccc gcctcgatcc tcctttatc cagccctcac tccttctcta ggcgccaaac     780
ctaaacctca gttctttct gacagtgggg ggccgctcat cgacctactt acagaagacc     840
ccccgcctta tagggaccca agaccacccc cttccgacag gacggaaat ggtggagaag     900 cgaccctgc gggagaggca ccggaccct cccaatggc atctcgccta cgtgggagac       960
gggagccccc tgtggccgac tccactacct cgcaggcatt cccctccgc gcaggaggaa    1020 acggacagct tcaatactgg ccgttctcct cttctgacct ttacaactgg aaaaataata    1080 accttctt ttctgaagat ccaggtaaac tgacagctct gatcgagtct gttctcatca     1140
cccatcagcc cacctgggac gactgtcagc agctgttggg gactctgctg accggagaag   1200
aaaaacaacg ggtgctctta gagctagaa aggcggtgcg gggcgatgat gggcgcccca   1260
ctcaactgcc caatgaagtc gatgccgctt ttcccctcga gcgcccagac tgggattaca   1320
ccacccaggc aggtaggaac cacctagtcc actatcgcca gttgctccta gcgggtctcc   1380
aaaacgcggg cagaagcccc accaatttgg ccaaggtaaa aggaataaca caagggccca   1440
atgagtctcc ctcggccttc ctagagagac ttaaggaagc ctatcgcagg tacactcctt   1500
atgaccctga ggacccaggg caagaaacta atgtgtctat gtctttcatt tggcagtctg   1560
ccccagacat tggagaaag ttagagaggt tagaagattt aaaaaacaag acgcttggag    1620
atttggttag agaggcagaa aagatcttta ataaacgaga accccggaa gaaagagagg    1680 aacgtatcag gagagaaaca gaggaaaaag aagaacgccg taggacagag gatgagcaga    1740
aagagaaaga aagagatcgt aggagacata gagagatgag caagctattg gccactgtcg    1800
ttagtggaca gaaacaggat agacaggag gagaacgaag gaggtcccaa ctcgatcgcg     1860
accagtgtgc ctactgcaaa gaaaagggc actgggctaa agattgtccc aagaaccac      1920 gaggacctcg ggaccaaga ccccagacct ccctcctgac cctagatgac tagggaggtc     1980
```

```
agggtcagga gccccccct gaacccagga taaccctcaa agtcgggggg caacccgtca   2040
ccttcctggt agatactggg gcccaacact ccgtgctgac ccaaaatcct ggacccctaa   2100
gtgataagtc tgcctgggtc caaggggcta ctggaggaaa gcggtatcgc tggaccacgg   2160
atcgcaaagt acatctagct accggtaagg tcacccactc tttcctccat gtaccagact   2220
gtccctatcc tctgttagga agagatttgc tgactaaact aaaagcccaa atccactttg   2280
agggatcagg agctcaggtt atgggaccaa tggggcagcc cctgcaagtg ttgaccctaa   2340
atatagaaga tgagcatcgg ctacatgaga cctcaaaaga gccagatgtt tctctagggt   2400
ccacatggct gtctgatttt cctcaggcct gggcggaaac cggggcatg ggactggcag    2460 ttcgccaagc tcctctgatc atacctctga aagcaacctc taccccgtg tccataaaac    2520 aatacccat gtcacaagaa gccagactgg ggatcaagcc ccacatacag agactgttgg    2580
accagggaat actggtaccc tgccagtccc cctggaacac gcccctgcta cccgttaaga   2640
aaccagggac taatgattat aggcctgtcc aggatctgag agaagtcaac aagcgggtgg   2700
aagacatcca ccccaccgtg cccaacccttt acaacctctt gagcgggctc ccaccgtccc  2760
accagtggta cactgtgctt gatttaaagg atgcctttt ctgcctgaga ctccaccca    2820 ccagtcagcc tctcttcgcc tttgagtgga gagatccaga gatgggaatc tcaggacaat   2880
tgacctggac cagactccca cagggtttca aaaacagtcc caccctgttt gatgaggcac   2940
tgcacagaga cctagcagac ttccggatcc agcaccagga cttgatcctg ctacagtacg   3000
tggatgactt actgctggcc gccacttctg agctagactg ccaacaaggt actcgggccc   3060
tgttacaaac cctagggaac ctcgggtatc gggcctcggc caagaaagcc caaatttgcc   3120
agaaacaggt caagtatctg gggtatcttc taaaagaggg tcagagatgg ctgactgagg   3180
ccagaaaaga gactgtgatg gggcagccta ctccgaagac ccctcgacaa ctaagggagt   3240
tcctagggac ggcaggcttc tgtcgcctct ggatccctgg gtttgcagaa atggcagccc   3300
ccttgtaccc tctcaccaaa acggggactc tgtttaattg gggcccagac caacaaaagg   3360
cctatcaaga aatcaagcaa gctcttctaa ctgccccagc cctggggttg ccagatttga   3420
ctaagccctt tgaactcttt gtcgacgaga agcagggcta cgccaaaggt gtcctaacgc   3480
aaaaactggg accttggcgt cggccggtgg cctacctgtc caaaaagcta gacccagtag   3540
cagctgggtg gcccccttgc ctacggatgg tagcagccat tgccgtactg acaaaggatg   3600
caggcaagct aaccatggga cagccactag tcattctggc cccccatgca gtagaggcac   3660
tagtcaaaca ccccccgac cgctggcttt ccaacgcccg gatgactcac tatcaggcct    3720
tgcttttgga cacggaccgg gtccagttcg gaccggtggt agccctgaac ccggctacgc   3780
tgctcccact gcctgaggaa gggctgcaac acaactgcct tgatatcctg gccgaagccc   3840
acggaacccg acccgaccta acggaccagc cgctcccaga cgccgaccac acctggtaca   3900
cggatggaag cagtctctta caagagggac agcgtaaggc gggagctgcg gtgaccaccg   3960
agaccgaggt aatctggget aaagccetge cageeggaca ateegeteag cgggetgaac   4020 tgatagcact cacccaggcc ctaaagatgg cagaaggtaa gaagctaaat gtttatactg   4080
atagccgtta tgcttttgct actgcccata tccatggaga aatatacaga aggcgtgggt   4140
tgctcacatc agaaggcaaa gagatcaaaa ataaagacga gatcttggcc ctactaaaag   4200
ccctcttcct gcccaaaaga cttagcataa tccattgtcc aggacatcaa aagggacaca   4260
gcgccgaggc tagaggcaac cggatggctg accaagcggc ccgaaaggca gccatcacag   4320
```

```
agactccaga cacctctacc ctcctcatag aaaattcatc accctacacc tcagaacatt      4380
ttcattacac agtgactgat ataaaggacc taaccaagtt gggggccatt tatgataaaa      4440
caaagaagta ttgggtctac caaggaaaac ctgtgatgcc tgaccagttt acttttgaat      4500
tattagactt tcttcatcag ctgactcacc tcagcttctc aaaaatgaag gctctcctag      4560
agagaagcca cagtccctac tacatgctga accgggatcg aacactcaaa atatcactg       4620 agacctgcaa agcttgtgca caagtcaacg ccagcaagtc tgccgttaaa cagggaacta     4680
gggtccgcgg gcatcggccc ggcactcatt gggagatcga tttcaccgag ataaagcccg      4740
gattgtatgg ctataaatat cttctagttt ttatagatac ctttctggc tggatagaag       4800 ccttcccaac caagaaagaa accgccaagg tcgtaaccaa gaagctacta gaggagatct      4860
tccccaggtt cggcatgcct caggtattgg gaactgacaa tgggcctgcc ttcgtctcca      4920
aggtgagtca gacagtggcc gatctgttgg ggattgattg gaaattacat tgtgcataca     4980
gaccccaaag ctcaggccag gtagaaagaa tgaatagaac catcaaggag acttttaacta   5040 aattaacgct tgcaactggc tctagagact gggtgctcct actccccttta gccctgtacc    5100 gagcccgcaa cacgccgggc ccccatggcc tcaccccata tgagatctta tatgggcac      5160 ccccgccct tgtaaacttc cctgaccctg acatgacaag agttactaac agccctctc       5220 tccaagctca cttacaggct ctctacttag tccagcacga agtctggaga cctctggcgg     5280
cagcctacca agaacaactg gaccgaccgg tggtacctca cccttaccga gtcggcgaca    5340
cagtgtgggt ccgccgacac cagactaaga acctagaacc tcgctggaaa ggaccttaca   5400
cagtcctgct gaccacccc accgccctca aagtagacgg catcgcagct tggatacacg     5460
ccgcccacgt gaaggctgcc gaccccgggg gtggaccatc ctctagactg acatggcgcg    5520
ttcaacgctc tcaaaaccc ttaaaaataa ggttaacccg cgaggccccc taatcccctt     5580
aattcttctg atgctcagag gggtcagtac tgcttcgccc ggctccagtc ctcatcaagt    5640
ctataatatc acctgggagg taaccaatgg agatcgggag acggtatggg caacttctgg    5700
caaccaccct ctgtggacct ggtggcctga ccttaccccca gatttatgta tgttagccca   5760
ccatggacca tcttattggg ggctagaata tcaatcccct ttttcttctc ccccggggcc    5820
cccttgttgc tcaggggggca gcagcccagg ctgttccaga gactgcgaag aaccttaac    5880 ctccctcacc cctcggtgca acactgcctg gaacagactc aagctagacc agacaactca    5940
taaatcaaat gagggatttt atgtttgccc cgggccccac cgcccccgag aatccaagtc    6000
atgtgggggt ccagactcct tctactgtgc ctattggggc tgtgagacaa ccggtagagc    6060
ttactggaag ccctcctcat catgggattt catcacagta aacaacaatc tcacctctga    6120
ccaggctgtc caggtatgca aagataataa gtggtgcaac cccttagtta ttcggtttac    6180
agacgccggg agacgggtta cttcctggac cacaggacat tactgggct tacgtttgta     6240 tgtctccgga caagatccag ggcttacatt tgggatccga ctcagatacc aaaatctagg    6300 acccgcgtc ccaataggc caaacccgt tctggcagac caacagccac tctccaagcc       6360
caaacctgtt aagtcgcctt cagtcaccaa accacccagt gggactcctc tctccctac     6420 ccaacttcca ccgggcgggaa cggaaaatag gctgctaaac ttagtagacg gagcctacca   6480
agccctcaac ctcaccagtc ctgacaaaac ccaagagtgc tggttgtgtc tagtagcggg    6540 accccctac tacgaagggg ttgccgtcct gggtacctac tccaaccata cctctgctcc     6600
agccaactgc tccgtggcct cccaacacaa gttgacccgt tccgaagtga ccggacaggg    6660
actctgcata ggagcagttc ccaaaacaca tcaggcccta tgtaatacca cccagacaag    6720
```

-continued

```
cagtcgaggg tcctattatc tagttgcccc tacaggtacc atgtgggctt gtagtaccgg    6780
gcttactcca tgcatctcca ccaccatact gaaccttacc actgattatt gtgttcttgt    6840
cgaactctgg ccaagagtca cctatcattc ccccagctat gtttacggcc tgtttgagag    6900
atccaaccga cacaaaagag aaccggtgtc gttaaccctg ccctattat tgggtggact     6960
aaccatgggg ggaattgccg ctggaatagg aacaggact actgctctaa tggccactca     7020
gcaattccag cagctccaag ccgcagtaca ggatgatctc agggaggttg aaaaatcaat    7080
ctctaaccta gaaaagtctc tcacttccct gtctgaagtt gtcctacaga atcgaagggg    7140
cctagacttg ttatttctaa aagaaggagg gctgtgtgct gctctaaaag aagaatgttg    7200
cttctatgcg gaccacacag gactagtgag agacagcatg gccaaattga gagagaggct    7260
taatcagaga cagaaactgt ttgagtcaac tcaaggatgg tttgagggac tgtttaacag    7320
atccccttgg tttaccacct tgatatctac cattatggga cccctcattg tactcctaat    7380
gatttgctc ttcggaccct gcattcttaa tcgattagtc caatttgtta aagacaggat    7440
atcagtggtc caggctctag ttttgactca acaatatcac cagctgaagc ctatagagta    7500
cgagccatag ataaaataaa agattttatt tagtctccag aaaaaggggg aatgaaaga    7560
ccccacctgt aggtttggca agctagctta agtaacgcca ttttgcaagg catggaaaaa    7620
tacataactg agaatagaga agttcagatc aaggtcagga acagatggaa cagctgaata    7680
tgggccaaac aggatatctg tggtaagcag ttcctgcccc ggctcagggc caagaacaga    7740
tggaacagct gaatatgggc caaacaggat atctgtggta agcagttcct gccccggctc    7800
agggccaaga acagatggtc cccagatgcg gtccagccct cagcagtttc tagagaacca    7860
tcagatgttt ccagggtgcc ccaaggacct gaaatgaccc tgtgccttat ttgaactaac    7920
caatcagttc gcttctcgct tctgttcgcg cgcttctgct ccccgagctc aataaaagag    7980
cccacaaccc ctcactcggg gcgccagtcc tccgattgac tgagtcgccc gggtacccgt    8040
gtatccaata aaccctcttg cagttgcagc gccagtcctc cgattgactg agtcgcccgg    8100
gtacccgtgt atccaataaa ccctcttgca gttgcatccg acttgtggtc tcgctgttcc    8160
ttgggagggt ctcctctgag tgattgacta cccgtcagcg gggtctttc atttgggggc    8220
tcgtccggga tcgggagacc cctgcccagg gaccaccgac ccaccaccgg gaggtaagct    8280
ggccagcaac ttatctgtgt ctgtccgatt gtctagtgtc tatgactgat tt            8332
```

<210> SEQ ID NO 12
<211> LENGTH: 538
<212> TYPE: PRT
<213> ORGANISM: Moloney murine leukemia virus
<220> FEATURE:
<223> OTHER INFORMATION: gag protein

<400> SEQUENCE: 12

```
Met Gly Gln Thr Val Thr Thr Pro Leu Ser Leu Thr Leu Gly His Trp
  1               5                  10                  15

Lys Asp Val Glu Arg Ile Ala His Asn Gln Ser Val Asp Val Lys Lys
             20                  25                  30

Arg Arg Trp Val Thr Phe Cys Ser Ala Glu Trp Pro Thr Phe Asn Val
         35                  40                  45

Gly Trp Pro Arg Asp Gly Thr Phe Asn Arg Asp Leu Ile Thr Gln Val
     50                  55                  60

Lys Ile Lys Val Phe Ser Pro Gly Pro His Gly His Pro Asp Gln Val
 65                  70                  75                  80
```

```
Pro Tyr Ile Val Thr Trp Glu Ala Leu Ala Phe Asp Pro Pro Trp
                85                  90                  95
Val Lys Pro Phe Val His Pro Lys Pro Pro Pro Leu Pro Pro Ser
            100                 105                 110
Ala Pro Ser Leu Pro Leu Glu Pro Pro Arg Ser Thr Pro Pro Arg Ser
        115                 120                 125
Ser Leu Tyr Pro Ala Leu Thr Pro Ser Leu Gly Ala Lys Pro Lys Pro
    130                 135                 140
Gln Val Leu Ser Asp Ser Gly Pro Leu Ile Asp Leu Leu Thr Glu
145                 150                 155                 160
Asp Pro Pro Tyr Arg Asp Pro Arg Pro Pro Ser Asp Arg Asp
                165                 170                 175
Gly Asn Gly Gly Glu Ala Thr Pro Ala Gly Glu Ala Pro Asp Pro Ser
                180                 185                 190
Pro Met Ala Ser Arg Leu Arg Gly Arg Glu Pro Pro Val Ala Asp
        195                 200                 205
Ser Thr Thr Ser Gln Ala Phe Pro Leu Arg Ala Gly Gly Asn Gly Gln
    210                 215                 220
Leu Gln Tyr Trp Pro Phe Ser Ser Ser Asp Leu Tyr Asn Trp Lys Asn
225                 230                 235                 240
Asn Asn Pro Ser Phe Ser Glu Asp Pro Gly Lys Leu Thr Ala Leu Ile
                245                 250                 255
Glu Ser Val Leu Ile Thr His Gln Pro Thr Trp Asp Asp Cys Gln Gln
            260                 265                 270
Leu Leu Gly Thr Leu Leu Thr Gly Glu Glu Lys Gln Arg Val Leu Leu
            275                 280                 285
Glu Ala Arg Lys Ala Val Arg Gly Asp Asp Gly Arg Pro Thr Gln Leu
290                 295                 300
Pro Asn Glu Val Asp Ala Ala Phe Pro Leu Glu Arg Pro Asp Trp Asp
305                 310                 315                 320
Tyr Thr Thr Gln Ala Gly Arg Asn His Leu Val His Tyr Arg Gln Leu
                325                 330                 335
Leu Leu Ala Gly Leu Gln Asn Ala Gly Arg Ser Pro Thr Asn Leu Ala
            340                 345                 350
Lys Val Lys Gly Ile Thr Gln Gly Pro Asn Glu Ser Pro Ser Ala Phe
            355                 360                 365
Leu Glu Arg Leu Lys Glu Ala Tyr Arg Arg Tyr Thr Pro Tyr Asp Pro
        370                 375                 380
Glu Asp Pro Gly Gln Glu Thr Asn Val Ser Met Ser Phe Ile Trp Gln
385                 390                 395                 400
Ser Ala Pro Asp Ile Gly Arg Lys Leu Glu Arg Leu Glu Asp Leu Lys
            405                 410                 415
Asn Lys Thr Leu Gly Asp Leu Val Arg Glu Ala Glu Lys Ile Phe Asn
            420                 425                 430
Lys Arg Glu Thr Pro Glu Glu Arg Glu Arg Ile Arg Arg Glu Thr
        435                 440                 445
Glu Glu Lys Glu Glu Arg Arg Arg Thr Glu Asp Glu Gln Lys Glu Lys
    450                 455                 460
Glu Arg Asp Arg Arg Arg His Arg Glu Met Ser Lys Leu Leu Ala Thr
465                 470                 475                 480
Val Val Ser Gly Gln Lys Gln Asp Arg Gln Gly Gly Glu Arg Arg Arg
            485                 490                 495
```

```
Ser Gln Leu Asp Arg Asp Gln Cys Ala Tyr Cys Lys Glu Lys Gly His
             500                 505                 510

Trp Ala Lys Asp Cys Pro Lys Lys Pro Arg Gly Pro Arg Gly Pro Arg
         515                 520                 525

Pro Gln Thr Ser Leu Leu Thr Leu Asp Asp
     530                 535
```

<210> SEQ ID NO 13
<211> LENGTH: 1737
<212> TYPE: PRT
<213> ORGANISM: Moloney murine leukemia virus
<220> FEATURE:
<223> OTHER INFORMATION: gag-pol protein

<400> SEQUENCE: 13

```
Met Gly Gln Thr Val Thr Thr Pro Leu Ser Leu Thr Leu Gly His Trp
  1               5                  10                  15

Lys Asp Val Glu Arg Ile Ala His Asn Gln Ser Val Asp Val Lys Lys
             20                  25                  30

Arg Arg Trp Val Thr Phe Cys Ser Ala Glu Trp Pro Thr Phe Asn Val
         35                  40                  45

Gly Trp Pro Arg Asp Gly Thr Phe Asn Arg Asp Leu Ile Thr Gln Val
     50                  55                  60

Lys Ile Lys Val Phe Ser Pro Gly Pro His Gly His Pro Asp Gln Val
 65                  70                  75                  80

Pro Tyr Ile Val Thr Trp Glu Ala Leu Ala Phe Asp Pro Pro Pro Trp
                 85                  90                  95

Val Lys Pro Phe Val His Pro Lys Pro Pro Pro Leu Pro Pro Ser
             100                 105                 110

Ala Pro Ser Leu Pro Leu Glu Pro Pro Arg Ser Thr Pro Pro Arg Ser
         115                 120                 125

Ser Leu Tyr Pro Ala Leu Thr Pro Ser Leu Gly Ala Lys Pro Lys Pro
     130                 135                 140

Gln Val Leu Ser Asp Ser Gly Gly Pro Leu Ile Asp Leu Leu Thr Glu
145                 150                 155                 160

Asp Pro Pro Pro Tyr Arg Asp Pro Arg Pro Pro Pro Ser Asp Arg Asp
                 165                 170                 175

Gly Asn Gly Gly Glu Ala Thr Pro Ala Gly Glu Ala Pro Asp Pro Ser
             180                 185                 190

Pro Met Ala Ser Arg Leu Arg Gly Arg Arg Glu Pro Pro Val Ala Asp
         195                 200                 205

Ser Thr Thr Ser Gln Ala Phe Pro Leu Arg Ala Gly Gly Asn Gly Gln
     210                 215                 220

Leu Gln Tyr Trp Pro Phe Ser Ser Ser Asp Leu Tyr Asn Trp Lys Asn
225                 230                 235                 240

Asn Asn Pro Ser Phe Ser Glu Asp Pro Gly Lys Leu Thr Ala Leu Ile
                 245                 250                 255

Glu Ser Val Leu Ile Thr His Gln Pro Thr Trp Asp Asp Cys Gln Gln
             260                 265                 270

Leu Leu Gly Thr Leu Leu Thr Gly Glu Glu Lys Gln Arg Val Leu Leu
         275                 280                 285

Glu Ala Arg Lys Ala Val Arg Gly Asp Asp Gly Arg Pro Thr Gln Leu
     290                 295                 300

Pro Asn Glu Val Asp Ala Ala Phe Pro Leu Glu Arg Pro Asp Trp Asp
305                 310                 315                 320
```

-continued

```
Tyr Thr Thr Gln Ala Gly Arg Asn His Leu Val His Tyr Arg Gln Leu
            325                 330                 335

Leu Leu Ala Gly Leu Gln Asn Ala Gly Arg Ser Pro Thr Asn Leu Ala
            340                 345                 350

Lys Val Lys Gly Ile Thr Gln Gly Pro Asn Glu Ser Pro Ser Ala Phe
            355                 360                 365

Leu Glu Arg Leu Lys Glu Ala Tyr Arg Arg Tyr Thr Pro Tyr Asp Pro
    370                 375                 380

Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Lys
                405                 410                 415

Asn Lys Thr Leu Gly Asp Leu Val Arg Glu Ala Glu Lys Ile Phe Asn
            420                 425                 430

Lys Arg Glu Thr Pro Glu Glu Arg Glu Arg Ile Arg Arg Glu Thr
            435                 440                 445

Glu Glu Lys Glu Glu Arg Arg Thr Glu Asp Glu Gln Lys Glu Lys
    450                 455                 460

Glu Arg Asp Arg Arg Arg His Arg Glu Met Ser Lys Leu Leu Ala Thr
465                 470                 475                 480

Val Val Ser Gly Gln Lys Gln Asp Arg Gln Gly Gly Glu Arg Arg Arg
                485                 490                 495

Ser Gln Leu Asp Arg Asp Gln Cys Ala Tyr Cys Lys Glu Lys Gly His
                500                 505                 510

Trp Ala Lys Asp Cys Pro Lys Lys Pro Arg Gly Pro Arg Gly Pro Arg
            515                 520                 525

Pro Gln Thr Ser Leu Leu Thr Leu Asp Asp Gly Gly Gln Gly Gln Glu
    530                 535                 540

Pro Pro Pro Glu Pro Arg Ile Thr Leu Lys Val Gly Gly Gln Pro Val
545                 550                 555                 560

Thr Phe Leu Val Asp Thr Gly Ala Gln His Ser Val Leu Thr Gln Asn
                565                 570                 575

Pro Gly Pro Leu Ser Asp Lys Ser Ala Trp Val Gln Gly Ala Thr Gly
            580                 585                 590

Gly Lys Arg Tyr Arg Trp Thr Thr Asp Arg Lys Val His Leu Ala Thr
    595                 600                 605

Gly Lys Val Thr His Ser Phe Leu His Val Pro Asp Cys Pro Tyr Pro
610                 615                 620

Leu Leu Gly Arg Asp Leu Leu Thr Lys Leu Lys Ala Gln Ile His Phe
625                 630                 635                 640

Glu Gly Ser Gly Ala Gln Val Met Gly Pro Met Gly Gln Pro Leu Gln
                645                 650                 655

Val Leu Thr Leu Asn Ile Glu Asp Glu His Arg Leu His Glu Thr Ser
            660                 665                 670

Lys Glu Pro Asp Val Ser Leu Gly Ser Thr Trp Leu Ser Asp Phe Pro
    675                 680                 685

Gln Ala Trp Ala Glu Thr Gly Gly Met Gly Leu Ala Val Arg Gln Ala
690                 695                 700

Pro Leu Ile Ile Pro Leu Lys Ala Thr Ser Thr Pro Val Ser Ile Lys
705                 710                 715                 720

Gln Tyr Pro Met Ser Gln Glu Ala Arg Leu Gly Ile Lys Pro His Ile
                725                 730                 735

Gln Arg Leu Leu Asp Gln Gly Ile Leu Val Pro Cys Gln Ser Pro Trp
```

-continued

```
                740                 745                 750
Asn Thr Pro Leu Leu Pro Val Lys Lys Pro Gly Thr Asn Asp Tyr Arg
            755                 760                 765
Pro Val Gln Asp Leu Arg Glu Val Asn Lys Arg Val Glu Asp Ile His
        770                 775                 780
Pro Thr Val Pro Asn Pro Tyr Asn Leu Leu Ser Gly Leu Pro Pro Ser
785                 790                 795                 800
His Gln Trp Tyr Thr Val Leu Asp Leu Lys Asp Ala Phe Phe Cys Leu
                805                 810                 815
Arg Leu His Pro Thr Ser Gln Pro Leu Phe Ala Phe Glu Trp Arg Asp
            820                 825                 830
Pro Glu Met Gly Ile Ser Gly Gln Leu Thr Trp Thr Arg Leu Pro Gln
        835                 840                 845
Gly Phe Lys Asn Ser Pro Thr Leu Phe Asp Glu Ala Leu His Arg Asp
850                 855                 860
Leu Ala Asp Phe Arg Ile Gln His Pro Asp Leu Ile Leu Leu Gln Tyr
865                 870                 875                 880
Val Asp Asp Leu Leu Ala Ala Thr Ser Glu Leu Asp Cys Gln Gln
                885                 890                 895
Gly Thr Arg Ala Leu Leu Gln Thr Leu Gly Asn Leu Gly Tyr Arg Ala
            900                 905                 910
Ser Ala Lys Lys Ala Gln Ile Cys Gln Lys Gln Val Lys Tyr Leu Gly
        915                 920                 925
Tyr Leu Leu Lys Glu Gly Gln Arg Trp Leu Thr Glu Ala Arg Lys Glu
        930                 935                 940
Thr Val Met Gly Gln Pro Thr Pro Lys Thr Pro Arg Gln Leu Arg Glu
945                 950                 955                 960
Phe Leu Gly Thr Ala Gly Phe Cys Arg Leu Trp Ile Pro Gly Phe Ala
                965                 970                 975
Glu Met Ala Ala Pro Leu Tyr Pro Leu Thr Lys Thr Gly Thr Leu Phe
            980                 985                 990
Asn Trp Gly Pro Asp Gln Gln Lys Ala Tyr Gln Glu Ile Lys Gln Ala
        995                 1000                1005
Leu Leu Thr Ala Pro Ala Leu Gly Leu Pro Asp Leu Thr Lys Pro Phe
    1010                1015                1020
Glu Leu Phe Val Asp Glu Lys Gln Gly Tyr Ala Lys Gly Val Leu Thr
1025                1030                1035                1040
Gln Lys Leu Gly Pro Trp Arg Arg Pro Val Ala Tyr Leu Ser Lys Lys
                1045                1050                1055
Leu Asp Pro Val Ala Ala Gly Trp Pro Pro Cys Leu Arg Met Val Ala
            1060                1065                1070
Ala Ile Ala Val Leu Thr Lys Asp Ala Gly Lys Leu Thr Met Gly Gln
        1075                1080                1085
Pro Leu Val Ile Leu Ala Pro His Ala Val Glu Ala Leu Val Lys Gln
    1090                1095                1100
Pro Pro Asp Arg Trp Leu Ser Asn Ala Arg Met Thr His Tyr Gln Ala
1105                1110                1115                1120
Leu Leu Leu Asp Thr Asp Arg Val Gln Phe Gly Pro Val Val Ala Leu
                1125                1130                1135
Asn Pro Ala Thr Leu Leu Pro Leu Pro Glu Glu Gly Leu Gln His Asn
            1140                1145                1150
Cys Leu Asp Ile Leu Ala Glu Ala His Gly Thr Arg Pro Asp Leu Thr
        1155                1160                1165
```

-continued

```
Asp Gln Pro Leu Pro Asp Ala Asp His Thr Trp Tyr Thr Asp Gly Ser
    1170                1175                1180

Ser Leu Leu Gln Glu Gly Gln Arg Lys Ala Gly Ala Ala Val Thr Thr
1185                1190                1195                1200

Glu Thr Glu Val Ile Trp Ala Lys Ala Leu Pro Ala Gly Thr Ser Ala
        1205                1210                1215

Gln Arg Ala Glu Leu Ile Ala Leu Thr Gln Ala Leu Lys Met Ala Glu
        1220                1225                1230

Gly Lys Lys Leu Asn Val Tyr Thr Asp Ser Arg Tyr Ala Phe Ala Thr
        1235                1240                1245

Ala His Ile His Gly Glu Ile Tyr Arg Arg Gly Leu Leu Thr Ser
        1250                1255                1260

Glu Gly Lys Glu Ile Lys Asn Lys Asp Glu Ile Leu Ala Leu Leu Lys
1265                1270                1275                1280

Ala Leu Phe Leu Pro Lys Arg Leu Ser Ile Ile His Cys Pro Gly His
        1285                1290                1295

Gln Lys Gly His Ser Ala Glu Ala Arg Gly Asn Arg Met Ala Asp Gln
        1300                1305                1310

Ala Ala Arg Lys Ala Ala Ile Thr Glu Thr Pro Asp Thr Ser Thr Leu
        1315                1320                1325

Leu Ile Glu Asn Ser Ser Pro Tyr Thr Ser Glu His Phe His Tyr Thr
        1330                1335                1340

Val Thr Asp Ile Lys Asp Leu Thr Lys Leu Gly Ala Ile Tyr Asp Lys
1345                1350                1355                1360

Thr Lys Lys Tyr Trp Val Tyr Gln Gly Lys Pro Val Met Pro Asp Gln
        1365                1370                1375

Phe Thr Phe Glu Leu Leu Asp Phe Leu His Gln Leu Thr His Leu Ser
        1380                1385                1390

Phe Ser Lys Met Lys Ala Leu Leu Glu Arg Ser His Ser Pro Tyr Tyr
        1395                1400                1405

Met Leu Asn Arg Asp Arg Thr Leu Lys Asn Ile Thr Glu Thr Cys Lys
    1410                1415                1420

Ala Cys Ala Gln Val Asn Ala Ser Lys Ser Ala Val Lys Gln Gly Thr
1425                1430                1435                1440

Arg Val Arg Gly His Arg Pro Gly Thr His Trp Glu Ile Asp Phe Thr
        1445                1450                1455

Glu Ile Lys Pro Gly Leu Tyr Gly Tyr Lys Tyr Leu Leu Val Phe Ile
        1460                1465                1470

Asp Thr Phe Ser Gly Trp Ile Glu Ala Phe Pro Thr Lys Lys Glu Thr
        1475                1480                1485

Ala Lys Val Val Thr Lys Lys Leu Leu Glu Glu Ile Phe Pro Arg Phe
    1490                1495                1500

Gly Met Pro Gln Val Leu Gly Thr Asp Asn Gly Pro Ala Phe Val Ser
1505                1510                1515                1520

Lys Val Ser Gln Thr Val Ala Asp Leu Leu Gly Ile Asp Trp Lys Leu
        1525                1530                1535

His Cys Ala Tyr Arg Pro Gln Ser Ser Gly Gln Val Glu Arg Met Asn
        1540                1545                1550

Arg Thr Ile Lys Glu Thr Leu Thr Lys Leu Thr Leu Ala Thr Gly Ser
    1555                1560                1565

Arg Asp Trp Val Leu Leu Leu Pro Leu Ala Leu Tyr Arg Ala Arg Asn
    1570                1575                1580
```

-continued

```
Thr Pro Gly Pro His Gly Leu Thr Pro Tyr Glu Ile Leu Tyr Gly Ala
1585                1590                1595                1600

Pro Pro Pro Leu Val Asn Phe Pro Asp Pro Asp Met Thr Arg Val Thr
            1605                1610                1615

Asn Ser Pro Ser Leu Gln Ala His Leu Gln Ala Leu Tyr Leu Val Gln
        1620                1625                1630

His Glu Val Trp Arg Pro Leu Ala Ala Ala Tyr Gln Glu Gln Leu Asp
        1635                1640                1645

Arg Pro Val Val Pro His Pro Tyr Arg Val Gly Asp Thr Val Trp Val
    1650                1655                1660

Arg Arg His Gln Thr Lys Asn Leu Glu Pro Arg Trp Lys Gly Pro Tyr
1665                1670                1675                1680

Thr Val Leu Leu Thr Thr Pro Thr Ala Leu Lys Val Asp Gly Ile Ala
                1685                1690                1695

Ala Trp Ile His Ala Ala His Val Lys Ala Ala Asp Pro Gly Gly Gly
                1700                1705                1710

Pro Ser Ser Arg Leu Thr Trp Arg Val Gln Arg Ser Gln Asn Pro Leu
            1715                1720                1725

Lys Ile Arg Leu Thr Arg Glu Ala Pro
    1730                1735
```

<210> SEQ ID NO 14
<211> LENGTH: 665
<212> TYPE: PRT
<213> ORGANISM: Moloney murine leukemia virus
<220> FEATURE:
<223> OTHER INFORMATION: env protein

<400> SEQUENCE: 14

```
Met Ala Arg Ser Thr Leu Ser Lys Pro Leu Lys Asn Lys Val Asn Pro
 1               5                  10                  15

Arg Gly Pro Leu Ile Pro Leu Ile Leu Leu Met Leu Arg Gly Val Ser
                20                  25                  30

Thr Ala Ser Pro Gly Ser Ser Pro His Gln Val Tyr Asn Ile Thr Trp
            35                  40                  45

Glu Val Thr Asn Gly Asp Arg Glu Thr Val Trp Ala Thr Ser Gly Asn
    50                  55                  60

His Pro Leu Trp Thr Trp Trp Pro Asp Leu Thr Pro Asp Leu Cys Met
65                  70                  75                  80

Leu Ala His His Gly Pro Ser Tyr Trp Gly Leu Glu Tyr Gln Ser Pro
                85                  90                  95

Phe Ser Ser Pro Pro Gly Pro Pro Cys Cys Ser Gly Gly Ser Ser Pro
            100                 105                 110

Gly Cys Ser Arg Asp Cys Glu Glu Pro Leu Thr Ser Leu Thr Pro Arg
        115                 120                 125

Cys Asn Thr Ala Trp Asn Arg Leu Lys Leu Asp Gln Thr Thr His Lys
    130                 135                 140

Ser Asn Glu Gly Phe Tyr Val Cys Pro Gly Pro His Arg Pro Arg Glu
145                 150                 155                 160

Ser Lys Ser Cys Gly Gly Pro Asp Ser Phe Tyr Cys Ala Tyr Trp Gly
                165                 170                 175

Cys Glu Thr Thr Gly Arg Ala Tyr Trp Lys Pro Ser Ser Ser Trp Asp
            180                 185                 190

Phe Ile Thr Val Asn Asn Asn Leu Thr Ser Asp Gln Ala Val Gln Val
        195                 200                 205
```

-continued

```
Cys Lys Asp Asn Lys Trp Cys Asn Pro Leu Val Ile Arg Phe Thr Asp
    210                 215                 220
Ala Gly Arg Arg Val Thr Ser Trp Thr Thr Gly His Tyr Trp Gly Leu
225                 230                 235                 240
Arg Leu Tyr Val Ser Gly Gln Asp Pro Gly Leu Thr Phe Gly Ile Arg
                245                 250                 255
Leu Arg Tyr Gln Asn Leu Gly Pro Arg Val Pro Ile Gly Pro Asn Pro
            260                 265                 270
Val Leu Ala Asp Gln Gln Pro Leu Ser Lys Pro Lys Pro Val Lys Ser
        275                 280                 285
Pro Ser Val Thr Lys Pro Pro Ser Gly Thr Pro Leu Ser Pro Thr Gln
    290                 295                 300
Leu Pro Pro Ala Gly Thr Glu Asn Arg Leu Leu Asn Leu Val Asp Gly
305                 310                 315                 320
Ala Tyr Gln Ala Leu Asn Leu Thr Ser Pro Asp Lys Thr Gln Glu Cys
                325                 330                 335
Trp Leu Cys Leu Val Ala Gly Pro Pro Tyr Tyr Glu Gly Val Ala Val
            340                 345                 350
Leu Gly Thr Tyr Ser Asn His Thr Ser Ala Pro Ala Asn Cys Ser Val
        355                 360                 365
Ala Ser Gln His Lys Leu Thr Leu Ser Glu Val Thr Gly Gln Gly Leu
    370                 375                 380
Cys Ile Gly Ala Val Pro Lys Thr His Gln Ala Leu Cys Asn Thr Thr
385                 390                 395                 400
Gln Thr Ser Ser Arg Gly Ser Tyr Tyr Leu Val Ala Pro Thr Gly Thr
                405                 410                 415
Met Trp Ala Cys Ser Thr Gly Leu Thr Pro Cys Ile Ser Thr Thr Ile
            420                 425                 430
Leu Asn Leu Thr Thr Asp Tyr Cys Val Leu Val Glu Leu Trp Pro Arg
        435                 440                 445
Val Thr Tyr His Ser Pro Ser Tyr Val Tyr Gly Leu Phe Glu Arg Ser
    450                 455                 460
Asn Arg His Lys Arg Glu Pro Val Ser Leu Thr Leu Ala Leu Leu Leu
465                 470                 475                 480
Gly Gly Leu Thr Met Gly Gly Ile Ala Ala Gly Ile Gly Thr Gly Thr
                485                 490                 495
Thr Ala Leu Met Ala Thr Gln Gln Phe Gln Gln Leu Gln Ala Ala Val
            500                 505                 510
Gln Asp Asp Leu Arg Glu Val Glu Lys Ser Ile Ser Asn Leu Glu Lys
        515                 520                 525
Ser Leu Thr Ser Leu Ser Glu Val Val Leu Gln Asn Arg Arg Gly Leu
    530                 535                 540
Asp Leu Leu Phe Leu Lys Glu Gly Gly Leu Cys Ala Ala Leu Lys Glu
545                 550                 555                 560
Glu Cys Cys Phe Tyr Ala Asp His Thr Gly Leu Val Arg Asp Ser Met
                565                 570                 575
Ala Lys Leu Arg Glu Arg Leu Asn Gln Arg Gln Lys Leu Phe Glu Ser
            580                 585                 590
Thr Gln Gly Trp Phe Glu Gly Leu Phe Asn Arg Ser Pro Trp Phe Thr
        595                 600                 605
Thr Leu Ile Ser Thr Ile Met Gly Pro Leu Ile Val Leu Leu Met Ile
    610                 615                 620
Leu Leu Phe Gly Pro Cys Ile Leu Asn Arg Leu Val Gln Phe Val Lys
```

-continued

```
        625                 630                 635                 640
Asp Arg Ile Ser Val Val Gln Ala Leu Val Leu Thr Gln Gln Tyr His
                    645                 650                 655

Gln Leu Lys Pro Ile Glu Tyr Glu Pro
            660                 665

<210> SEQ ID NO 15
<211> LENGTH: 9709
<212> TYPE: DNA
<213> ORGANISM: Human immunodeficiency virus type 1

<400> SEQUENCE: 15
tggaagggct aatttggtcc caaaaaagac aagagatcct tgatctgtgg atctaccaca      60
cacaaggcta cttccctgat tggcagaact acacaccagg gccagggatc agatatccac     120
tgacctttgg atggtgcttc aagttagtac cagttgaacc agagcaagta gaagaggcca     180 ataaggaga gaagaacagc ttgttacacc ctatgagcca gcatgggatg gaggacccgg      240
agggagaagt attagtgtgg aagtttgaca gcctcctagc atttcgtcac atggcccgag     300
agctgcatcc ggagtactac aaagactgct gacatcgagc tttctacaag ggactttccg     360
ctggggactt tccagggagg tgtggcctgg gcgggactgg ggagtggcga gccctcagat     420
gctacatata agcagctgct ttttgcctgt actgggtctc tctggttaga ccagatctga     480
gcctgggagc tctctggcta actagggaac ccactgctta agcctcaata agcttgcct      540 tgagtgctca agtagtgtg tgcccgtctg ttgtgtgact ctggtaacta gagatccctc      600
agaccctttt agtcagtgtg gaaaatctct agcagtggcg cccgaacagg acttgaaag      660 cgaaagtaaa gccagaggag atctctcgac gcaggactcg gcttgctgaa gcgcgcacgg     720
caagaggcga gggcggcga ctggtgagta cgccaaaaat tttgactagc ggaggctaga     780
aggagagaga tgggtgcgag agcgtcggta ttaagcgggg gagaattaga taatgggaa      840 aaaattcggt taaggccagg gggaagaaa caatataaac taaaacatat agtatgggca      900
agcagggagc tagaacgatt cgcagttaat cctggccttt tagagacatc agaaggctgt     960
agacaaatac tgggacagct acaaccatcc cttcagacag gatcagaaga acttagatca    1020
ttatataata caatagcagt cctctattgt gtgcatcaaa ggatagatgt aaaagacacc    1080
aaggaagcct tagataagat agaggaagag caaaacaaaa gtaagaaaaa ggcacagcaa    1140
gcagcagctg acacaggaaa caacagccag gtcagccaaa attaccctat agtgcagaac    1200 ctccagggc aaatggtaca tcaggccata tcacctagaa ctttaaatgc atgggtaaaa     1260
gtagtagaag agaaggcttt cagcccagaa gtaataccca tgttttcagc attatcagaa    1320
ggagccaccc cacaagattt aaataccatg ctaaacacag tggggggaca tcaagcagcc    1380
atgcaaatgt taaagagac catcaatgag gaagctgcag aatgggatag attgcatcca    1440
gtgcatgcag ggcctattgc accaggccag atgagagaac caaggggaag tgacatagca    1500
ggaactacta gtacccttca ggaacaaata ggatggatga cacataatcc acctatccca    1560
gtaggagaaa tctataaaag atggataatc ctgggattaa ataaaatagt aagaatgtat    1620
agccctacca gcattctgga cataagacaa ggaccaaagg aacccttag agactatgta    1680 gaccgattct ataaaactct aagagccgag caagcttcac aagaggtaaa aaattggatg    1740
acagaaacct tgttggtcca aaatgcgaac ccagattgta agactatttt aaaagcattg    1800
ggaccaggag cgacactaga agaaatgatg acagcatgtc agggagtggg gggacccggc    1860
cataaagcaa gagttttggc tgaagcaatg agccaagtaa caaatccagc taccataatg    1920
```

-continued

```
atacagaaag gcaattttag gaaccaaaga aagactgtta agtgtttcaa ttgtggcaaa    1980
gaagggcaca tagccaaaaa ttgcagggcc cctaggaaaa agggctgttg gaaatgtgga    2040
aaggaaggac accaaatgaa agattgtact gagagacagg ctaattttt agggaagatc     2100 tggccttccc acaagggaag gccagggaat tttcttcaga gcagaccaga gccaacagcc    2160
ccaccagaag agagcttcag gtttgggggaa gagacaacaa ctccctctca gaagcaggag   2220
ccgatagaca aggaactgta tcctttagct tccctcagat cactctttgg cagcgacccc    2280
tcgtcacaat aaagataggg gggcaattaa aggaagctct attagataca ggagcagatg    2340
atacagtatt agaagaaatg aatttgccag gaagatggaa accaaaaatg atagggggaa    2400
ttggaggttt tatcaaagta ggacagtatg atcagatact catagaaatc tgcggacata    2460
aagctatagg tacagtatta gtaggaccta cacctgtcaa cataattgga agaaatctgt    2520
tgactcagat tggctgcact ttaaattttc ccattagtcc tattgagact gtaccagtaa    2580
aattaaagcc aggaatggat ggcccaaaag ttaaacaatg gccattgaca gaagaaaaaa    2640
taaaagcatt agtagaaatt tgtacagaaa tggaaaagga aggaaaaatt tcaaaaattg    2700
ggcctgaaaa tccatacaat actccagtat ttgccataaa gaaaaaagac agtactaaat    2760
ggagaaaatt agtagatttc agagaactta ataagagaac tcaagatttc tgggaagttc    2820
aattaggaat accacatcct gcagggttaa aacagaaaaa atcagtaaca gtactggatg    2880
tgggcgatgc atatttttca gttcccttag ataaagactt caggaagtat actgcattta    2940
ccatacctag tataaacaat gagacaccag ggattagata tcagtacaat gtgcttccac    3000
agggatggaa aggatcacca gcaatattcc agtgtagcat gacaaaaatc ttagagcctt    3060
ttagaaaaca aaatccagac atagtcatct atcaatacat ggatgatttg tatgtaggat    3120
ctgacttaga aatagggcag catagaacaa aaatagagga actgagacaa catctgttga    3180
ggtggggatt taccacacca gacaaaaaac atcagaaaga acctccattc ctttggatgg    3240
gttatgaact ccatcctgat aaatggacag tacagcctat agtgctgcca gaaaaggaca    3300
gctggactgt caatgacata cagaaattag tgggaaaatt gaattgggca agtcagattt    3360
atgcagggat taaagtaagg caattatgta aacttcttag gggaaccaaa gcactaacag    3420
aagtagtacc actaacagaa gaagcagagc tagaactggc agaaaacagg gagattctaa    3480
aagaaccggt acatggagtg tattatgacc catcaaaaga cttaatagca gaaatacaga    3540 agcagggca aggccaatgg acatatcaaa tttatcaaga gccatttaaa aatctgaaaa    3600
caggaaaata tgcaagaatg aagggtgccc acactaatga tgtgaaacaa ttaacagagg    3660
cagtacaaaa aatagccaca gaaagcatag taatatgggg aaaagactcct aaatttaaat    3720 tacccataca aaaggaaaca tgggaagcat ggtggacaga gtattggcaa gccacctgga    3780
ttcctgagtg ggagtttgtc aatacccctc ccttagtgaa gttatggtac cagttagaga    3840
aagaacccat aataggagca gaaactttct atgtagatgg ggcagccaat agggaaacta    3900
aattaggaaa agcaggatat gtaactgaca gaggaagaca aaaagttgtc cccctaacgg    3960
acacaacaaa tcagaagact gagttacaag caattcatct agctttgcag gattcgggat    4020
tagaagtaaa catagtgaca gactcacaat atgcattggg aatcattcaa gcacaaccag    4080
ataagagtga atcagagtta gtcagtcaaa taatagagca gttaataaaa aaggaaaaag    4140
tctacctggc atgggtacca gcacacaaag gaattggagg aaatgaacaa gtagatgggt    4200
tggtcagtgc tggaatcagg aaagtactat ttttagatgg aatagataag gcccaagaag    4260
```

```
aacatgagaa atatcacagt aattggagag caatggctag tgattttaac ctaccacctg    4320
tagtagcaaa agaaatagta gccagctgtg ataaatgtca gctaaaaggg gaagccatgc    4380
atggacaagt agactgtagc ccaggaatat ggcagctaga ttgtacacat ttagaaggaa    4440
aagttatctt ggtagcagtt catgtagcca gtggatatat agaagcagaa gtaattccag    4500
cagagacagg gcaagaaaca gcatacttcc tcttaaaatt agcaggaaga tggccagtaa    4560
aaacagtaca tacagacaat ggcagcaatt tcaccagtac tacagttaag gccgcctgtt    4620
ggtgggcggg gatcaagcag gaatttggca ttccctacaa tccccaaagt caaggagtaa    4680
tagaatctat gaataaagaa ttaaagaaaa ttataggaca ggtaagagat caggctgaac    4740
atcttaagac agcagtacaa atggcagtat tcatccacaa ttttaaaaga aaaggggggga    4800 ttgggggggta cagtgcaggg gaaagaatag tagacataat agcaacagac atacaaacta    4860
aagaattaca aaaacaaatt acaaaaattc aaaattttcg ggtttattac agggacagca    4920
gagatccagt ttggaaagga ccagcaaagc tcctctggaa aggtgaaggg gcagtagtaa    4980
tacaagataa tagtgacata aaagtagtgc caagaagaaa agcaaagatc atcagggatt    5040
atggaaaaca gatggcaggt gatgattgtg tggcaagtag acaggatgag gattaacaca    5100
tggaaaagat tagtaaaaca ccatatgtat atttcaagga aagctaagga ctggttttat    5160
agacatcact atgaaagtac taatccaaaa ataagttcag aagtacacat cccactaggg    5220
gatgctaaat tagtaataac aacatattgg ggtctgcata caggagaaag agactggcat    5280
ttgggtcagg gagtctccat agaatggagg aaaaagagat atagcacaca agtagaccct    5340
gacctagcag accaactaat tcatctgcac tattttgatt gtttttcaga atctgctata    5400
agaaatacca tattaggacg tatagttagt cctaggtgtg aatatcaagc aggacataac    5460
aaggtaggat ctctacagta cttggcacta gcagcattaa taaaaccaaa acagataaag    5520
ccacctttgc ctagtgttag gaaactgaca gaggacagat ggaacaagcc ccagaagacc    5580
aagggccaca gagggagcca tacaatgaat ggacactaga gcttttagag gaacttaaga    5640
gtgaagctgt tagacatttt cctaggatat ggctccataa cttaggacaa catatctatg    5700
aaacttacgg ggatacttgg gcaggagtgg aagccataat aagaattctg caacaactgc    5760
tgtttatcca tttcagaatt gggtgtcgac atagcagaat aggcgttact cgacagagga    5820
gagcaagaaa tggagccagt agatcctaga ctagagccct ggaagcatcc aggaagtcag    5880
cctaaaactg cttgtaccaa ttgctattgt aaaaagtgtt gctttcattg ccaagtttgt    5940
ttcatgacaa aagccttagg catctcctat ggcaggaaga agcggagaca gcgacgaaga    6000
gctcatcaga acagtcagac tcatcaagct tctctatcaa agcagtaagt agtacatgta    6060
atgcaaccta taatagtagc aatagtagca ttagtagtag caataataat agcaatagtt    6120
gtgtggtcca tagtaatcat agaatatagg aaaatattaa gacaaagaaa atagacagg     6180 ttaattgata gactaataga aagagcagaa gacagtggca atgagagtga aggagaagta    6240
tcagcacttg tggagatggg ggtggaaatg gggcaccatg ctccttggga tattgatgat    6300
ctgtagtgct acagaaaaat tgtgggtcac agtctattat ggggtacctg tgtggaagga    6360
agcaaccacc actctatttt gtgcatcaga tgctaaagca tatgatacag aggtacataa    6420
tgtttgggcc acacatgcct gtgtacccac agaccccaac ccacaagaag tagtattggt    6480
aaatgtgaca gaaaatttta acatgtggaa aaatgacatg gtagaacaga tgcatgagga    6540
tataatcagt ttatgggatc aaagcctaaa gccatgtgta aaattaaccc cactctgtgt    6600 tagttttaaag tgcactgatt tgaagaatga tactaatacc aatagtagta gcgggagaat    6660
```

-continued

```
gataatggag aaaggagaga taaaaaactg ctctttcaat atcagcacaa gcataagaga    6720
taaggtgcag aaagaatatg cattcttttt a taaacttgat atagtaccaa tagataatac  6780
cagctatagg ttgataagtt gtaacacctc agtcattaca caggcctgtc caaaggtatc    6840
ctttgagcca attcccatac attattgtgc cccggctggt tttgcgattc taaaatgtaa    6900
taataagacg ttcaatggaa caggaccatg tacaaatgtc agcacagtac aatgtacaca    6960
tggaatcagg ccagtagtat caactcaact gctgttaaat ggcagtctag cagaagaaga    7020
tgtagtaatt agatctgcca atttcacaga caatgctaaa accataatag tacagctgaa    7080
cacatctgta gaattaatt gtacaagacc caacaacaat acaagaaaaa gtatccgtat      7140
ccagagggga ccagggagag catttgttac aataggaaaa ataggaaata tgagacaagc    7200
acattgtaac attagtagag caaaatggaa tgccactttt a aaacagatag ctagcaaatt  7260
aagagaacaa tttggaaata taaaacaat aatctttaag caatcctcag gaggggaccc      7320
agaaattgta acgcacagtt ttaattgtgg aggggaattt ttctactgta attcaacaca    7380 actgttaat agtacttggt ttaatagtac ttggagtact gaagggtcaa ataacactga      7440
aggaagtgac acaatcacac tcccatgcag aataaaacaa tttataaaca tgtggcagga    7500
agtaggaaaa gcaatgtatg cccctcccat cagtggacaa attagatgtt catcaaatat    7560
tactgggctg ctattaacaa gagatggtgg taataacaac aatgggtccg agatcttcag    7620
acctggagga ggcgatatga gggacaattg gagaagtgaa ttatataaat ataaagtagt    7680
aaaaattgaa ccattaggag tagcacccac caaggcaaag agaagagtgg tgcagagaga    7740
aaaaagagca gtgggaatag gagctttgtt ccttgggttc ttgggagcag caggaagcac    7800
tatgggctgc acgtcaatga cgctgacggt acaggccaga caattattgt ctgatatagt    7860
gcagcagcag aacaatttgc tgagggctat tgaggcgcaa cagcatctgt tgcaactcac    7920
agtctggggc atcaaacagc tccaggcaag aatcctggct gtggaaagat acctaaagga    7980
tcaacagctc ctggggattt ggggttgctc tggaaaactc atttgcacca ctgctgtgcc    8040
ttggaatgct agttggagta ataaatctct ggaacagatt tggaataaca tgacctggat    8100
ggagtgggac agagaaatta acaattacac aagcttaata cactccttaa ttgaagaatc    8160
gcaaaaccag caagaaaaga atgaacaaga attattggaa ttagataaat gggcaagttt    8220
gtggaattgg tttaacataa caattggct gtggtatata aaattattca taatgatagt      8280
aggaggcttg gtaggtttaa gaatagtttt tgctgtactt tctatagtga atagagttag    8340
gcagggatat tcaccattat cgtttcagac ccacctccca atcccgaggg gacccgacag    8400
gcccgaagga atagaagaag aagtggaga gagagacaga gacagatcca ttcgattagt      8460
gaacggatcc ttagcactta tctgggacga tctgcggagc ctgtgcctct tcagctacca    8520
ccgcttgaga gacttactct tgattgtaac gaggattgtg gaacttctgg gacgcagggg    8580 gtggaagcc ctcaaatatt ggtggaatct cctacagtat tggagtcagg aactaaagaa      8640
tagtgctgtt aacttgctca atgccacagc catagcagta gctgagggga cagatagggt    8700
tatagaagta ttacaagcag cttatagagc tattcgccac atacctagaa gaataagaca    8760
gggcttggaa aggattttgc tataagatgg gtggcaagtg gtcaaaaagt agtgtgattg    8820
gatggcctgc tgtaagggaa agaatgagac gagctgagcc agcagcagat ggggtgggag    8880
cagtatctcg agacctagaa aaacatggag caatcacaag tagcaataca gcagctaaca    8940
atgctgcttg tgcctggcta gaagcacaag aggaggaaga ggtgggtttt ccagtcacac    9000
```

-continued

```
ctcaggtacc tttaagacca atgacttaca aggcagctgt agatcttagc cacttttaa     9060 aagaaaaggg gggactggaa gggctaattc actcccaaag aagacaagat atccttgatc    9120
tgtggatcta ccacacacaa ggctacttcc ctgattggca gaactacaca ccagggccag    9180
gggtcagata tccactgacc tttggatggt gctacaagct agtaccagtt gagccagata    9240
aggtagaaga ggccaataaa ggagagaaca ccagcttgtt acaccctgtg agcctgcatg    9300
gaatggatga ccctgagaga gaagtgttag agtggaggtt tgacagccgc ctagcatttc    9360
atcacgtggc ccgagagctg catccggagt acttcaagaa ctgctgacat cgagcttgct    9420
acaagggact ttccgctggg gactttccag ggaggcgtgg cctgggcggg actggggagt    9480
ggcgagccct cagatgctgc atataagcag ctgcttttg cctgtactgg gtctctctgg    9540
ttagaccaga tctgagcctg ggagctctct ggctaactag gaacccact gcttaagcct    9600 caataaagct tgccttgagt gcttcaagta gtgtgtgccc gtctgttgtg tgactctggt    9660
aactagagat ccctcagacc cttttagtca gtgtggaaaa tctctagca               9709
```

<210> SEQ ID NO 16
<211> LENGTH: 500
<212> TYPE: PRT
<213> ORGANISM: Human immunodeficiency virus type 1
<220> FEATURE:
<223> OTHER INFORMATION: gag polyprotein

<400> SEQUENCE: 16

```
Met Gly Ala Arg Ala Ser Val Leu Ser Gly Gly Glu Leu Asp Lys Trp
  1               5                  10                  15

Glu Lys Ile Arg Leu Arg Pro Gly Gly Lys Lys Gln Tyr Lys Leu Lys
             20                  25                  30

His Ile Val Trp Ala Ser Arg Glu Leu Glu Arg Phe Ala Val Asn Pro
         35                  40                  45

Gly Leu Leu Glu Thr Ser Glu Gly Cys Arg Gln Ile Leu Gly Gln Leu
     50                  55                  60

Gln Pro Ser Leu Gln Thr Gly Ser Glu Glu Leu Arg Ser Leu Tyr Asn
 65                  70                  75                  80

Thr Ile Ala Val Leu Tyr Cys Val His Gln Arg Ile Asp Val Lys Asp
                 85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly Asn Asn Ser Gln Val
        115                 120                 125

Ser Gln Asn Tyr Pro Ile Val Gln Asn Leu Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240
```

```
Ser Thr Leu Gln Glu Gln Ile Gly Trp Met Thr His Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Pro Ala Thr Ile Met Ile Gln Lys Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser His Lys Gly Arg Pro Gly Asn Phe
        435                 440                 445

Leu Gln Ser Arg Pro Glu Pro Thr Ala Pro Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Leu Tyr Pro Leu Ala Ser Leu Arg Ser Leu Phe Gly Ser Asp
                485                 490                 495

Pro Ser Ser Gln
            500

<210> SEQ ID NO 17
<211> LENGTH: 1003
<212> TYPE: PRT
<213> ORGANISM: Human immunodeficiency virus type 1
<220> FEATURE:
<223> OTHER INFORMATION: pol polyprotein

<400> SEQUENCE: 17

Phe Phe Arg Glu Asp Leu Ala Phe Pro Gln Gly Lys Ala Arg Glu Phe
  1               5                  10                  15

Ser Ser Glu Gln Thr Arg Ala Asn Ser Pro Thr Arg Arg Glu Leu Gln
             20                  25                  30

Val Trp Gly Arg Asp Asn Ser Leu Ser Glu Ala Gly Ala Asp Arg
         35                  40                  45

Gln Gly Thr Val Ser Phe Ser Phe Pro Gln Ile Thr Leu Trp Gln Arg
     50                  55                  60

Pro Leu Val Thr Ile Lys Ile Gly Gly Gln Leu Lys Glu Ala Leu Leu
 65                  70                  75                  80

Asp Thr Gly Ala Asp Asp Thr Val Leu Glu Glu Met Asn Leu Pro Gly
                 85                  90                  95
```

-continued

```
Arg Trp Lys Pro Lys Met Ile Gly Gly Ile Gly Gly Phe Ile Lys Val
            100                 105                 110
Gly Gln Tyr Asp Gln Ile Leu Ile Glu Ile Cys Gly His Lys Ala Ile
        115                 120                 125
Gly Thr Val Leu Val Gly Pro Thr Pro Val Asn Ile Ile Gly Arg Asn
    130                 135                 140
Leu Leu Thr Gln Ile Gly Cys Thr Leu Asn Phe Pro Ile Ser Pro Ile
145                 150                 155                 160
Glu Thr Val Pro Val Lys Leu Lys Pro Gly Met Asp Gly Pro Lys Val
                165                 170                 175
Lys Gln Trp Pro Leu Thr Glu Glu Lys Ile Lys Ala Leu Val Glu Ile
            180                 185                 190
Cys Thr Glu Met Glu Lys Glu Gly Lys Ile Ser Lys Ile Gly Pro Glu
        195                 200                 205
Asn Pro Tyr Asn Thr Pro Val Phe Ala Ile Lys Lys Lys Asp Ser Thr
    210                 215                 220
Lys Trp Arg Lys Leu Val Asp Phe Arg Glu Leu Asn Lys Arg Thr Gln
225                 230                 235                 240
Asp Phe Trp Glu Val Gln Leu Gly Ile Pro His Pro Ala Gly Leu Lys
                245                 250                 255
Gln Lys Lys Ser Val Thr Val Leu Asp Val Gly Asp Ala Tyr Phe Ser
            260                 265                 270
Val Pro Leu Asp Lys Asp Phe Arg Lys Tyr Thr Ala Phe Thr Ile Pro
        275                 280                 285
Ser Ile Asn Asn Glu Thr Pro Gly Ile Arg Tyr Gln Tyr Asn Val Leu
    290                 295                 300
Pro Gln Gly Trp Lys Gly Ser Pro Ala Ile Phe Gln Cys Ser Met Thr
305                 310                 315                 320
Lys Ile Leu Glu Pro Phe Arg Lys Gln Asn Pro Asp Ile Val Ile Tyr
                325                 330                 335
Gln Tyr Met Asp Asp Leu Tyr Val Gly Ser Asp Leu Glu Ile Gly Gln
            340                 345                 350
His Arg Thr Lys Ile Glu Glu Leu Arg Gln His Leu Leu Arg Trp Gly
        355                 360                 365
Phe Thr Thr Pro Asp Lys Lys His Gln Lys Glu Pro Pro Phe Leu Trp
    370                 375                 380
Met Gly Tyr Glu Leu His Pro Asp Lys Trp Thr Val Gln Pro Ile Val
385                 390                 395                 400
Leu Pro Glu Lys Asp Ser Trp Thr Val Asn Asp Ile Gln Lys Leu Val
                405                 410                 415
Gly Lys Leu Asn Trp Ala Ser Gln Ile Tyr Ala Gly Ile Lys Val Arg
            420                 425                 430
Gln Leu Cys Lys Leu Leu Arg Gly Thr Lys Ala Leu Thr Glu Val Val
        435                 440                 445
Pro Leu Thr Glu Glu Ala Glu Leu Glu Leu Ala Glu Asn Arg Glu Ile
    450                 455                 460
Leu Lys Glu Pro Val His Gly Val Tyr Tyr Asp Pro Ser Lys Asp Leu
465                 470                 475                 480
Ile Ala Glu Ile Gln Lys Gln Gly Gln Gly Gln Trp Thr Tyr Gln Ile
                485                 490                 495
Tyr Gln Glu Pro Phe Lys Asn Leu Lys Thr Gly Lys Tyr Ala Arg Met
            500                 505                 510
Lys Gly Ala His Thr Asn Asp Val Lys Gln Leu Thr Glu Ala Val Gln
```

-continued

```
                515                 520                 525
Lys Ile Ala Thr Glu Ser Ile Val Ile Trp Gly Lys Thr Pro Lys Phe
            530                 535                 540

Lys Leu Pro Ile Gln Lys Glu Thr Trp Glu Ala Trp Trp Thr Glu Tyr
545                 550                 555                 560

Trp Gln Ala Thr Trp Ile Pro Glu Trp Glu Phe Val Asn Thr Pro Pro
                565                 570                 575

Leu Val Lys Leu Trp Tyr Gln Leu Glu Lys Glu Pro Ile Ile Gly Ala
            580                 585                 590

Glu Thr Phe Tyr Val Asp Gly Ala Ala Asn Arg Glu Thr Lys Leu Gly
            595                 600                 605

Lys Ala Gly Tyr Val Thr Asp Arg Gly Arg Gln Lys Val Val Pro Leu
            610                 615                 620

Thr Asp Thr Thr Asn Gln Lys Thr Glu Leu Gln Ala Ile His Leu Ala
625                 630                 635                 640

Leu Gln Asp Ser Gly Leu Glu Val Asn Ile Val Thr Asp Ser Gln Tyr
                645                 650                 655

Ala Leu Gly Ile Ile Gln Ala Gln Pro Asp Lys Ser Glu Ser Glu Leu
            660                 665                 670

Val Ser Gln Ile Ile Glu Gln Leu Ile Lys Lys Glu Lys Val Tyr Leu
            675                 680                 685

Ala Trp Val Pro Ala His Lys Gly Ile Gly Gly Asn Glu Gln Val Asp
            690                 695                 700

Gly Leu Val Ser Ala Gly Ile Arg Lys Val Leu Phe Leu Asp Gly Ile
705                 710                 715                 720

Asp Lys Ala Gln Glu Glu His Glu Lys Tyr His Ser Asn Trp Arg Ala
                725                 730                 735

Met Ala Ser Asp Phe Asn Leu Pro Pro Val Val Ala Lys Glu Ile Val
            740                 745                 750

Ala Ser Cys Asp Lys Cys Gln Leu Lys Gly Glu Ala Met His Gly Gln
            755                 760                 765

Val Asp Cys Ser Pro Gly Ile Trp Gln Leu Asp Cys Thr His Leu Glu
            770                 775                 780

Gly Lys Val Ile Leu Val Ala Val His Val Ala Ser Gly Tyr Ile Glu
785                 790                 795                 800

Ala Glu Val Ile Pro Ala Glu Thr Gly Gln Glu Thr Ala Tyr Phe Leu
                805                 810                 815

Leu Lys Leu Ala Gly Arg Trp Pro Val Lys Thr Val His Thr Asp Asn
            820                 825                 830

Gly Ser Asn Phe Thr Ser Thr Thr Val Lys Ala Ala Cys Trp Trp Ala
            835                 840                 845

Gly Ile Lys Gln Glu Phe Gly Ile Pro Tyr Asn Pro Gln Ser Gln Gly
            850                 855                 860

Val Ile Glu Ser Met Asn Lys Glu Leu Lys Lys Ile Ile Gly Gln Val
865                 870                 875                 880

Arg Asp Gln Ala Glu His Leu Lys Thr Ala Val Gln Met Ala Val Phe
                885                 890                 895

Ile His Asn Phe Lys Arg Lys Gly Gly Ile Gly Gly Tyr Ser Ala Gly
            900                 905                 910

Glu Arg Ile Val Asp Ile Ile Ala Thr Asp Ile Gln Thr Lys Glu Leu
            915                 920                 925

Gln Lys Gln Ile Thr Lys Ile Gln Asn Phe Arg Val Tyr Tyr Arg Asp
            930                 935                 940
```

```
Ser Arg Asp Pro Val Trp Lys Gly Pro Ala Lys Leu Leu Trp Lys Gly
945                 950                 955                 960

Glu Gly Ala Val Val Ile Gln Asp Asn Ser Asp Ile Lys Val Val Pro
                965                 970                 975

Arg Arg Lys Ala Lys Ile Ile Arg Asp Tyr Gly Lys Gln Met Ala Gly
                980                 985                 990

Asp Asp Cys Val Ala Ser Arg Gln Asp Glu Asp
            995                1000
```

```
<210> SEQ ID NO 18
<211> LENGTH: 192
<212> TYPE: PRT
<213> ORGANISM: Human immunodeficiency virus type 1
<220> FEATURE:
<223> OTHER INFORMATION: vif protein

<400> SEQUENCE: 18

Met Glu Asn Arg Trp Gln Val Met Ile Val Trp Gln Val Asp Arg Met
 1               5                  10                  15

Arg Ile Asn Thr Trp Lys Arg Leu Val Lys His His Met Tyr Ile Ser
                20                  25                  30

Arg Lys Ala Lys Asp Trp Phe Tyr Arg His His Tyr Glu Ser Thr Asn
            35                  40                  45

Pro Lys Ile Ser Ser Glu Val His Ile Pro Leu Gly Asp Ala Lys Leu
        50                  55                  60

Val Ile Thr Thr Tyr Trp Gly Leu His Thr Gly Glu Arg Asp Trp His
 65                  70                  75                  80

Leu Gly Gln Gly Val Ser Ile Glu Trp Arg Lys Lys Arg Tyr Ser Thr
                85                  90                  95

Gln Val Asp Pro Asp Leu Ala Asp Gln Leu Ile His Leu His Tyr Phe
                100                 105                 110

Asp Cys Phe Ser Glu Ser Ala Ile Arg Asn Thr Ile Leu Gly Arg Ile
            115                 120                 125

Val Ser Pro Arg Cys Glu Tyr Gln Ala Gly His Asn Lys Val Gly Ser
        130                 135                 140

Leu Gln Tyr Leu Ala Leu Ala Ala Leu Ile Lys Pro Lys Gln Ile Lys
145                 150                 155                 160

Pro Pro Leu Pro Ser Val Arg Lys Leu Thr Glu Asp Arg Trp Asn Lys
                165                 170                 175

Pro Gln Lys Thr Lys Gly His Arg Gly Ser His Thr Met Asn Gly His
                180                 185                 190
```

```
<210> SEQ ID NO 19
<211> LENGTH: 96
<212> TYPE: PRT
<213> ORGANISM: Human immunodeficiency virus type 1
<220> FEATURE:
<223> OTHER INFORMATION: vpr protein

<400> SEQUENCE: 19

Met Glu Gln Ala Pro Glu Asp Gln Gly Pro Gln Arg Glu Pro Tyr Asn
 1               5                  10                  15

Glu Trp Thr Leu Glu Leu Leu Glu Leu Lys Ser Glu Ala Val Arg
                20                  25                  30

His Phe Pro Arg Ile Trp Leu His Asn Leu Gly Gln His Ile Tyr Glu
            35                  40                  45

Thr Tyr Gly Asp Thr Trp Ala Gly Val Glu Ala Ile Ile Arg Ile Leu
```

```
                    50                  55                  60
Gln Gln Leu Leu Phe Ile His Phe Arg Ile Gly Cys Arg His Ser Arg
 65                  70                  75                  80

Ile Gly Val Thr Arg Gln Arg Arg Ala Arg Asn Gly Ala Ser Arg Ser
                 85                  90                  95
```

<210> SEQ ID NO 20
<211> LENGTH: 86
<212> TYPE: PRT
<213> ORGANISM: Human immunodeficiency virus type 1
<220> FEATURE:
<223> OTHER INFORMATION: tat protein

<400> SEQUENCE: 20

```
Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Cys Cys Phe
                20                  25                  30

His Cys Gln Val Cys Phe Met Thr Lys Ala Leu Gly Ile Ser Tyr Gly
             35                  40                  45

Arg Lys Lys Arg Arg Gln Arg Arg Arg Ala His Gln Asn Ser Gln Thr
 50                  55                  60

His Gln Ala Ser Leu Ser Lys Gln Pro Thr Ser Gln Ser Arg Gly Asp
 65                  70                  75                  80

Pro Thr Gly Pro Lys Glu
                 85
```

<210> SEQ ID NO 21
<211> LENGTH: 116
<212> TYPE: PRT
<213> ORGANISM: Human immunodeficiency virus type 1
<220> FEATURE:
<223> OTHER INFORMATION: rev protein

<400> SEQUENCE: 21

```
Met Ala Gly Arg Ser Gly Asp Ser Asp Glu Glu Leu Ile Arg Thr Val
 1               5                  10                  15

Arg Leu Ile Lys Leu Leu Tyr Gln Ser Asn Pro Pro Asn Pro Glu
                20                  25                  30

Gly Thr Arg Gln Ala Arg Arg Asn Arg Arg Arg Arg Trp Arg Glu Arg
             35                  40                  45

Gln Arg Gln Ile His Ser Ile Ser Glu Arg Ile Leu Ser Thr Tyr Leu
 50                  55                  60

Gly Arg Ser Ala Glu Pro Val Pro Leu Gln Leu Pro Pro Leu Glu Arg
 65                  70                  75                  80

Leu Thr Leu Asp Cys Asn Glu Asp Cys Gly Thr Ser Gly Thr Gln Gly
                85                  90                  95

Val Gly Ser Pro Gln Ile Leu Val Glu Ser Pro Thr Val Leu Glu Ser
                100                 105                 110

Gly Thr Lys Glu
        115
```

<210> SEQ ID NO 22
<211> LENGTH: 81
<212> TYPE: PRT
<213> ORGANISM: Human immunodeficiency virus type 1
<220> FEATURE:
<223> OTHER INFORMATION: vpu protein

<400> SEQUENCE: 22

-continued

Met Gln Pro Ile Ile Val Ala Ile Val Ala Leu Val Val Ala Ile Ile
1               5                   10                  15

Ile Ala Ile Val Val Trp Ser Ile Val Ile Ile Glu Tyr Arg Lys Ile
            20                  25                  30

Leu Arg Gln Arg Lys Ile Asp Arg Leu Ile Asp Arg Leu Ile Glu Arg
        35                  40                  45

Ala Glu Asp Ser Gly Asn Glu Ser Glu Gly Glu Val Ser Ala Leu Val
    50                  55                  60

Glu Met Gly Val Glu Met Gly His His Ala Pro Trp Asp Ile Asp Asp
65                  70                  75                  80

Leu

<210> SEQ ID NO 23
<211> LENGTH: 854
<212> TYPE: PRT
<213> ORGANISM: Human immunodeficiency virus type 1
<220> FEATURE:
<223> OTHER INFORMATION: envelope polyprotein

<400> SEQUENCE: 23

Met Arg Val Lys Glu Lys Tyr Gln His Leu Trp Arg Trp Gly Trp Lys
1               5                   10                  15

Trp Gly Thr Met Leu Leu Gly Ile Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Asp Lys Val Gln Lys Glu Tyr Ala Phe Phe
                165                 170                 175

Tyr Lys Leu Asp Ile Val Pro Ile Asp Asn Thr Ser Tyr Arg Leu Ile
            180                 185                 190

Ser Cys Asn Thr Ser Val Ile Thr Gln Ala Cys Pro Lys Val Ser Phe
        195                 200                 205

Glu Pro Ile Pro Ile His Tyr Cys Ala Pro Ala Gly Phe Ala Ile Leu
    210                 215                 220

Lys Cys Asn Asn Lys Thr Phe Asn Gly Thr Gly Pro Cys Thr Asn Val
225                 230                 235                 240

Ser Thr Val Gln Cys Thr His Gly Ile Arg Pro Val Val Ser Thr Gln
                245                 250                 255

Leu Leu Leu Asn Gly Ser Leu Ala Glu Glu Asp Val Val Ile Arg Ser
            260                 265                 270

-continued

```
Ala Asn Phe Thr Asp Asn Ala Lys Thr Ile Ile Val Gln Leu Asn Thr
        275                 280                 285

Ser Val Glu Ile Asn Cys Thr Arg Pro Asn Asn Asn Thr Arg Lys Ser
        290                 295                 300

Ile Arg Ile Gln Arg Gly Pro Gly Arg Ala Phe Val Thr Ile Gly Lys
305                 310                 315                 320

Ile Gly Asn Met Arg Gln Ala His Cys Asn Ile Ser Arg Ala Lys Trp
                325                 330                 335

Asn Ala Thr Leu Lys Gln Ile Ala Ser Lys Leu Arg Glu Gln Phe Gly
            340                 345                 350

Asn Asn Lys Thr Ile Ile Phe Lys Gln Ser Ser Gly Gly Asp Pro Glu
        355                 360                 365

Ile Val Thr His Ser Phe Asn Cys Gly Gly Glu Phe Phe Tyr Cys Asn
        370                 375                 380

Ser Thr Gln Leu Phe Asn Ser Thr Trp Phe Asn Ser Thr Trp Ser Thr
385                 390                 395                 400

Glu Gly Ser Asn Asn Thr Glu Gly Ser Asp Thr Ile Thr Leu Pro Cys
                405                 410                 415

Arg Ile Lys Gln Phe Ile Asn Met Trp Gln Glu Val Gly Lys Ala Met
            420                 425                 430

Tyr Ala Pro Pro Ile Ser Gly Gln Ile Arg Cys Ser Ser Asn Ile Thr
        435                 440                 445

Gly Leu Leu Leu Thr Arg Asp Gly Gly Asn Asn Asn Gly Ser Glu
450                 455                 460

Ile Phe Arg Pro Gly Gly Gly Asp Met Arg Asp Asn Trp Arg Ser Glu
465                 470                 475                 480

Leu Tyr Lys Tyr Lys Val Val Lys Ile Glu Pro Leu Gly Val Ala Pro
                485                 490                 495

Thr Lys Ala Lys Arg Arg Val Val Gln Arg Glu Lys Arg Ala Val Gly
            500                 505                 510

Ile Gly Ala Leu Phe Leu Gly Phe Leu Gly Ala Ala Gly Ser Thr Met
        515                 520                 525

Gly Cys Thr Ser Met Thr Leu Thr Val Gln Ala Arg Gln Leu Leu Ser
530                 535                 540

Asp Ile Val Gln Gln Asn Asn Leu Leu Arg Ala Ile Glu Ala Gln
545                 550                 555                 560

Gln His Leu Leu Gln Leu Thr Val Trp Gly Ile Lys Gln Leu Gln Ala
                565                 570                 575

Arg Ile Leu Ala Val Glu Arg Tyr Leu Lys Asp Gln Gln Leu Leu Gly
            580                 585                 590

Ile Trp Gly Cys Ser Gly Lys Leu Ile Cys Thr Thr Ala Val Pro Trp
        595                 600                 605

Asn Ala Ser Trp Ser Asn Lys Ser Leu Glu Gln Ile Trp Asn Asn Met
610                 615                 620

Thr Trp Met Glu Trp Asp Arg Glu Ile Asn Asn Tyr Thr Ser Leu Ile
625                 630                 635                 640

His Ser Leu Ile Glu Glu Ser Gln Asn Gln Gln Glu Lys Asn Glu Gln
                645                 650                 655

Glu Leu Leu Glu Leu Asp Lys Trp Ala Ser Leu Trp Asn Trp Phe Asn
            660                 665                 670

Ile Thr Asn Trp Leu Trp Tyr Ile Lys Leu Phe Ile Met Ile Val Gly
        675                 680                 685

Gly Leu Val Gly Leu Arg Ile Val Phe Ala Val Leu Ser Ile Val Asn
```

-continued

```
                690                 695                 700
Arg Val Arg Gln Gly Tyr Ser Pro Leu Ser Phe Gln Thr His Leu Pro
705                 710                 715                 720

Ile Pro Arg Gly Pro Asp Arg Pro Glu Gly Ile Glu Glu Gly Gly
                725                 730                 735

Glu Arg Asp Arg Asp Arg Ser Ile Arg Leu Val Asn Gly Ser Leu Ala
                740                 745                 750

Leu Ile Trp Asp Asp Leu Arg Ser Leu Cys Leu Phe Ser Tyr His Arg
                755                 760                 765

Leu Arg Asp Leu Leu Leu Ile Val Thr Arg Ile Val Glu Leu Leu Gly
770                 775                 780

Arg Arg Gly Trp Glu Ala Leu Lys Tyr Trp Trp Asn Leu Leu Gln Tyr
785                 790                 795                 800

Trp Ser Gln Glu Leu Lys Asn Ser Ala Val Asn Leu Leu Asn Ala Thr
                805                 810                 815

Ala Ile Ala Val Ala Glu Gly Thr Asp Arg Val Ile Glu Val Leu Gln
                820                 825                 830

Ala Ala Tyr Arg Ala Ile Arg His Ile Pro Arg Arg Ile Arg Gln Gly
                835                 840                 845

Leu Glu Arg Ile Leu Leu
    850
```

<210> SEQ ID NO 24
<211> LENGTH: 206
<212> TYPE: PRT
<213> ORGANISM: Human immunodeficiency virus type 1
<220> FEATURE:
<223> OTHER INFORMATION: nef protein

<400> SEQUENCE: 24

```
Met Gly Gly Lys Trp Ser Lys Ser Ser Val Ile Gly Trp Pro Ala Val
  1               5                  10                  15

Arg Glu Arg Met Arg Arg Ala Glu Pro Ala Ala Asp Gly Val Gly Ala
                 20                  25                  30

Val Ser Arg Asp Leu Glu Lys His Gly Ala Ile Thr Ser Ser Asn Thr
             35                  40                  45

Ala Ala Asn Asn Ala Ala Cys Ala Trp Leu Glu Ala Gln Glu Glu Glu
         50                  55                  60

Glu Val Gly Phe Pro Val Thr Pro Gln Val Pro Leu Arg Pro Met Thr
 65                  70                  75                  80

Tyr Lys Ala Ala Val Asp Leu Ser His Phe Leu Lys Glu Lys Gly Gly
                 85                  90                  95

Leu Glu Gly Leu Ile His Ser Gln Arg Arg Gln Asp Ile Leu Asp Leu
                100                 105                 110

Trp Ile Tyr His Thr Gln Gly Tyr Phe Pro Asp Trp Gln Asn Tyr Thr
            115                 120                 125

Pro Gly Pro Gly Val Arg Tyr Pro Leu Thr Phe Gly Trp Cys Tyr Lys
        130                 135                 140

Leu Val Pro Val Glu Pro Asp Lys Val Glu Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
            180                 185                 190

His Val Ala Arg Glu Leu His Pro Glu Tyr Phe Lys Asn Cys
```

-continued

```
                195                 200                 205

<210> SEQ ID NO 25
<211> LENGTH: 1497
<212> TYPE: DNA
<213> ORGANISM: Artificial sequence
<220> FEATURE:
<223> OTHER INFORMATION: Description of the artificial sequence:
      LCMV-Variant WE-HPI
<221> NAME/KEY: CDS
<222> LOCATION: ()..(1497)
<223> OTHER INFORMATION: LCMV GP-Variant (Open reading frame)

<223> OTHER INFORMATION: Mutations in comparison with
<400> 1 (2) at
      positions 281 (94), 329 (110), 385 (129), 397 (133), 463
      (155), 521 (174), 543 (181), 631 (211), 793 (265),
      1039 (347), 1363 (455) und 1370 (457).

<400> SEQUENCE: 25 atg ggt cag att gtg aca atg ttt gag gct ttg cct cac atc att gat      48
Met Gly Gln Ile Val Thr Met Phe Glu Ala Leu Pro His Ile Ile Asp
 1               5                  10                  15 gag gtc atc aac att gtc att att gtg ctc att ata atc acg agc atc      96
Glu Val Ile Asn Ile Val Ile Ile Val Leu Ile Ile Ile Thr Ser Ile
                20                  25                  30 aaa gct gtg tac aat ttc gcc acc tgt ggg ata tta gca ctg gtc agc     144
Lys Ala Val Tyr Asn Phe Ala Thr Cys Gly Ile Leu Ala Leu Val Ser
            35                  40                  45 ttc ctt ttt ttg gct ggt agg tcc tgt ggc atg tac ggc ctt aat ggt     192
Phe Leu Phe Leu Ala Gly Arg Ser Cys Gly Met Tyr Gly Leu Asn Gly
        50                  55                  60 ccc gac atc tat aaa ggg gtt tac cag ttc aaa tca gtg gag ttt gat     240
Pro Asp Ile Tyr Lys Gly Val Tyr Gln Phe Lys Ser Val Glu Phe Asp
 65                  70                  75                  80 atg tct cac tta aat ctg acg atg ccc aat gcg tgc tca gcc aac aac     288
Met Ser His Leu Asn Leu Thr Met Pro Asn Ala Cys Ser Ala Asn Asn
                85                  90                  95 tct cat cac tac atc agt atg gga agc tct gga ctg gag cta act ttc     336
Ser His His Tyr Ile Ser Met Gly Ser Ser Gly Leu Glu Leu Thr Phe
            100                 105                 110 act aac gac tcc atc ctt aat cac aat ttt tgc aac tta acc tcc gct     384
Thr Asn Asp Ser Ile Leu Asn His Asn Phe Cys Asn Leu Thr Ser Ala
        115                 120                 125 ttc aac aaa aag act ttt gac cat aca ctc atg agt ata gtc tcg agt     432
Phe Asn Lys Lys Thr Phe Asp His Thr Leu Met Ser Ile Val Ser Ser
130                 135                 140 ctg cac ctc agt att aga ggg aat tcc aac cac aaa gca gtg tct tgt     480
Leu His Leu Ser Ile Arg Gly Asn Ser Asn His Lys Ala Val Ser Cys
145                 150                 155                 160 gat ttt aac aat ggc atc acc att caa tac aac ttg tca ttt tcg gac     528
Asp Phe Asn Asn Gly Ile Thr Ile Gln Tyr Asn Leu Ser Phe Ser Asp
                165                 170                 175 cca cag agc gct ata agc cag tgt agg act ttc aga ggt aga gtc ttg     576
Pro Gln Ser Ala Ile Ser Gln Cys Arg Thr Phe Arg Gly Arg Val Leu
            180                 185                 190 gac atg ttt aga act gcc ttt gga gga aaa tac atg aga agt ggc tgg     624
Asp Met Phe Arg Thr Ala Phe Gly Gly Lys Tyr Met Arg Ser Gly Trp
        195                 200                 205 ggc tgg gca ggt tca gat ggc aag acc act tgg tgc agc caa aca agc     672
Gly Trp Ala Gly Ser Asp Gly Lys Thr Thr Trp Cys Ser Gln Thr Ser
210                 215                 220
```

```
tat cag tac cta atc ata caa aac agg act tgg gaa aac cac tgt aga      720
Tyr Gln Tyr Leu Ile Ile Gln Asn Arg Thr Trp Glu Asn His Cys Arg
225                 230                 235                 240 tat gca ggc cct ttt ggg atg tct aga atc ctc ttt gct cag gaa aag      768
Tyr Ala Gly Pro Phe Gly Met Ser Arg Ile Leu Phe Ala Gln Glu Lys
                245                 250                 255 aca aag ttt ctc act agg aga ctt gca ggc aca ttc acc tgg acc ctg      816
Thr Lys Phe Leu Thr Arg Arg Leu Ala Gly Thr Phe Thr Trp Thr Leu
            260                 265                 270 tca gac tcc tca gga gta gaa aat cca ggt ggt tat tgc ctg acc aaa      864
Ser Asp Ser Ser Gly Val Glu Asn Pro Gly Gly Tyr Cys Leu Thr Lys
        275                 280                 285 tgg atg atc ctt gct gca gag ctc aaa tgt ttt ggg aat aca gct gtt      912
Trp Met Ile Leu Ala Ala Glu Leu Lys Cys Phe Gly Asn Thr Ala Val
    290                 295                 300 gca aaa tgt aat gtc aat cat gat gaa gag ttc tgt gac atg cta cga      960
Ala Lys Cys Asn Val Asn His Asp Glu Glu Phe Cys Asp Met Leu Arg
305                 310                 315                 320 cta att gat tac aac aag gcc gcc ctg agt aag ttc aag caa gat gta     1008
Leu Ile Asp Tyr Asn Lys Ala Ala Leu Ser Lys Phe Lys Gln Asp Val
                325                 330                 335 gag tct gcc ttg cat gta ttc aaa aca aca gta aat tct ctg att tcc     1056
Glu Ser Ala Leu His Val Phe Lys Thr Thr Val Asn Ser Leu Ile Ser
            340                 345                 350 gat cag ctg ttg atg agg aat cat cta aga gat cta atg ggg gta cca     1104
Asp Gln Leu Leu Met Arg Asn His Leu Arg Asp Leu Met Gly Val Pro
        355                 360                 365 tac tgt aat tac tca aag ttc tgg tat ctg gaa cat gct aag act ggt     1152
Tyr Cys Asn Tyr Ser Lys Phe Trp Tyr Leu Glu His Ala Lys Thr Gly
    370                 375                 380 gag act agt gta ccc aag tgc tgg ctt gtc act aat ggc tcc tac ttg     1200
Glu Thr Ser Val Pro Lys Cys Trp Leu Val Thr Asn Gly Ser Tyr Leu
385                 390                 395                 400 aat gag acc cac ttt agt gat caa atc gaa caa gaa gca gat aac atg     1248
Asn Glu Thr His Phe Ser Asp Gln Ile Glu Gln Glu Ala Asp Asn Met
                405                 410                 415 atc aca gag atg ttg agg aag gac tac ata aaa aga caa ggg agt act     1296
Ile Thr Glu Met Leu Arg Lys Asp Tyr Ile Lys Arg Gln Gly Ser Thr
            420                 425                 430 cct tta gcc tta atg gat ctt ttg atg ttt tca aca tca gca tat cta     1344
Pro Leu Ala Leu Met Asp Leu Leu Met Phe Ser Thr Ser Ala Tyr Leu
        435                 440                 445 atc agc atc ttt ctg cat ctt gtg aag ata cca aca cat aga cac ata     1392
Ile Ser Ile Phe Leu His Leu Val Lys Ile Pro Thr His Arg His Ile
    450                 455                 460 aag ggc ggt tca tgt cca aag cca cac cgc ttg acc aac aag ggg atc     1440
Lys Gly Gly Ser Cys Pro Lys Pro His Arg Leu Thr Asn Lys Gly Ile
465                 470                 475                 480 tgt agt tgt ggt gca ttc aag gtg cct ggt gta aaa act atc tgg aaa     1488
Cys Ser Cys Gly Ala Phe Lys Val Pro Gly Val Lys Thr Ile Trp Lys
                485                 490                 495 aga cgc tga                                                         1497
Arg Arg <210> SEQ ID NO 26
<211> LENGTH: 498
<212> TYPE: PRT
<213> ORGANISM: Artificial sequence
<220> FEATURE:
<223> OTHER INFORMATION: Description of the artificial sequence:
      LCMV-Variant WE-GP
```

-continued

```
<400> SEQUENCE: 26

Met Gly Gln Ile Val Thr Met Phe Glu Ala Leu Pro His Ile Ile Asp
  1               5                  10                  15

Glu Val Ile Asn Ile Val Ile Val Leu Ile Ile Thr Ser Ile
             20                  25                  30

Lys Ala Val Tyr Asn Phe Ala Thr Cys Gly Ile Leu Ala Leu Val Ser
             35                  40                  45

Phe Leu Phe Leu Ala Gly Arg Ser Cys Gly Met Tyr Gly Leu Asn Gly
         50                  55                  60

Pro Asp Ile Tyr Lys Gly Val Tyr Gln Phe Lys Ser Val Glu Phe Asp
 65                  70                  75                  80

Met Ser His Leu Asn Leu Thr Met Pro Asn Ala Cys Ser Ala Asn Asn
                 85                  90                  95

Ser His His Tyr Ile Ser Met Gly Ser Ser Gly Leu Glu Leu Thr Phe
                100                 105                 110

Thr Asn Asp Ser Ile Leu Asn His Asn Phe Cys Asn Leu Thr Ser Ala
                115                 120                 125

Phe Asn Lys Lys Thr Phe Asp His Thr Leu Met Ser Ile Val Ser Ser
        130                 135                 140

Leu His Leu Ser Ile Arg Gly Asn Ser Asn His Lys Ala Val Ser Cys
145                 150                 155                 160

Asp Phe Asn Asn Gly Ile Thr Ile Gln Tyr Asn Leu Ser Phe Ser Asp
                165                 170                 175

Pro Gln Ser Ala Ile Ser Gln Cys Arg Thr Phe Arg Gly Arg Val Leu
                180                 185                 190

Asp Met Phe Arg Thr Ala Phe Gly Gly Lys Tyr Met Arg Ser Gly Trp
        195                 200                 205

Gly Trp Ala Gly Ser Asp Gly Lys Thr Thr Trp Cys Ser Gln Thr Ser
        210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Lys Phe Leu Thr Arg Arg Leu Ala Gly Thr Phe Thr Trp Thr Leu
                260                 265                 270

Ser Asp Ser Ser Gly Val Glu Asn Pro Gly Gly Tyr Cys Leu Thr Lys
                275                 280                 285

Trp Met Ile Leu Ala Ala Glu Leu Lys Cys Phe Gly Asn Thr Ala Val
        290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Gln Asp Val
                325                 330                 335

Glu Ser Ala Leu His Val Phe Lys Thr Thr Val Asn Ser Leu Ile Ser
                340                 345                 350

Asp Gln Leu Leu Met Arg Asn His Leu Arg Asp Leu Met Gly Val Pro
        355                 360                 365

Tyr Cys Asn Tyr Ser Lys Phe Trp Tyr Leu Glu His Ala Lys Thr Gly
        370                 375                 380

Glu Thr Ser Val Pro Lys Cys Trp Leu Val Thr Asn Gly Ser Tyr Leu
385                 390                 395                 400

Asn Glu Thr His Phe Ser Asp Gln Ile Glu Gln Glu Ala Asp Asn Met
```

-continued

```
                     405                 410                 415
Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
        435                 440                 445

Ile Ser Ile Phe Leu His Leu Val Lys Ile Pro Thr His Arg His Ile
    450                 455                 460

Lys Gly Gly Ser Cys Pro Lys Pro His Arg Leu Thr Asn Lys Gly Ile
465                 470                 475                 480

Cys Ser Cys Gly Ala Phe Lys Val Pro Gly Val Lys Thr Ile Trp Lys
                485                 490                 495

Arg Arg
```